United States Patent [19]

Kumazawa

[11] Patent Number: 5,240,955

[45] Date of Patent: Aug. 31, 1993

[54] AZOLE DERIVATIVE AND AZOLE MYCOCIDE

[75] Inventor: Satoru Kumazawa, Iwaki, Japan

[73] Assignee: Kureha Kagaku Kogyo Kabushiki Kaisha, Tokyo, Japan

[21] Appl. No.: 928,954

[22] Filed: Aug. 13, 1992

Related U.S. Application Data

[60] Division of Ser. No. 666,488, Mar. 6, 1991, Pat. No. 5,162,356, which is a continuation of Ser. No. 201,982, Jun. 3, 1988, abandoned.

Foreign Application Priority Data

Jun. 5, 1987 [JP]  Japan .................. 62-141144
Dec. 16, 1987 [JP]  Japan .................. 62-317754

[51] Int. Cl.$^5$ .................. A61K 31/415; C07D 233/60
[52] U.S. Cl. .................. 514/399; 548/340.1; 548/341.1
[58] Field of Search .......... 548/341, 340.1, 341.1; 514/399

[56] References Cited

U.S. PATENT DOCUMENTS

| | | | |
|---|---|---|---|
| 4,503,062 | 3/1985 | Gravestock | 514/383 |
| 5,028,254 | 7/1991 | Kumazawa et al. | 71/92 |

Primary Examiner—Patricia L. Morris
Attorney, Agent, or Firm—Nixon & Vanderhye

[57] ABSTRACT

Disclosed herein are azole derivatives or the salts thereof which are represented by the general formula (I):

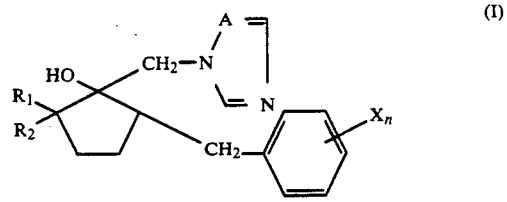

wherein X represents a halogen atom, an alkyl group having 1 to 5 carbon atoms, a haloalkyl group, a phenyl group, a cyano group, or a nitro group, Xs being either the same or different from each other; n represents an integer of 1 to 5; A represents a nitrogen atom or CH; and one of $R_1$ and $R_2$ represents an alkyl group having 1 to 5 carbon atoms and the other a hydrogen atom or an alkyl group having 1 to 5 carbon atoms, with the proviso that when n is 1 or 2, X does not represent a halogen atom, an alkyl group having 1 to 5 carbon atoms or a phenyl group, and mycocides comprising an effective amount of azole derivative or medically or veterinarily acceptable salt thereof, said azole derivative being represented by the general formula (II):

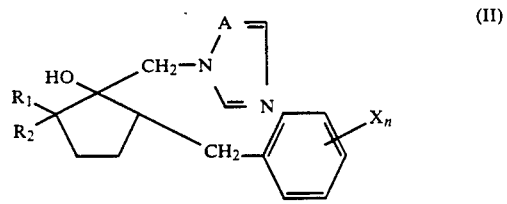

wherein X represents a halogen atom, an alkyl group having 1 to 5 carbon atoms, a haloalkyl group, a phenyl group, a cyano group, or a nitro group, Xs being either the same or different from each other; n represents an integer of 0 to 5; A represents a nitrogen atom or CH; and $R_1$ and $R_2$ respectively represent a hydrogen atom or an alkyl group having 1 to 5 carbon atoms, and a diluent or a carrier which is medically or veterinarily acceptable.

2 Claims, 55 Drawing Sheets

AZOLE DERIVATIVE AND AZOLE MYCOCIDE

CROSS-REFERENCE TO RELATED APPLICATIONS

This application is a division of earlier application Ser. No. 07/666,488 filed Mar. 6, 1991, now U.S. Pat. No. 5,162,356 which, in turn, is a continuation of application Ser. No. 07/201,982 filed Jun. 3, 1988, now abandoned.

BACKGROUND OF THE INVENTION

The present invention relates to azole derivatives or the salts thereof which are represented by the formula (I):

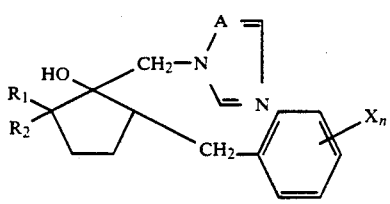

wherein X represents a halogen atom, an alkyl group having 1 to 5 carbon atoms, a haloalkyl group, a phenyl group, a cyano group, or a nitro group, Xs being either the same or different from each other; n represents an integer of 1 to A represents a nitrogen atom or CH; and one of $R_1$ and $R_2$ represents an alkyl group having 1 to 5 carbon atoms and the other a hydrogen atom or an alkyl group having 1 to 5 carbon atoms, with the proviso that when n is 1 or 2, X does not represent a halogen atom, an alkyl group having 1 to 5 carbon atoms or a phenyl group and mycocides useful for animals including man, which contain as an effective ingredient an effective amount of azole derivative represented by the formula (II):

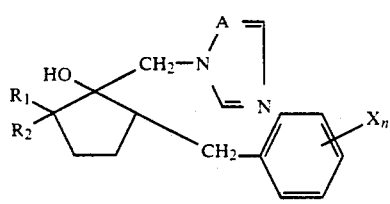

wherein X represents a halogen atom, an alkyl group having 1 to 5 carbon atoms, a haloalkyl group, a phenyl group, a cyano group, or a nitro group, Xs being either the same or different from each other; n represents an integer of 0 to 5; A represents a nitrogen atom or CH; and $R_1$ and $R_2$ respectively represent a hydrogen atom or an alkyl group having 1 to 5 carbon atoms or a salt thereof which is medically or veterinarily acceptable.

The fact that a part of the compounds represented by the formula (II) have action of protecting plants from phytopathogens, growth-regulating effects and herbicidal effects on plants as agricultural and horticultural chemicals has already been reported together with the methods for producing the compounds by the present inventors (Japanese Patent Application Nos. 60-202431 (1985) and 61-265559 (1986)).

As a result of further studies of the adaptability of the compounds disclosed in Japanese Patent Application Nos. 60-202431 (1985) and 61-265559 (1986) and novel compounds to fields other than the fields of agricultural and horticultural chemicals, the present inventors have found that the known compounds and novel compounds represented by the formula (I) have mycocidal effects on animals including man. The present invention has been achieved on the basis of this finding.

SUMMARY OF THE INVENTION

In a first aspect of the present invention, there is provided an azole derivative represented by the formula (I):

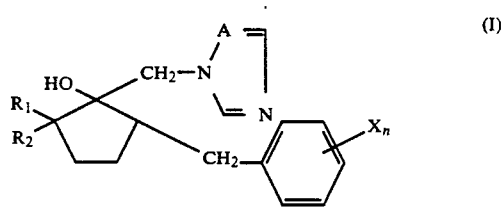

wherein X represents a halogen atom, an alkyl group having 1 to 5 carbon atoms, a haloalkyl group, a phenyl group, a cyano group, or a nitro group, Xs being either the same or different from each other; n represents an integer of 1 to 5; A represents a nitrogen atom or CH; and one of $R_1$ and $R_2$ atoms and the represents an alkyl group having 1 to 5 carbon other a hydrogen atom or an alkyl group having 1 to 5 carbon atoms, with the proviso that when n is 1 or 2, X does not represent a halogen atom, an alkyl group having 1 to 5 carbon atoms or a phenyl group, and a salt thereof.

In a second aspect of the present invention, there is provided a mycocide which comprises an effective amount of azole derivative represented by the formula (II):

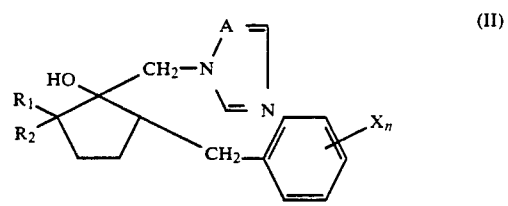

wherein X represents a halogen atom, an alkyl group having 1 to 5 carbon atoms, a haloalkyl group, a phenyl group, a cyano group, or a nitro group, Xs being either the same or different from each other; n represents an integer of 0 to 5; A represents a nitrogen atom or CH; and $R_1$ and $R_2$ respectively represent a hydrogen atom or an alkyl group having 1 to 5 carbon atoms, or a medically or veterinarily acceptable salt thereof, and a diluent or a carrier which is medically or veterinarily acceptable.

In a third aspect of the present invention, there is provided a method for treating mycosis of man or an animal comprising administering an effective amount of azole derivative represented by the formula (II):

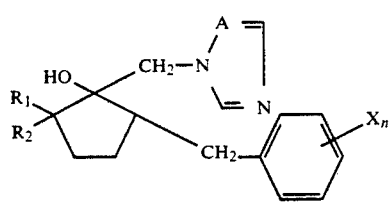

(II)

wherein X represents a halogen atom, an alkyl group having 1 to 5 carbon atoms, a haloalkyl group, a phenyl group, a cyano group, or a nitro group, Xs being either the same or different from each other; n represents an integer of 0 to 5; A represents a nitrogen atom or CH; and $R_1$ and $R_2$ respectively represent a hydrogen atom or an alkyl group having 1 to 5 carbon atoms, or a medically or veterinarily acceptable salt thereof.

In a fourth aspect of the present invention, there is provided a use of an azole derivative represented by the formula (II):

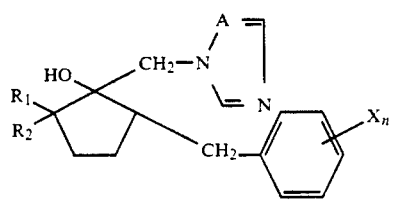

(II)

wherein X represents a halogen atom, an alkyl group having 1 to 5 carbon atoms, a haloalkyl group, a phenyl group, a cyano group, or a nitro group, Xs being either the same or different from each other; n represents an integer of 0 to 5; A represents a nitrogen atom or CH; and $R_1$ and $R_2$ respectively represent a hydrogen atom or an alkyl group having 1 to 5 carbon atoms, or a medically or veterinarily acceptable salt thereof for producing a mycocide.

BRIEF DESCRIPTION OF THE DRAWINGS

FIGS. 1 to 110 show the infrared absorption spectra of the azole derivative shown in Table 1, wherein FIG. 1 shows the infrared absorption spectrum of Compound No. 1, FIG. 2 that of Compound No. 2, FIG. 3 that of Compound No. 3, and FIGS. 4 to 110 those of Compound Nos. 4 to 110, respectively.

DETAILED DESCRIPTION OF THE INVENTION

Figure 1:
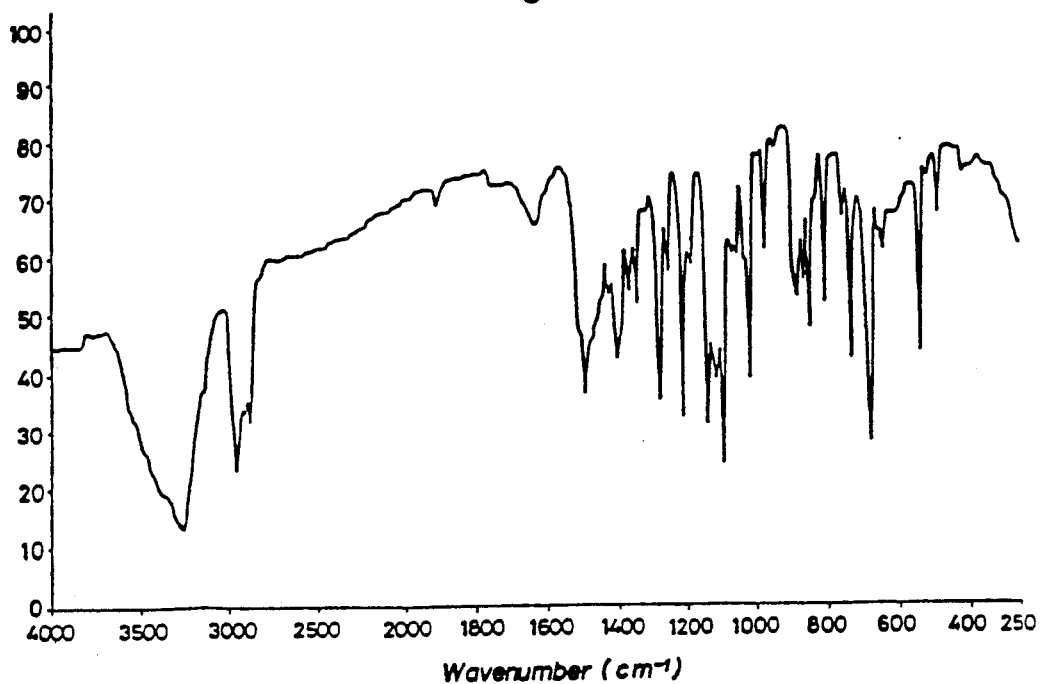
Figure 2:
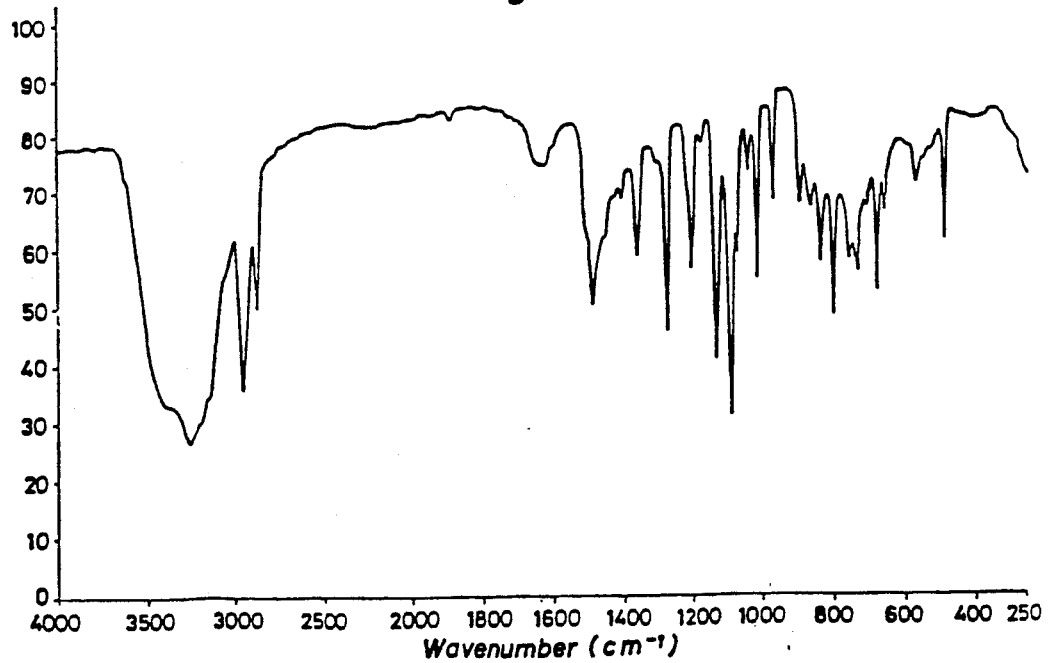
Figure 3:
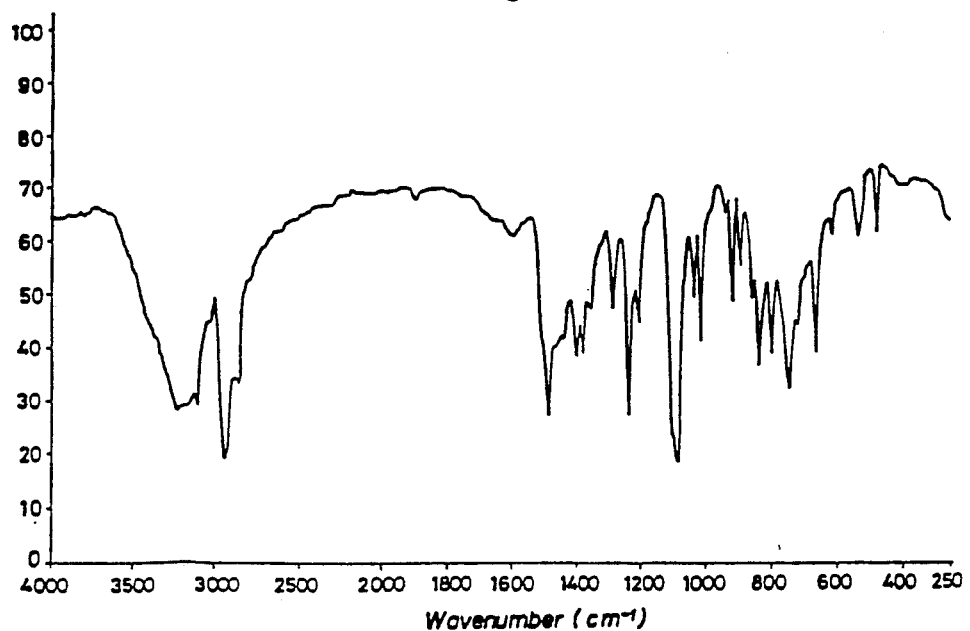
Figure 4:
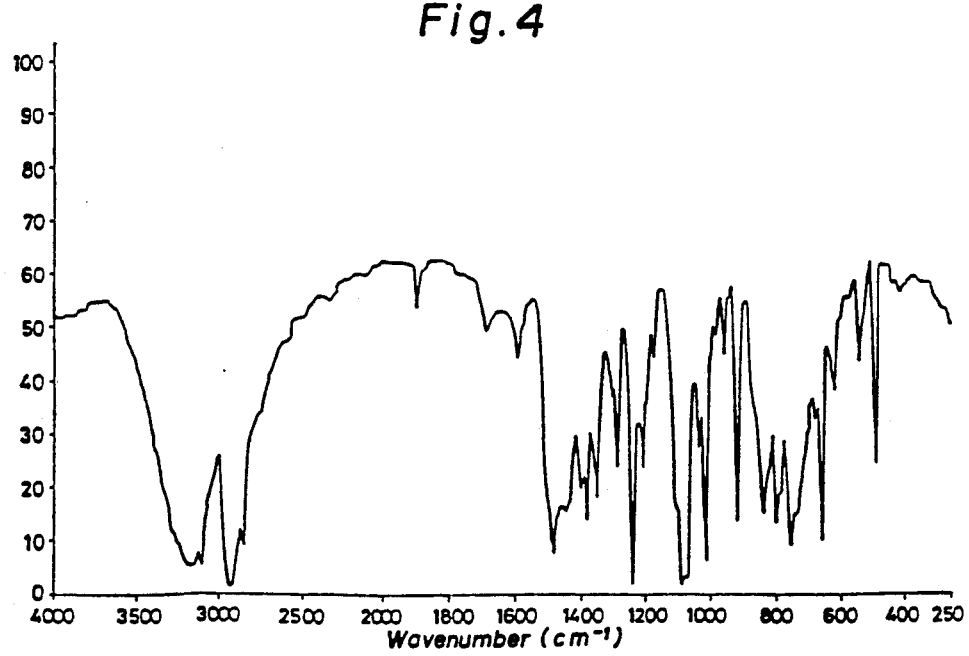
Figure 5:
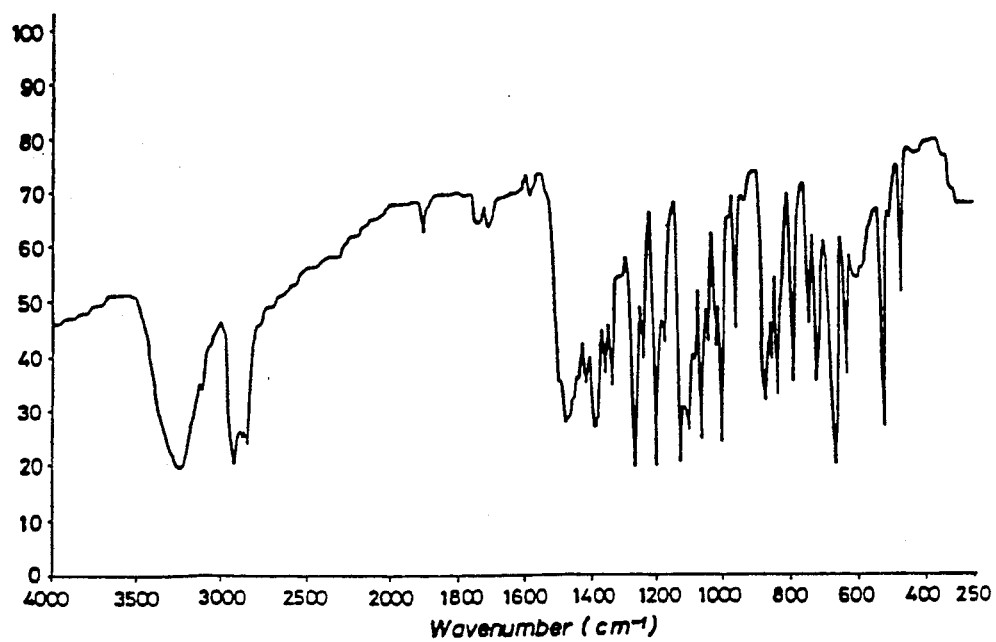
Figure 6:
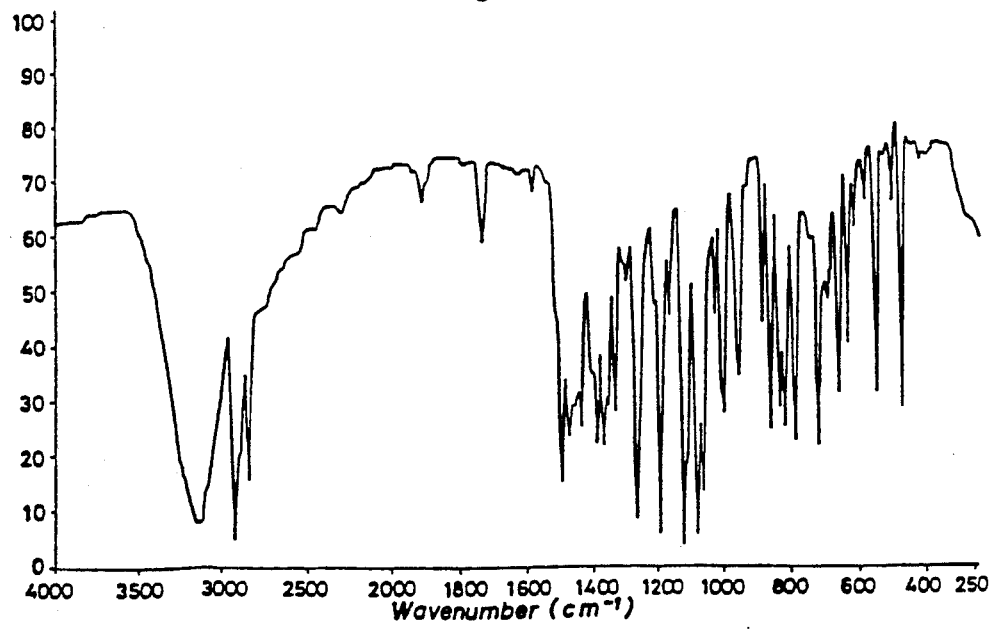
Figure 7:
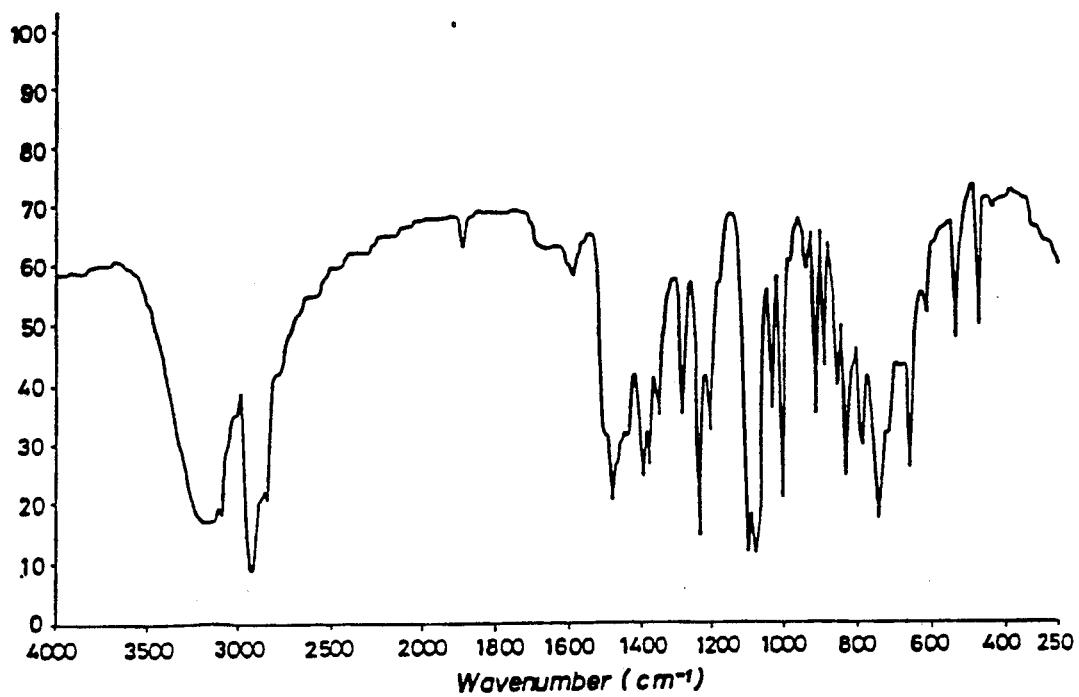
Figure 8:
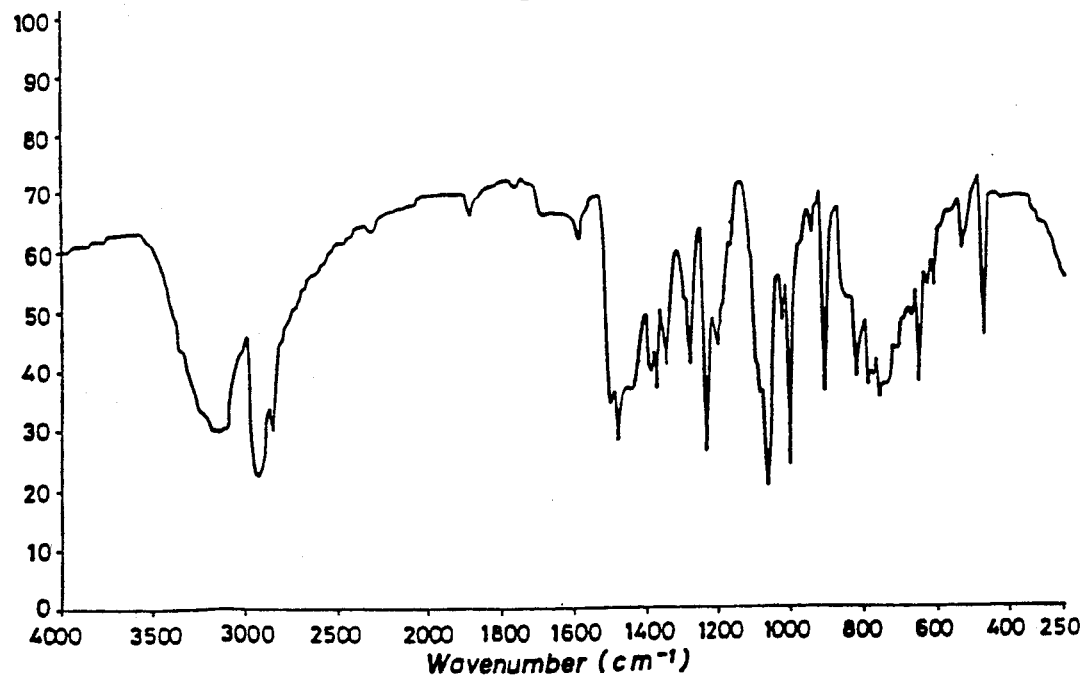
Figure 9:
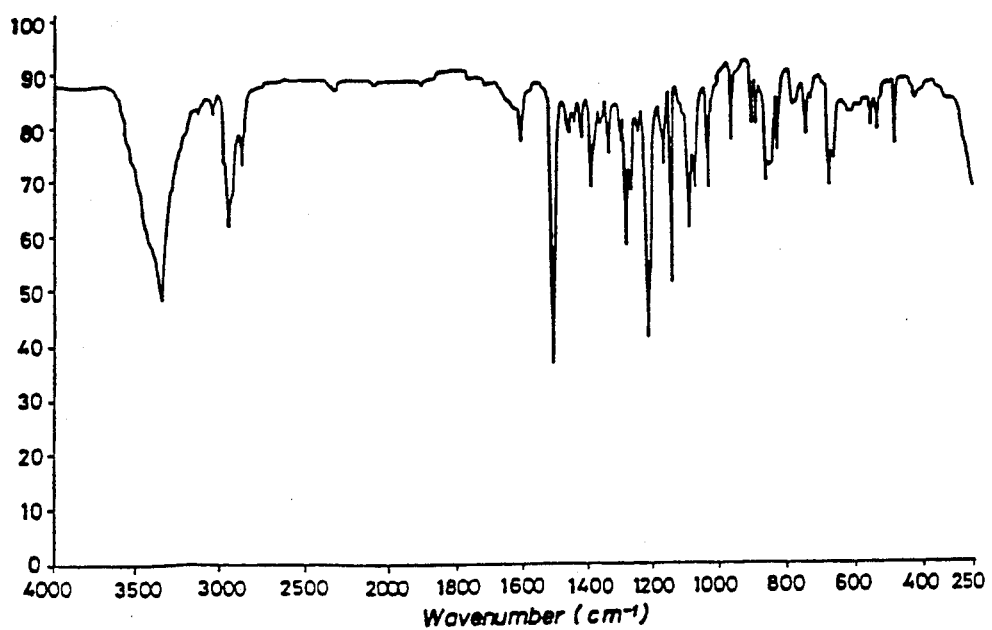
Figure 10:
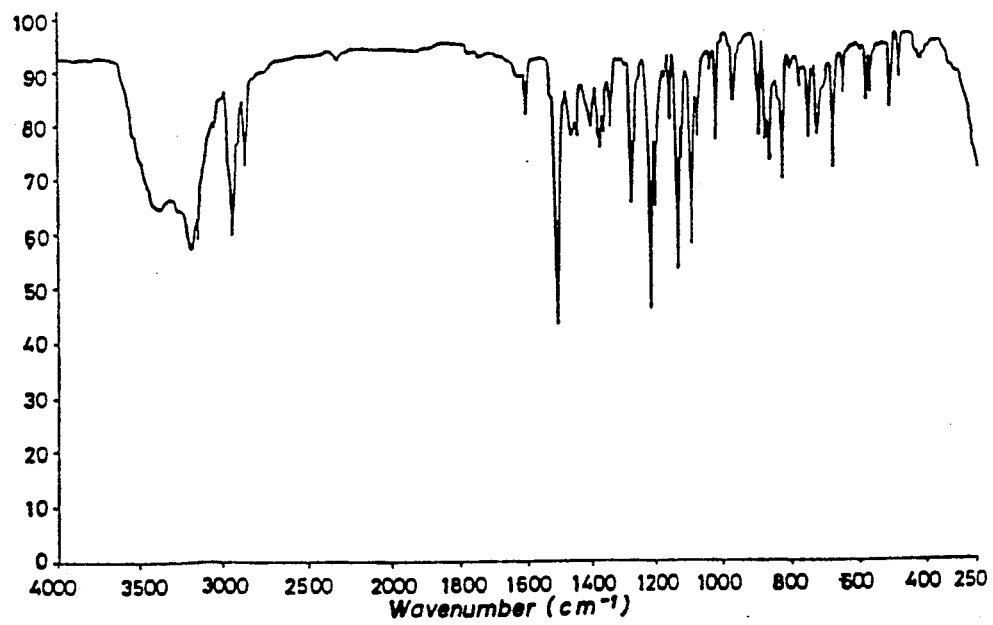
Figure 11:
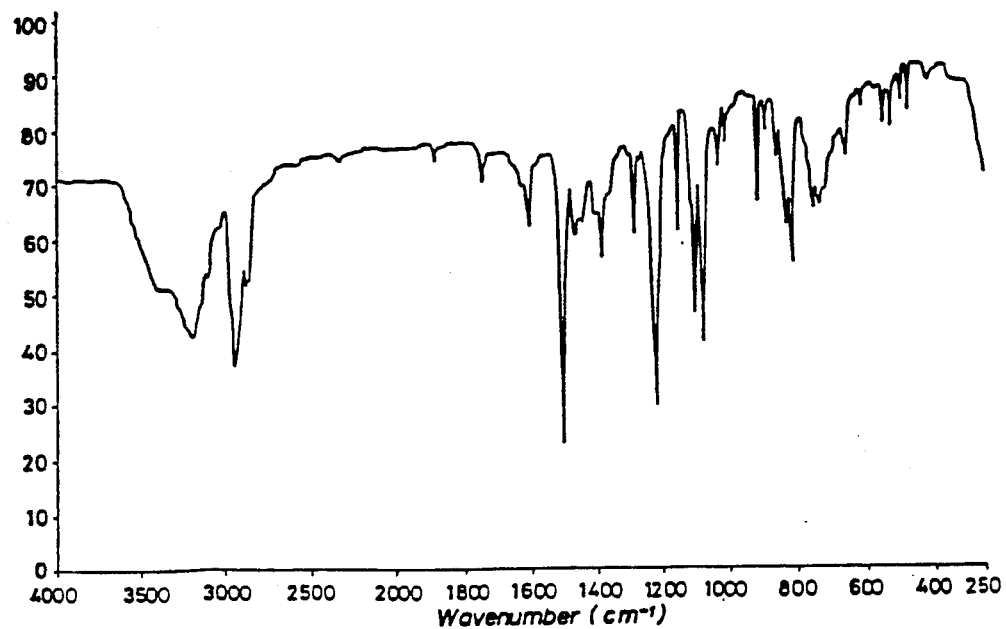
Figure 12:
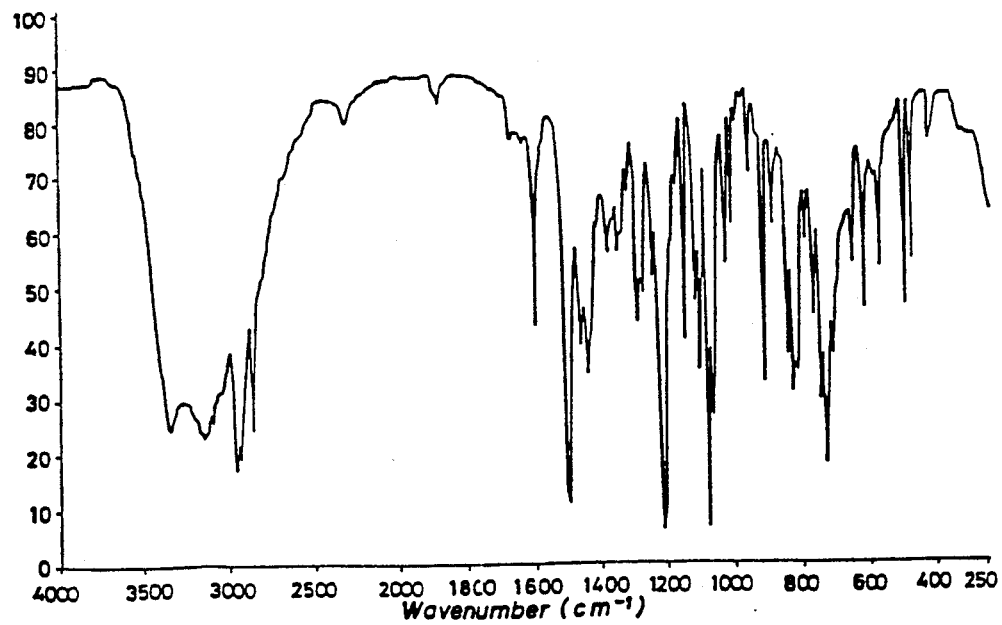
Figure 13:
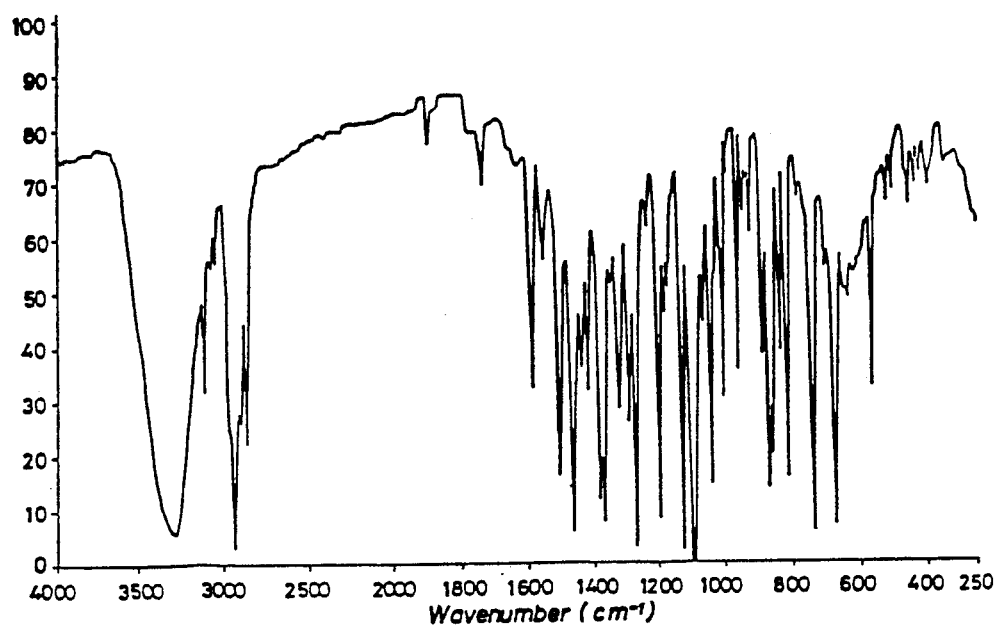
Figure 14:
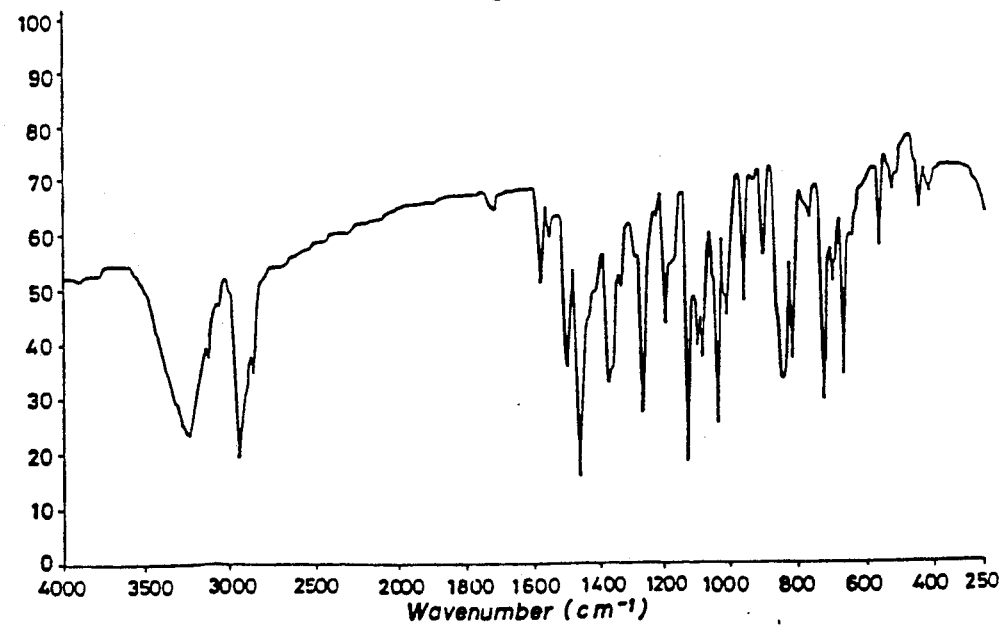
Figure 15:
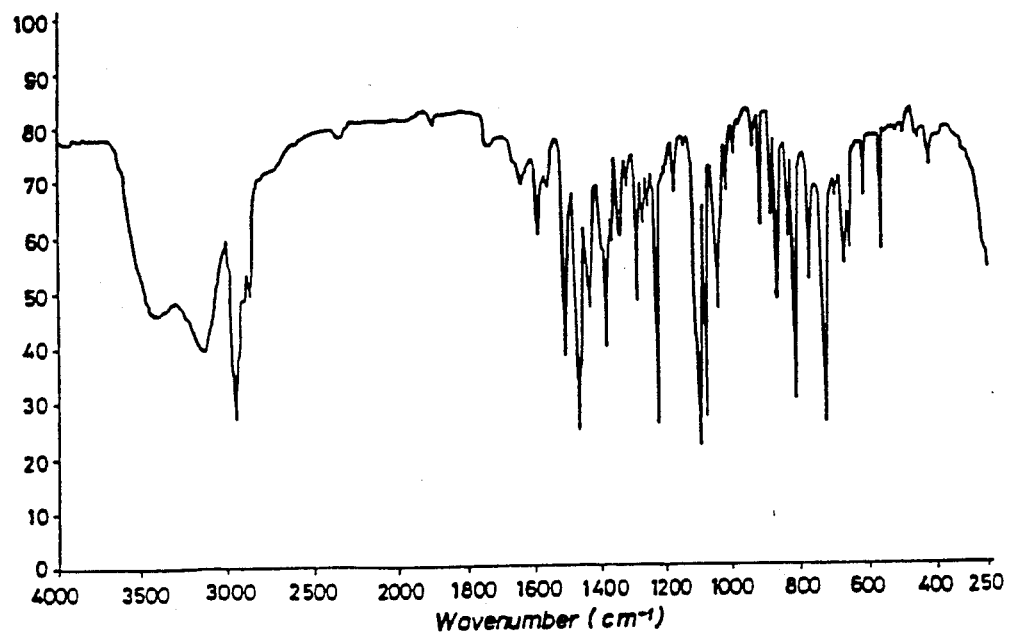
Figure 16:
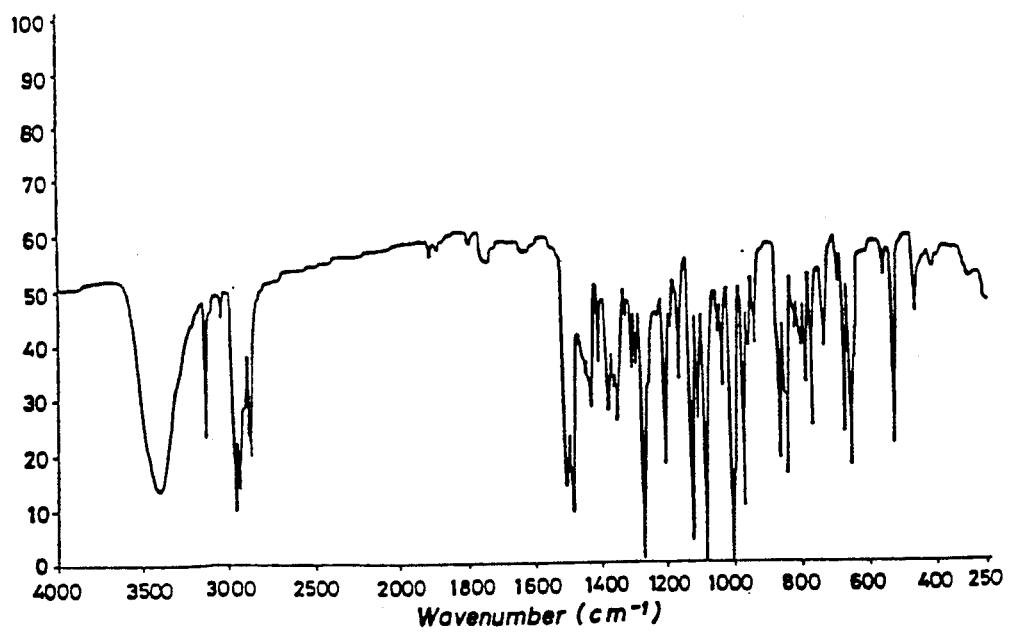
Figure 17:
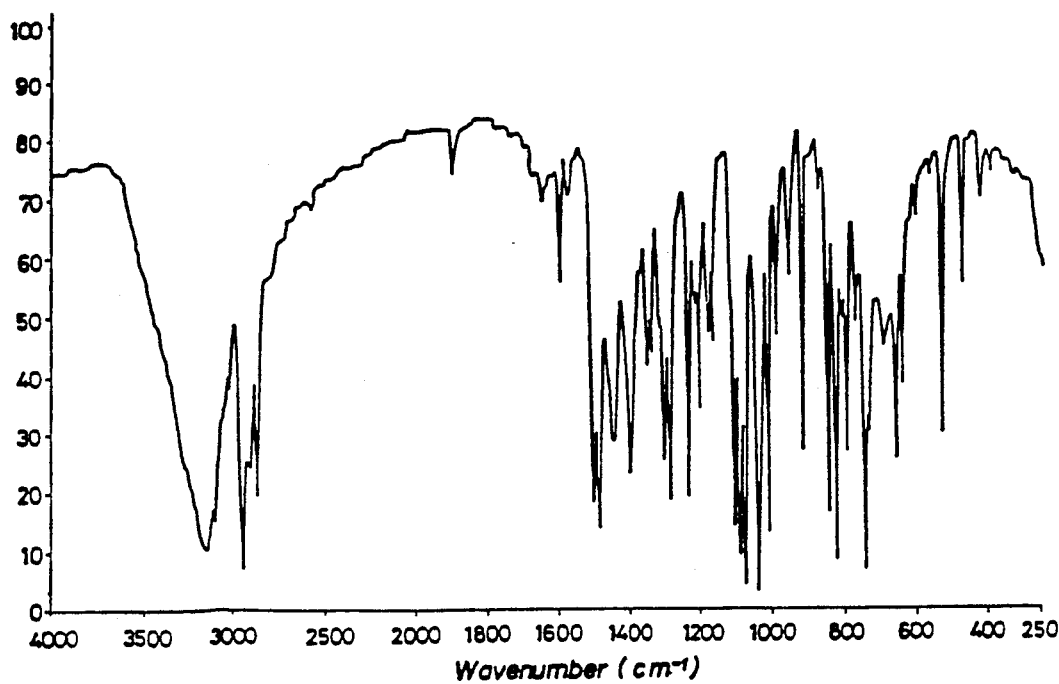
Figure 18:
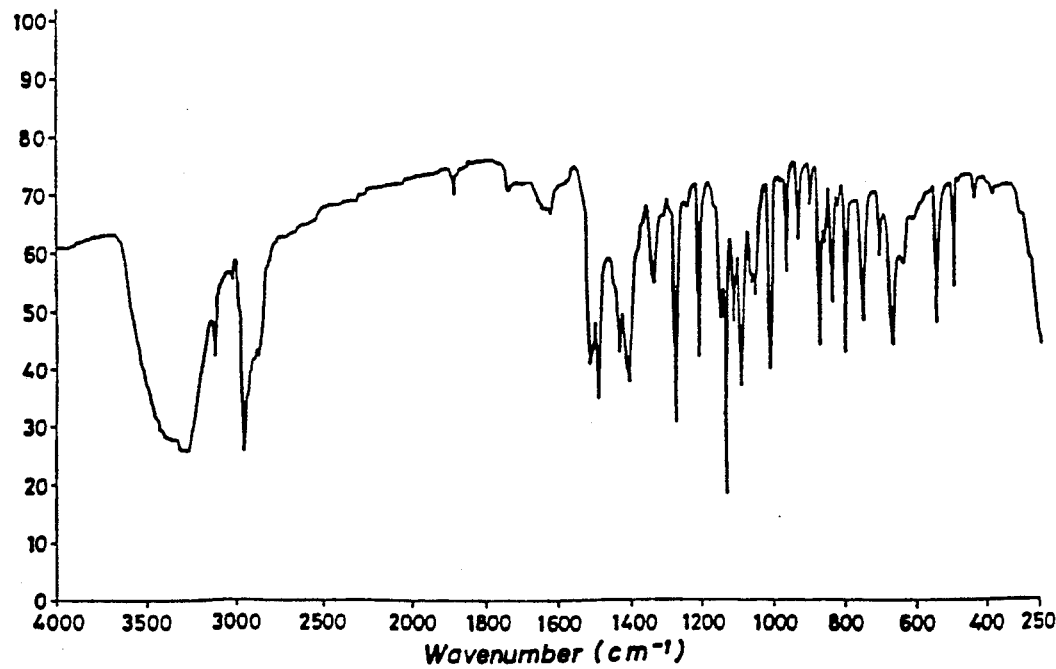
Figure 19:
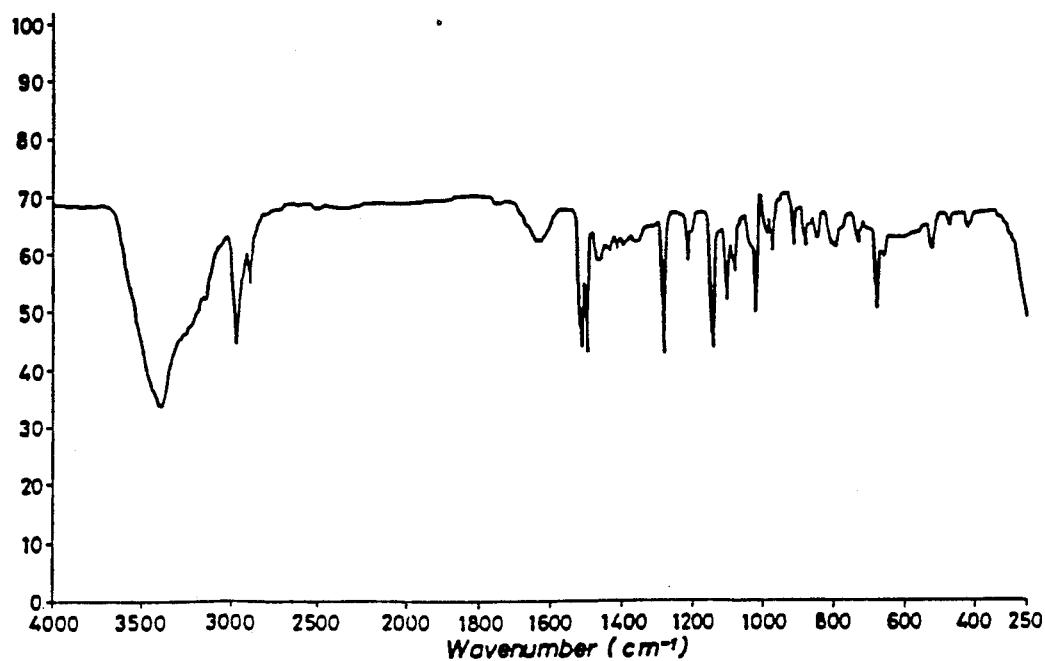
Figure 20:
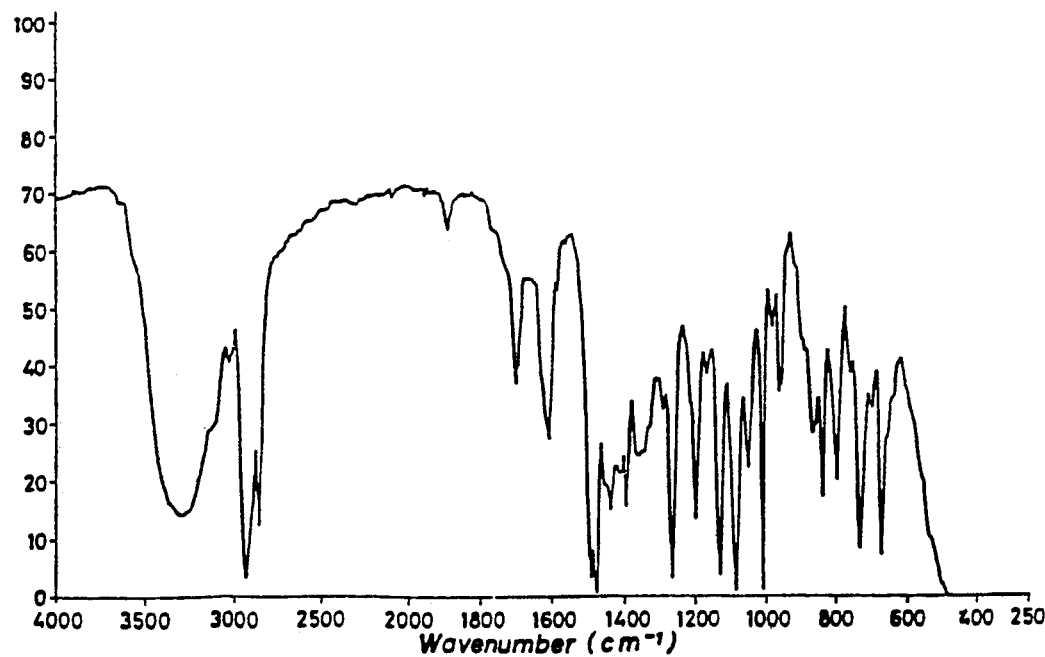
Figure 21:
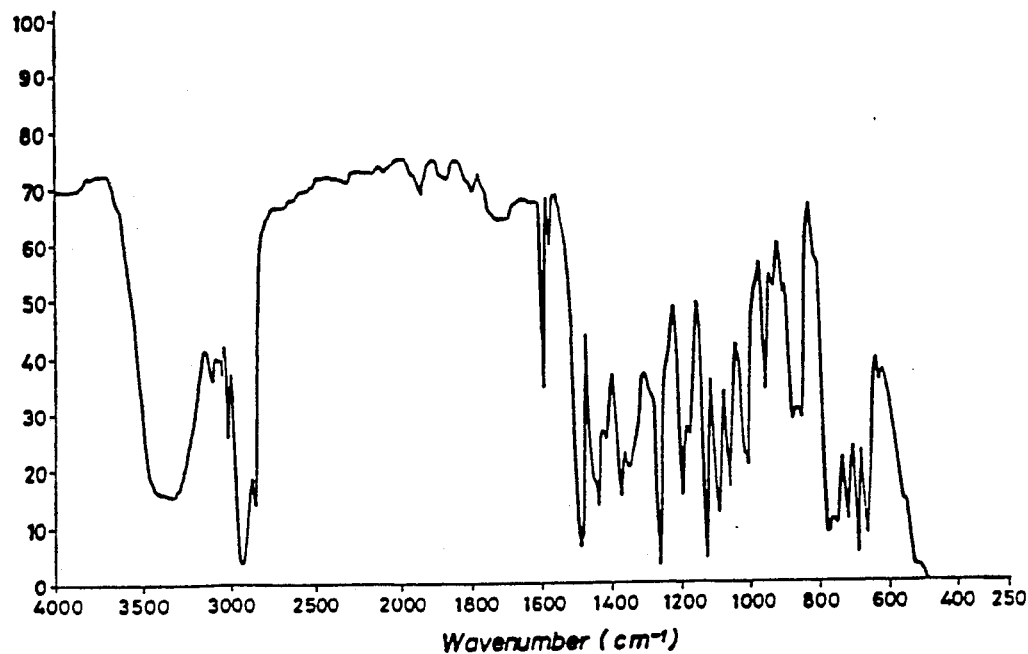
Figure 22:
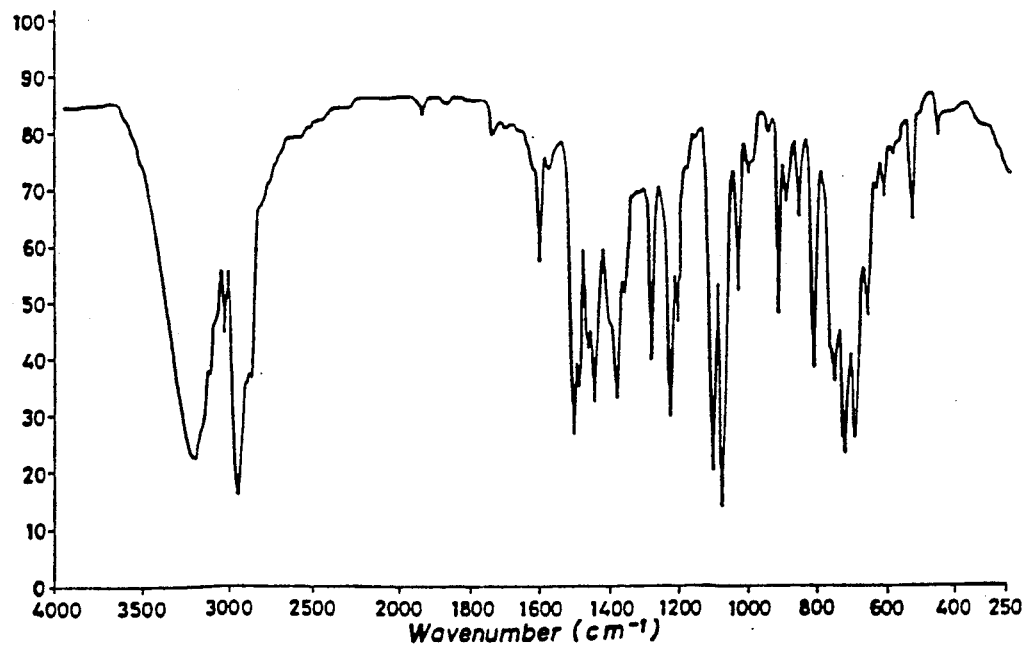
Figure 23:
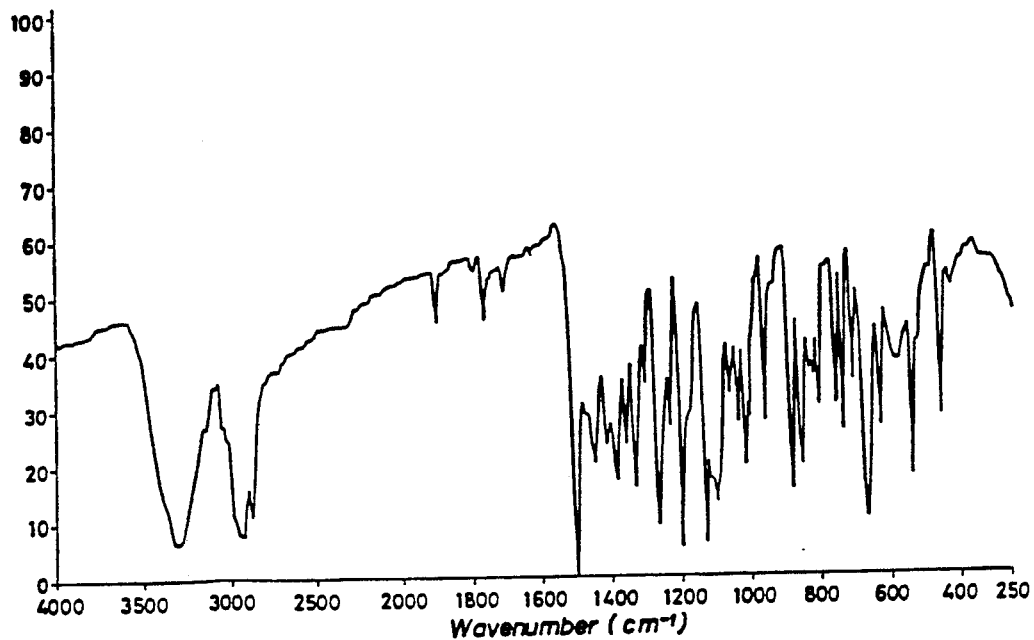
Figure 24:
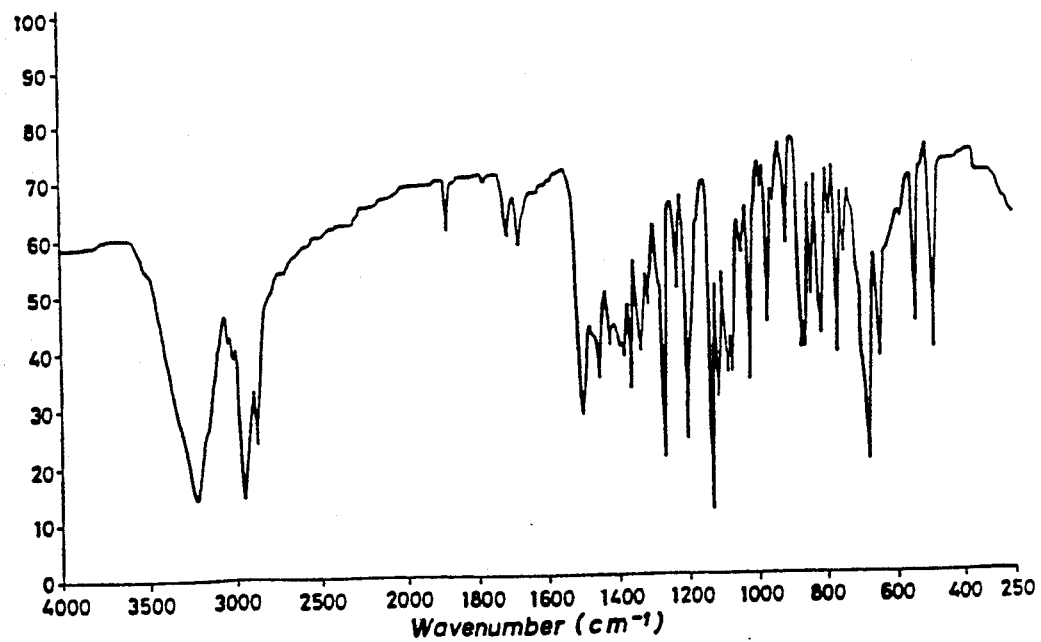
Figure 25:
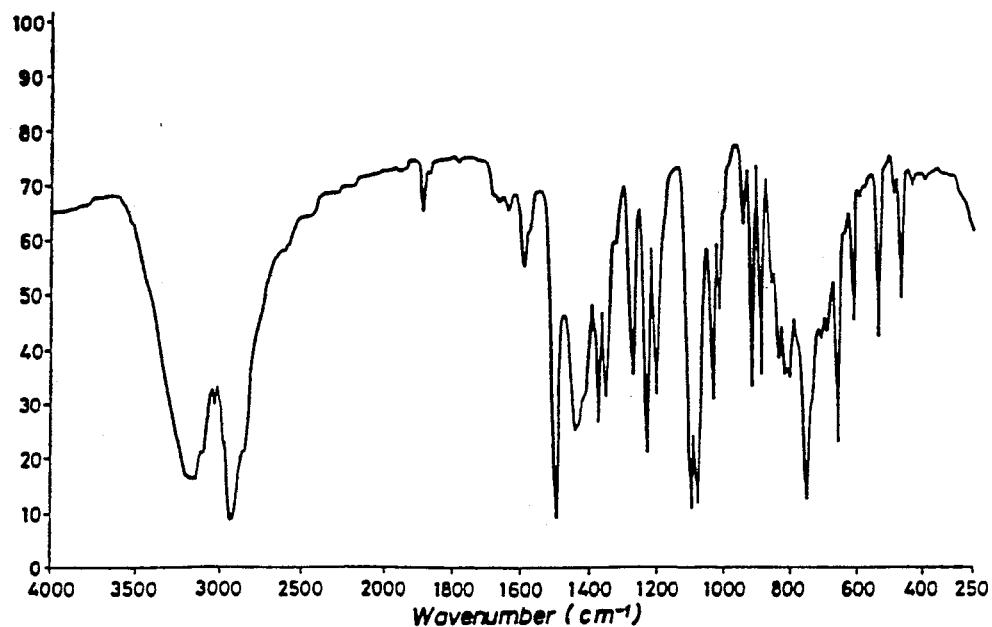
Figure 26:
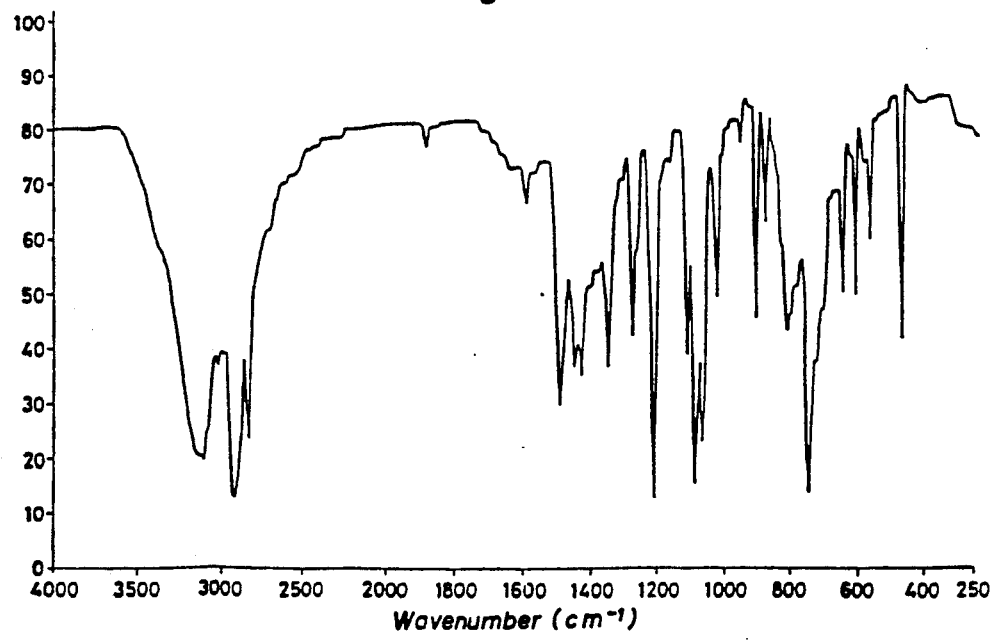
Figure 27:
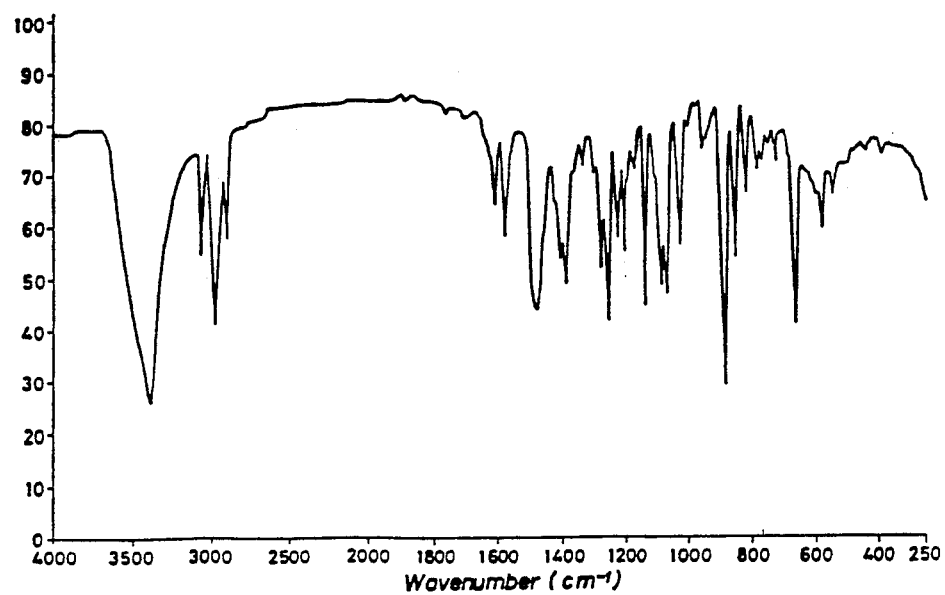
Figure 28:
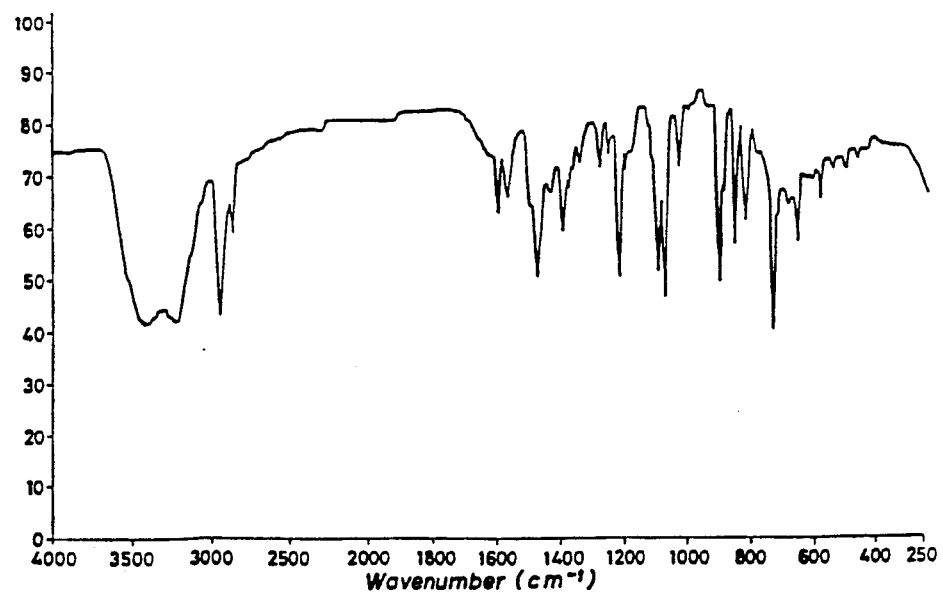
Figure 29:
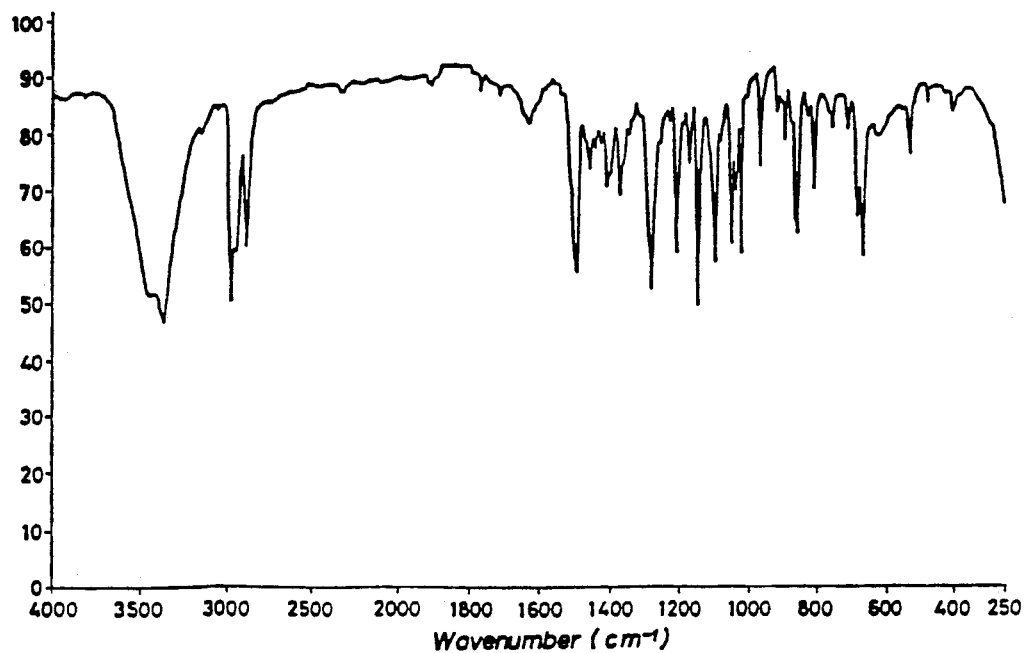
Figure 30:
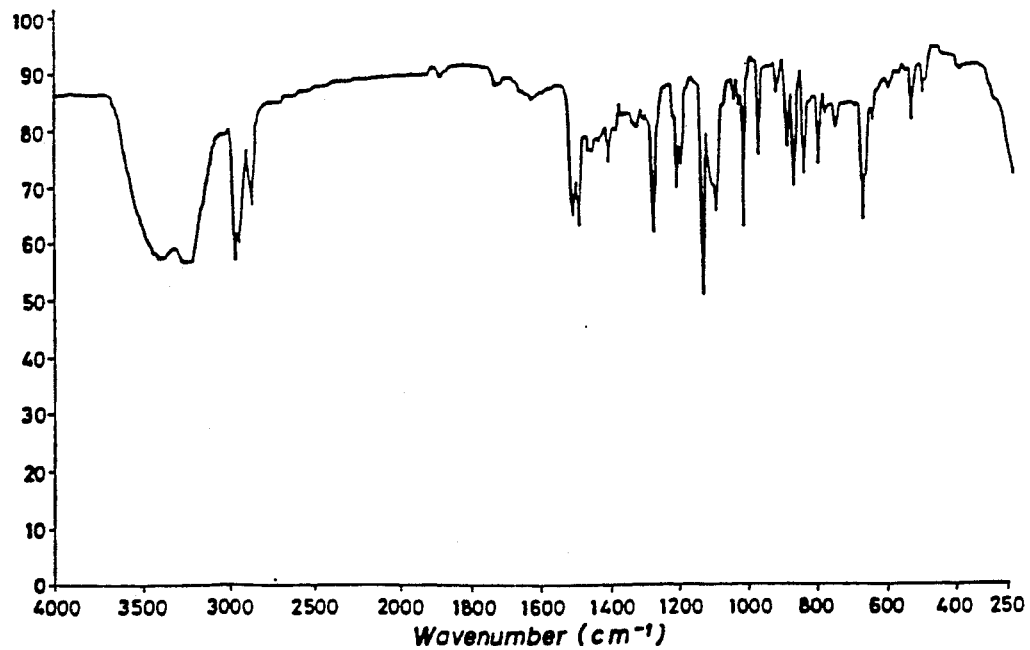
Figure 31:
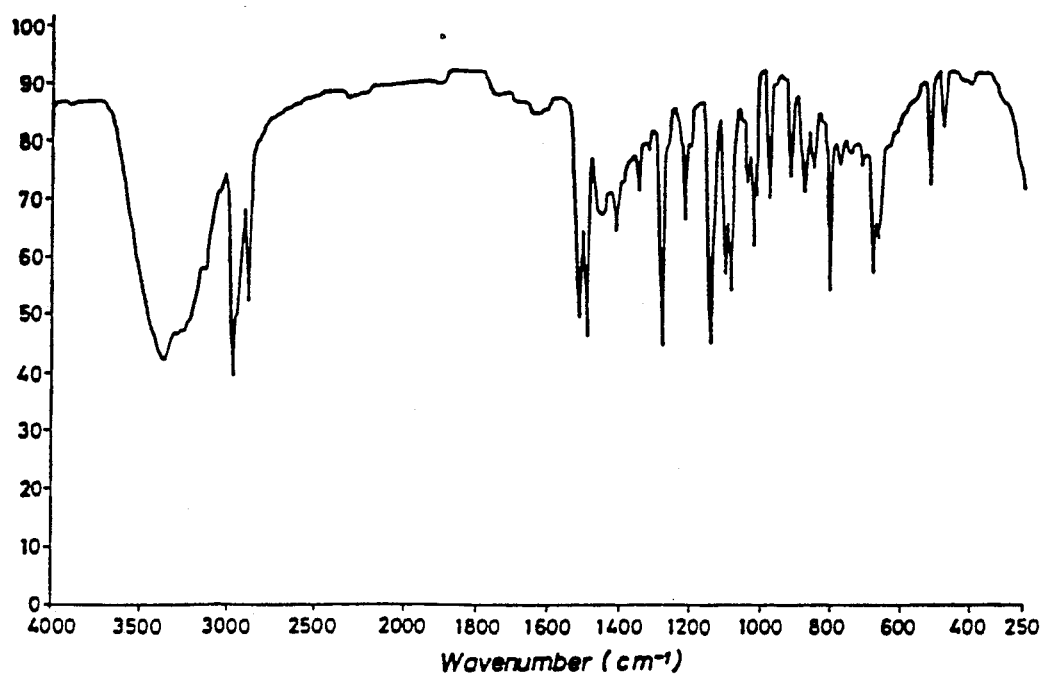
Figure 32:
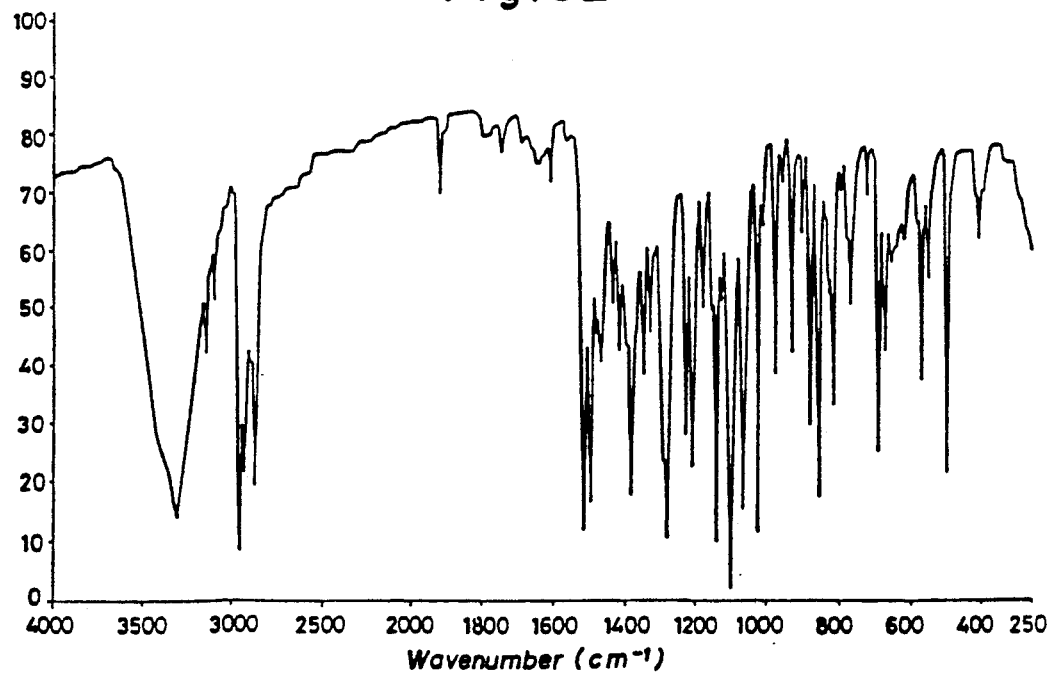
Figure 33:
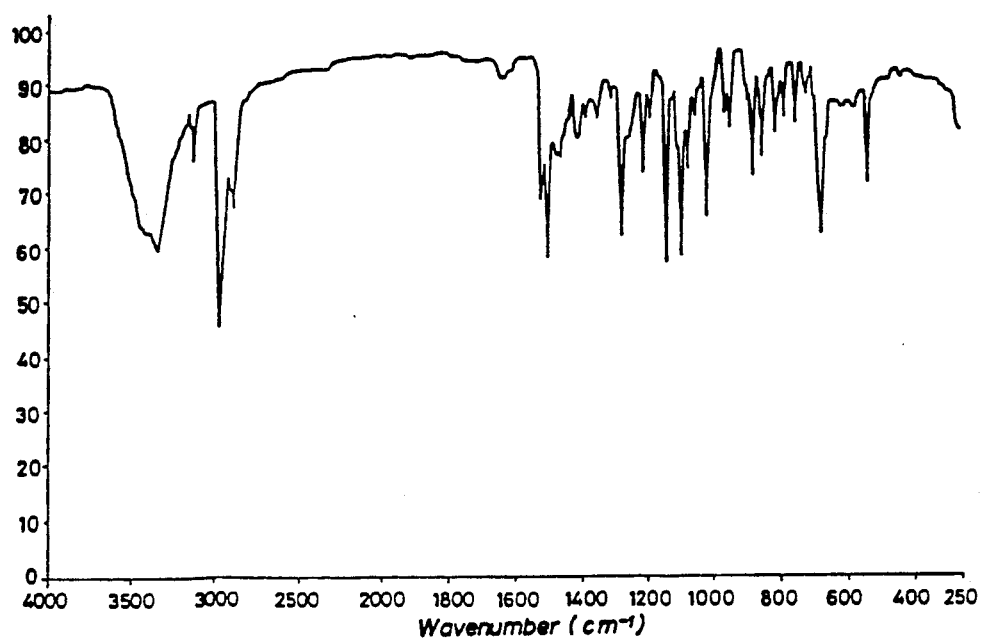
Figure 34:
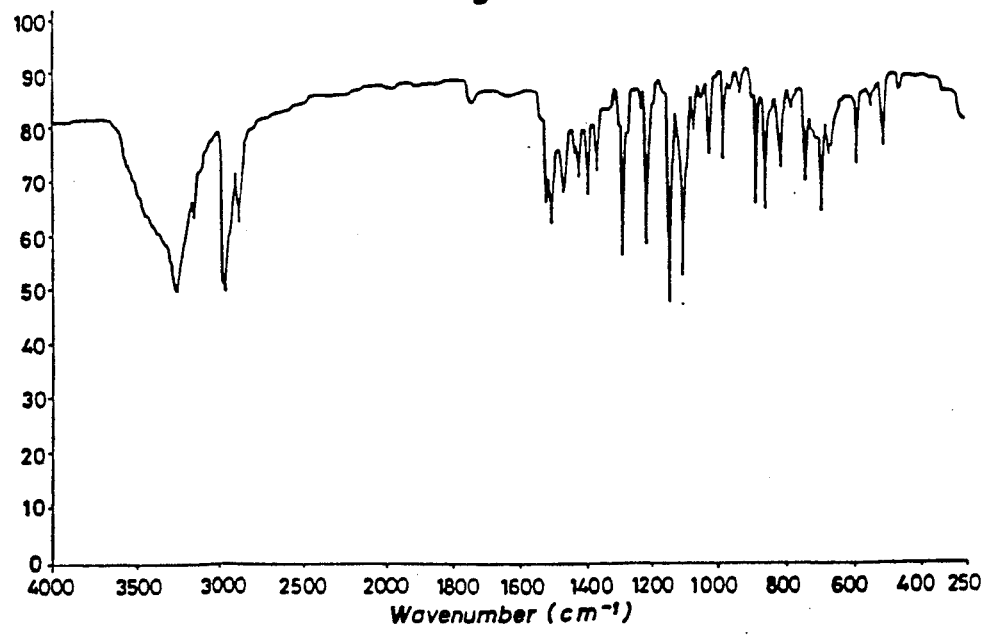
Figure 35:
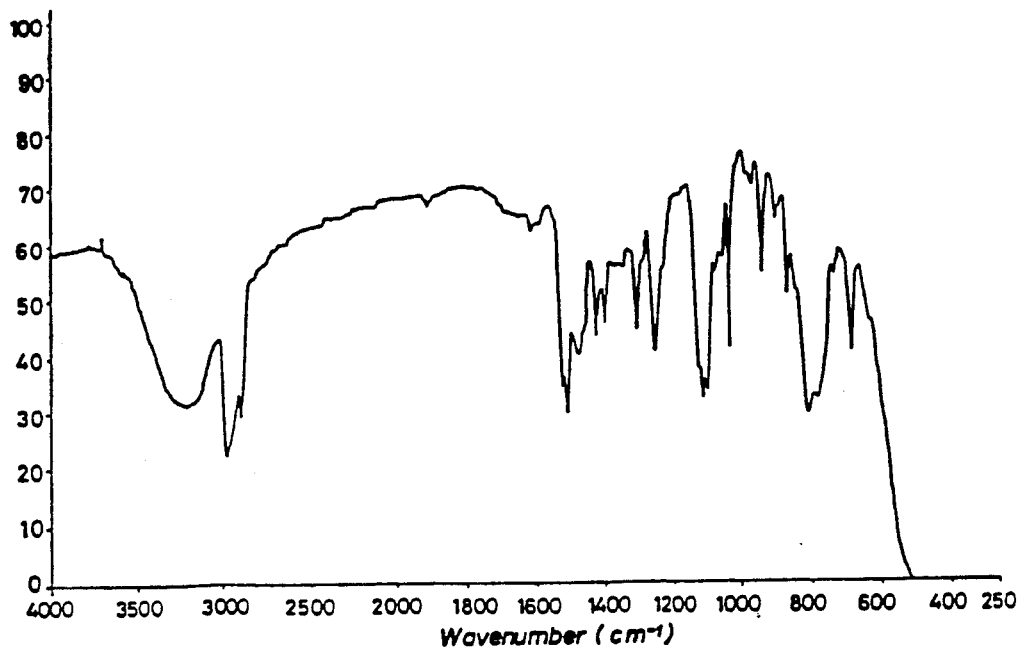
Figure 36:
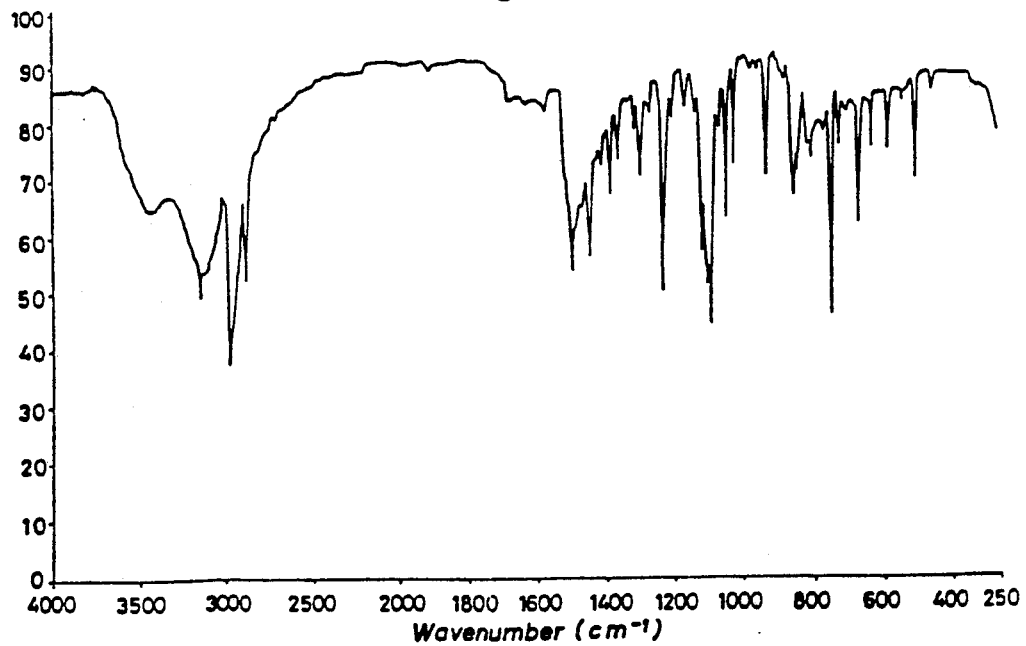
Figure 37:
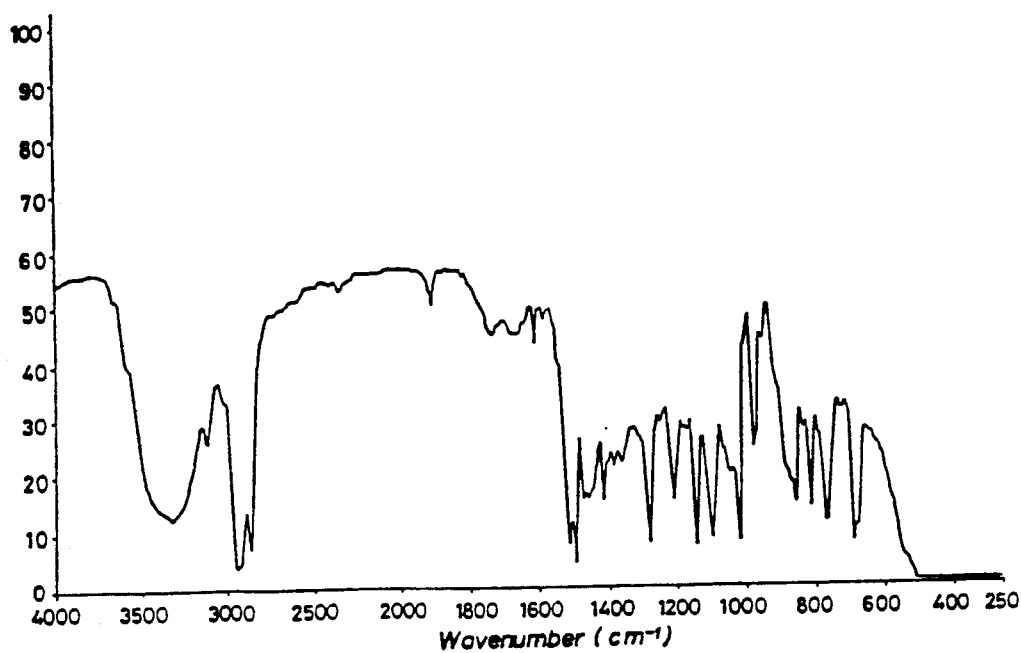
Figure 38:
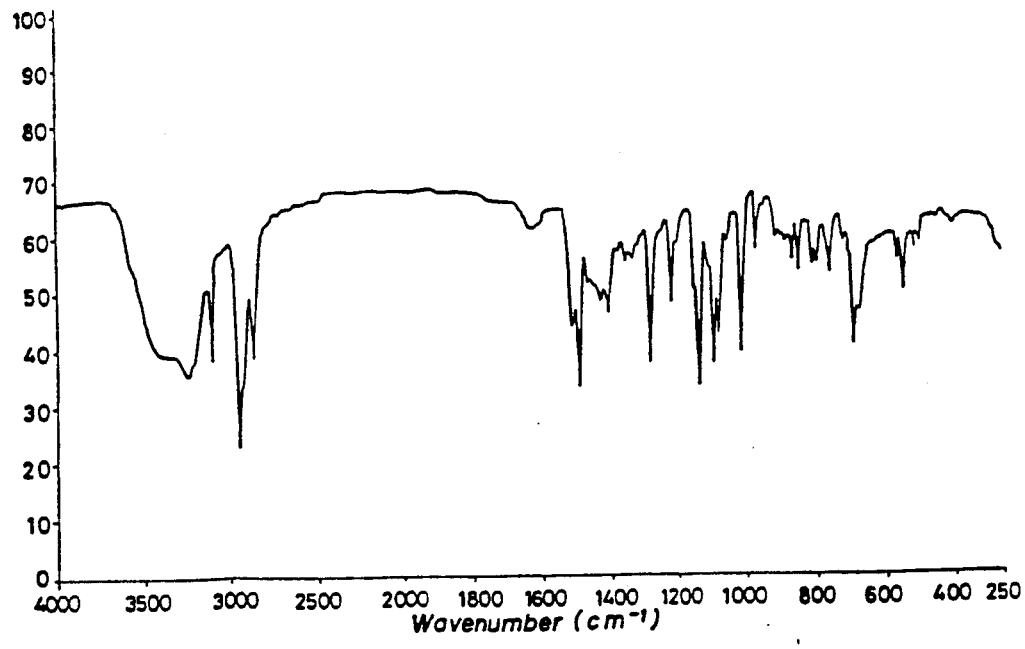
Figure 39:
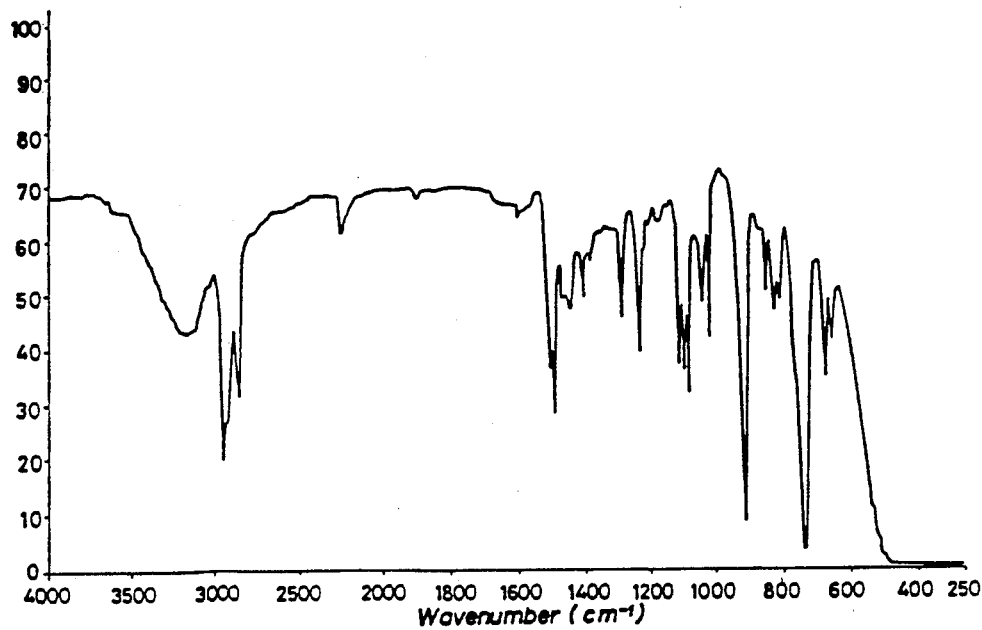
Figure 40:
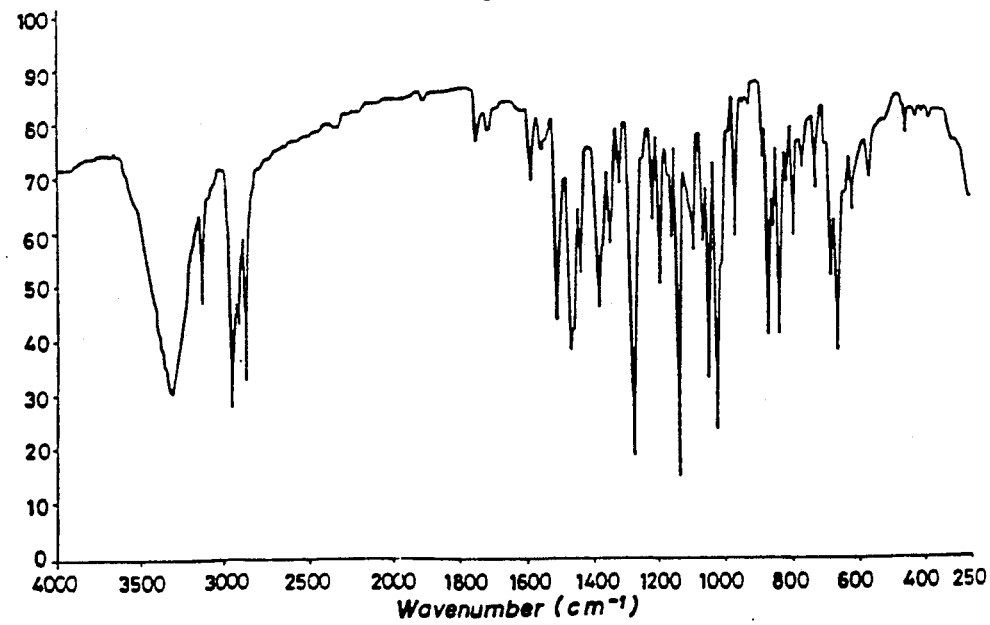
Figure 41:
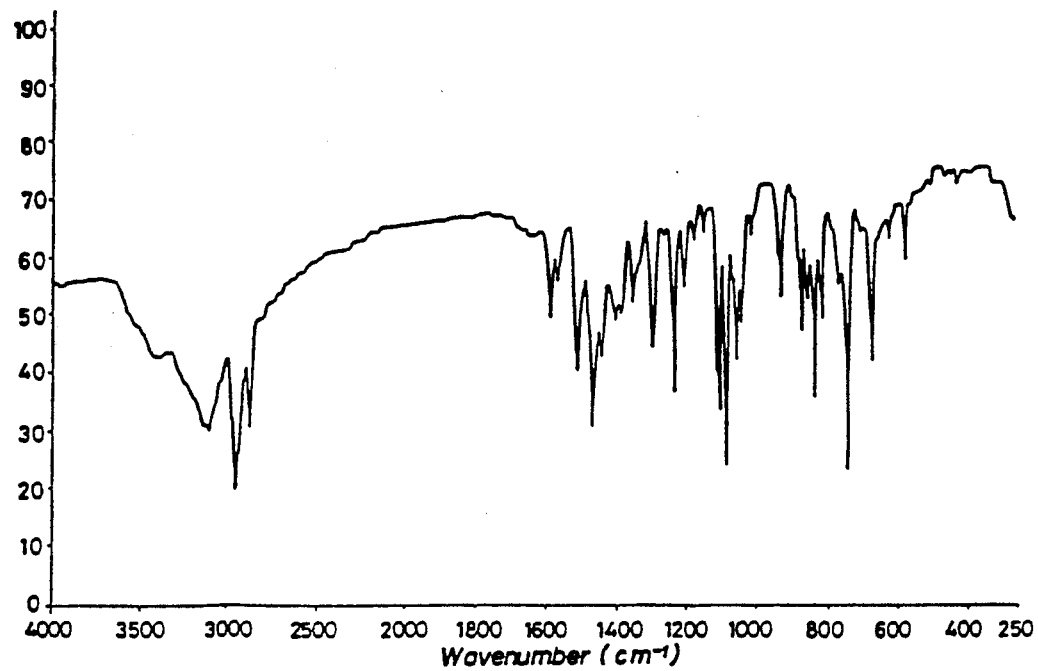
Figure 42:
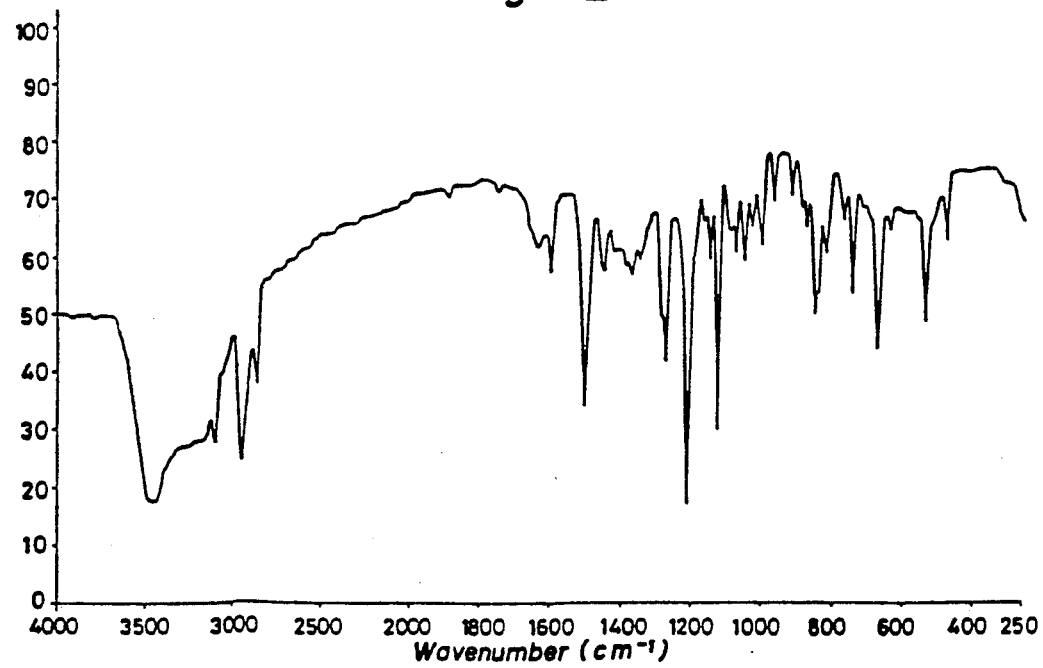
Figure 43:
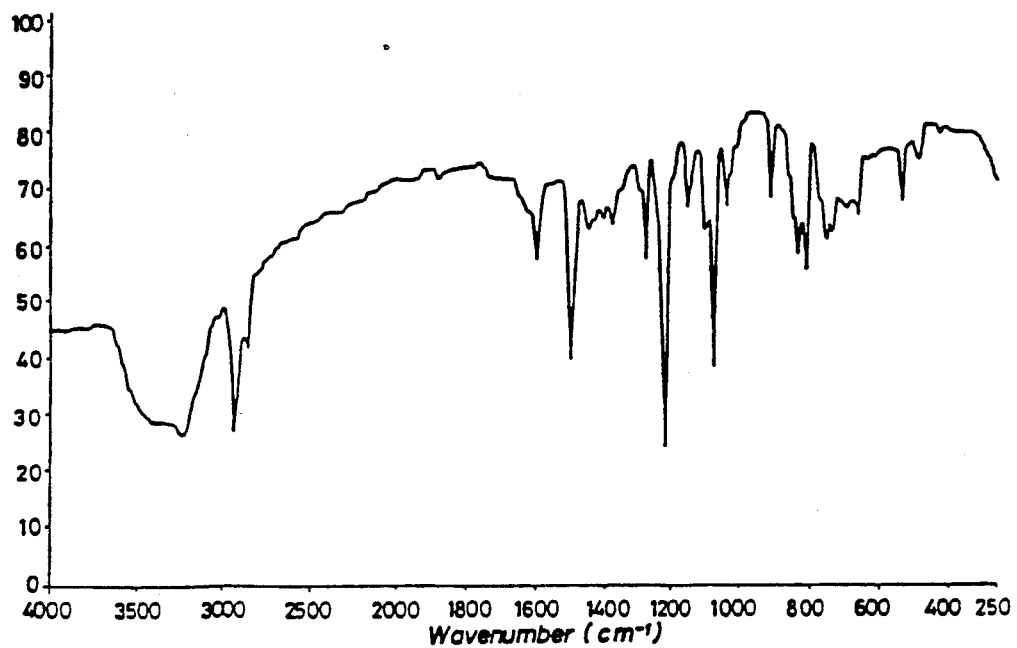
Figure 44:
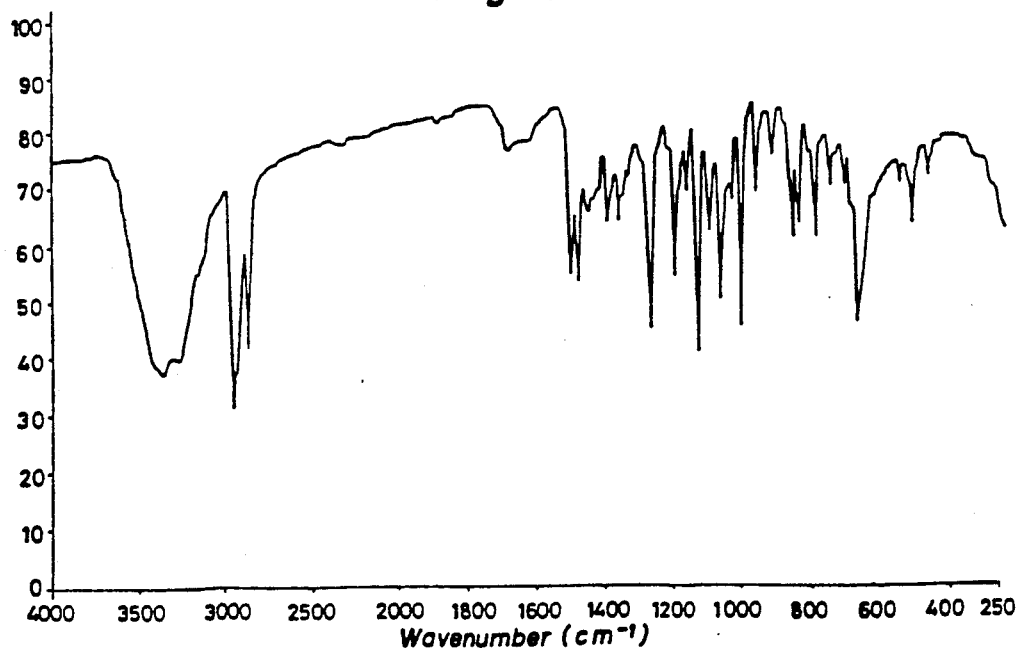
Figure 45:
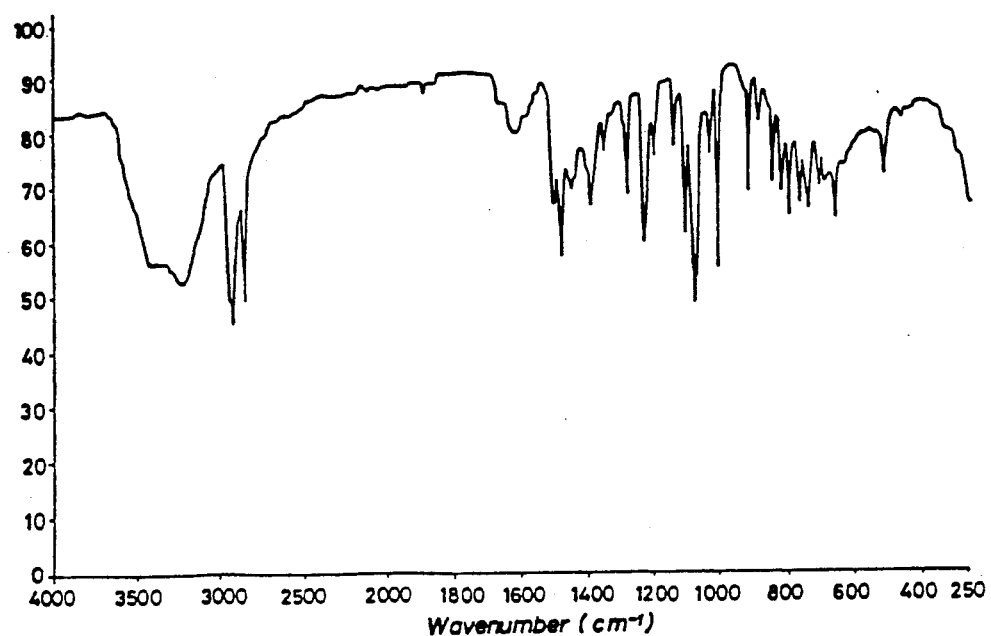
Figure 46:
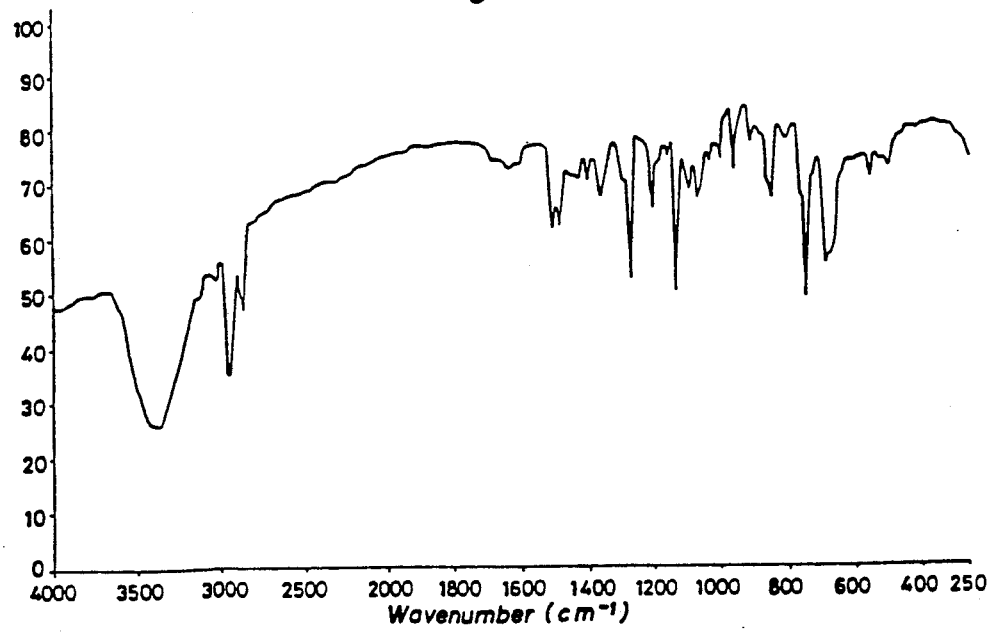
Figure 47:
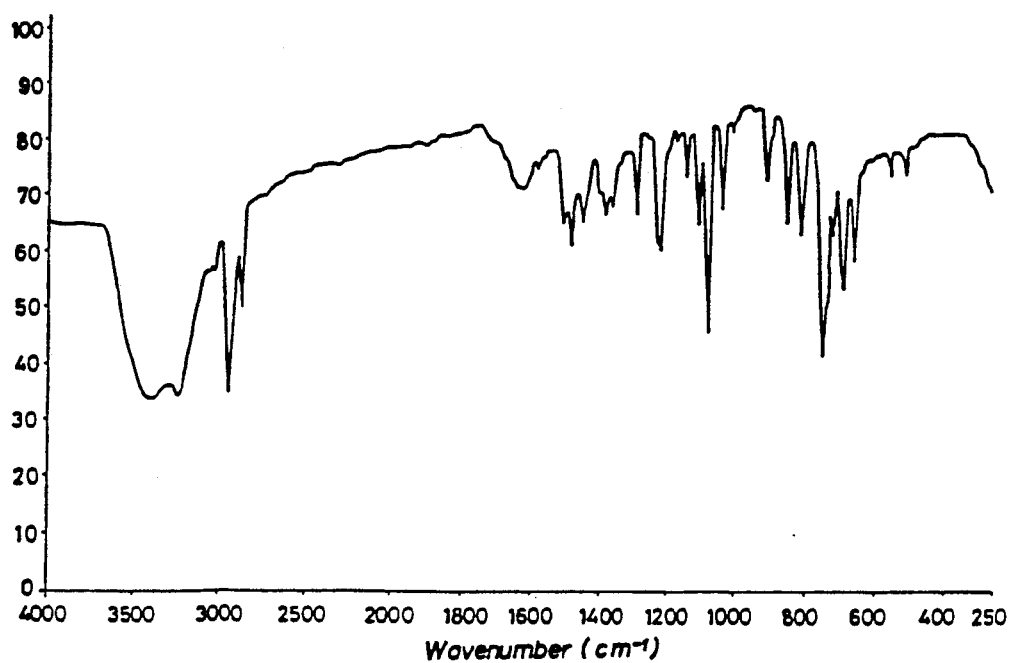
Figure 48:
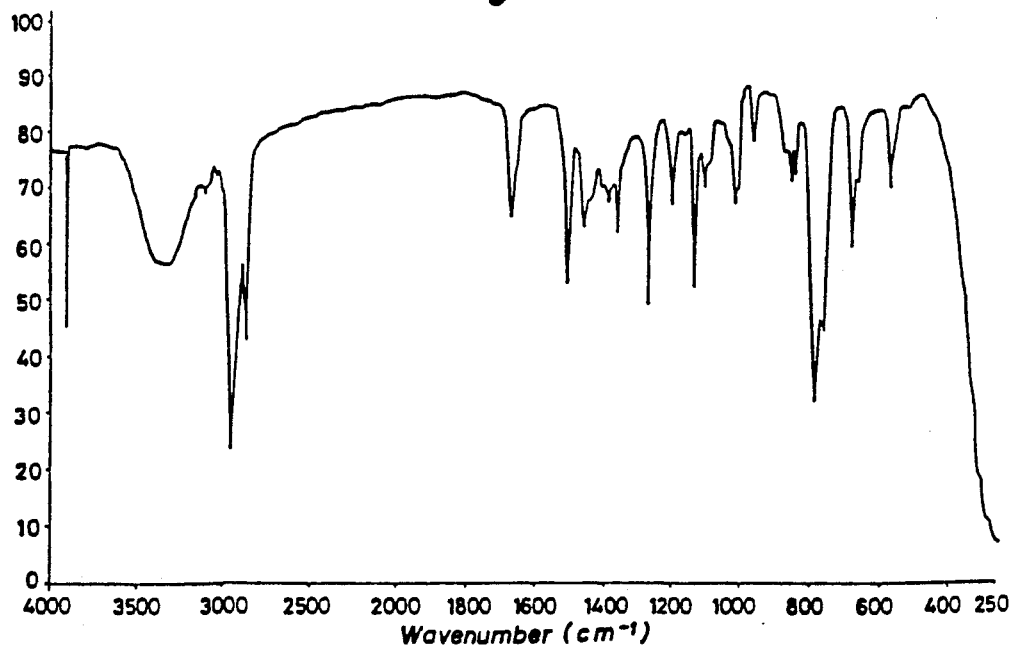
Figure 49:
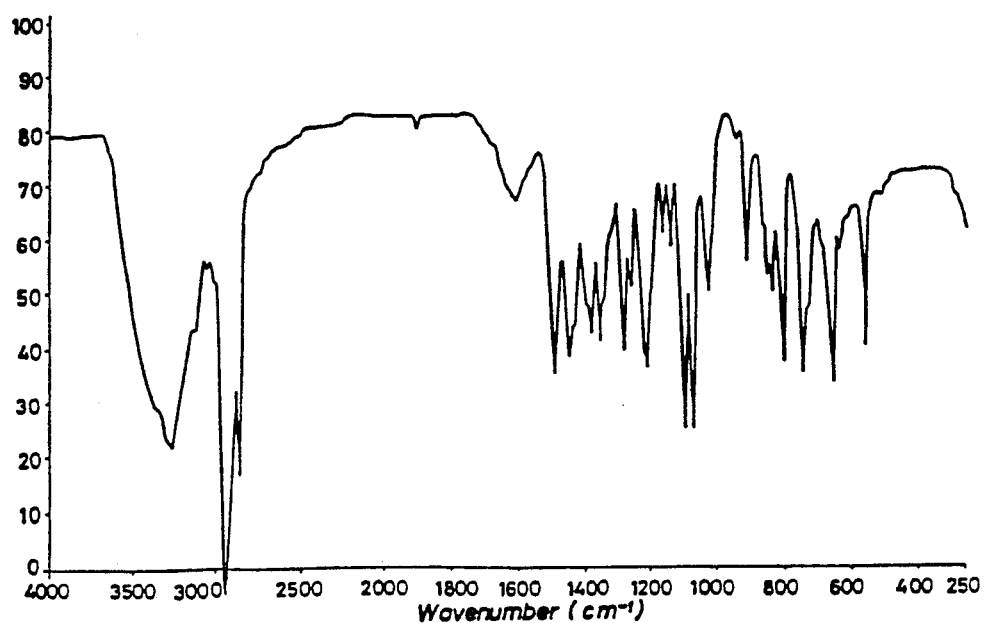
Figure 50:
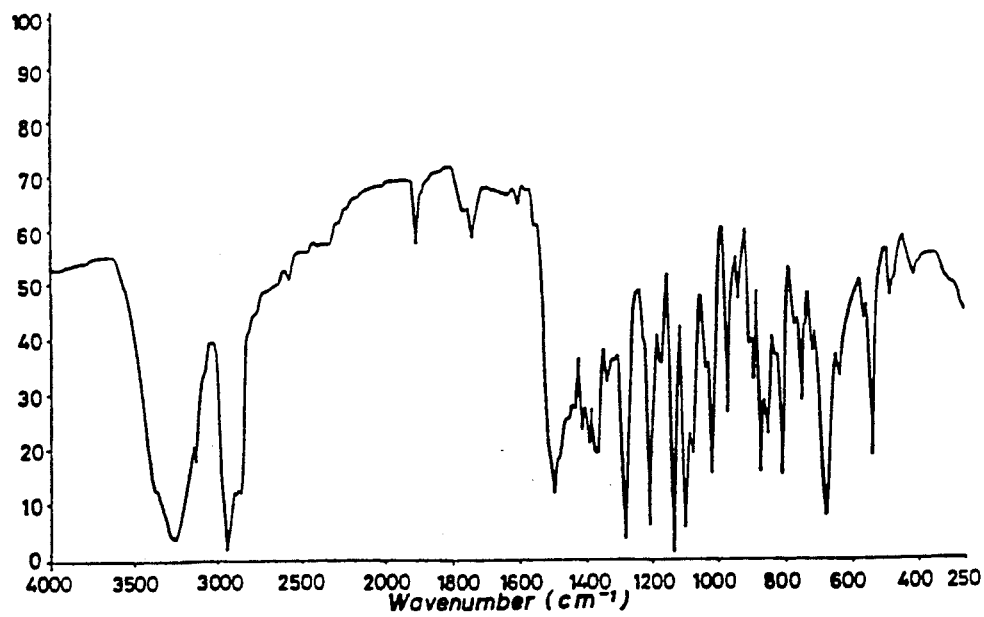
Figure 51:
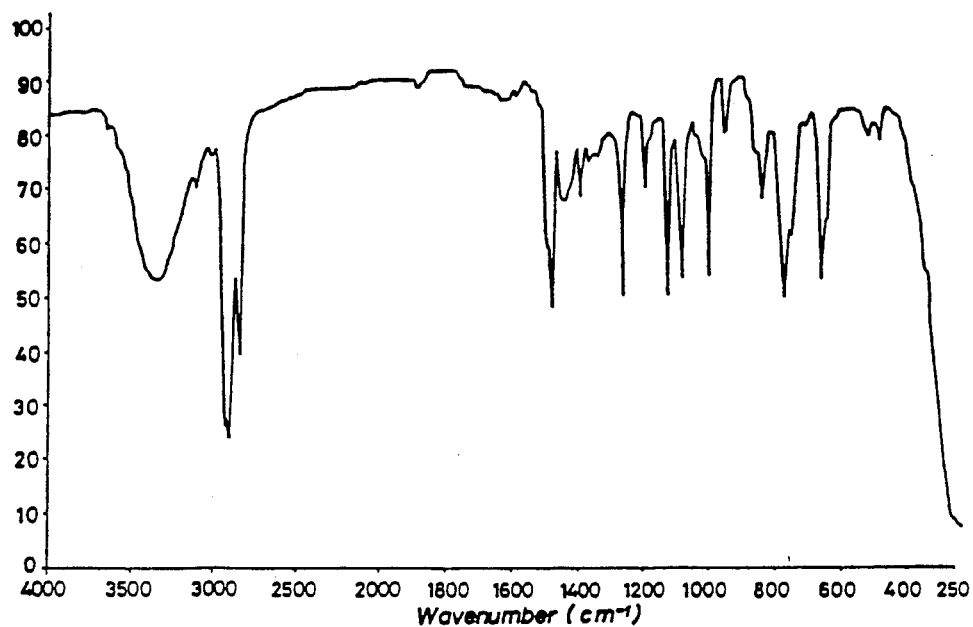
Figure 52:
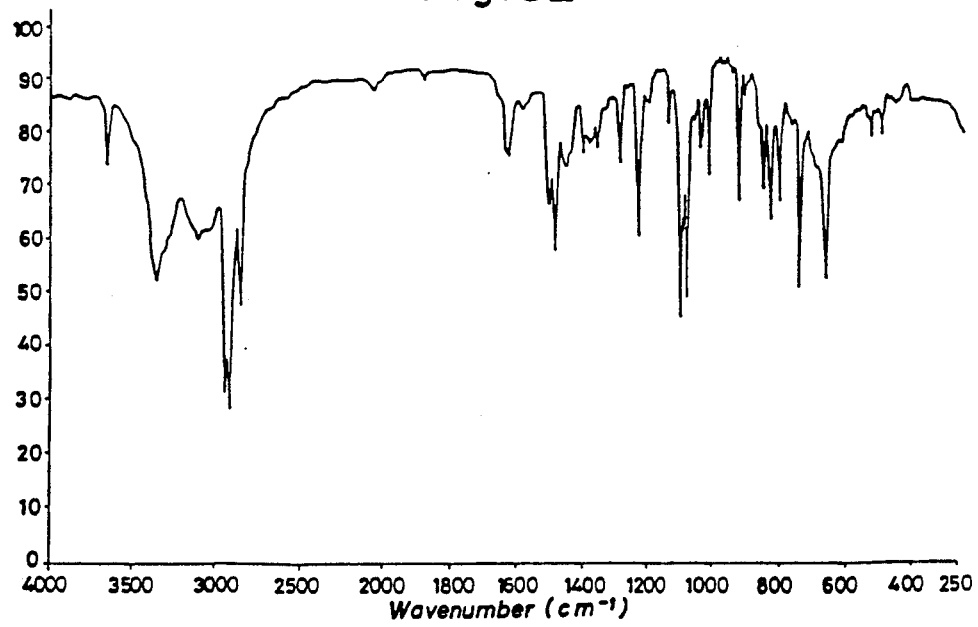
Figure 53:
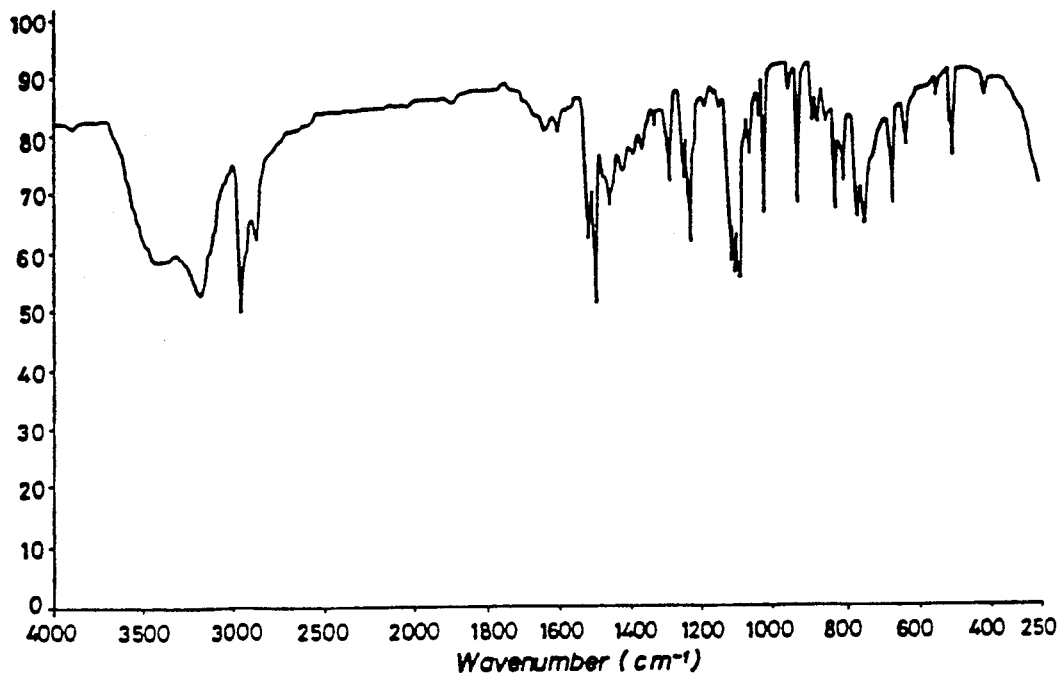
Figure 54:
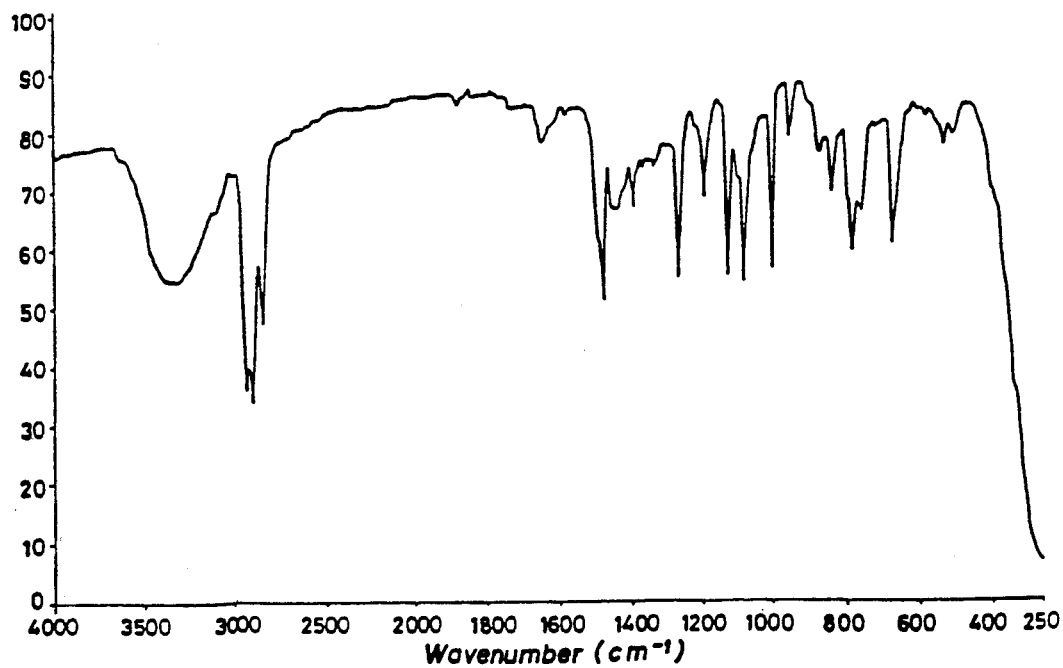
Figure 55:
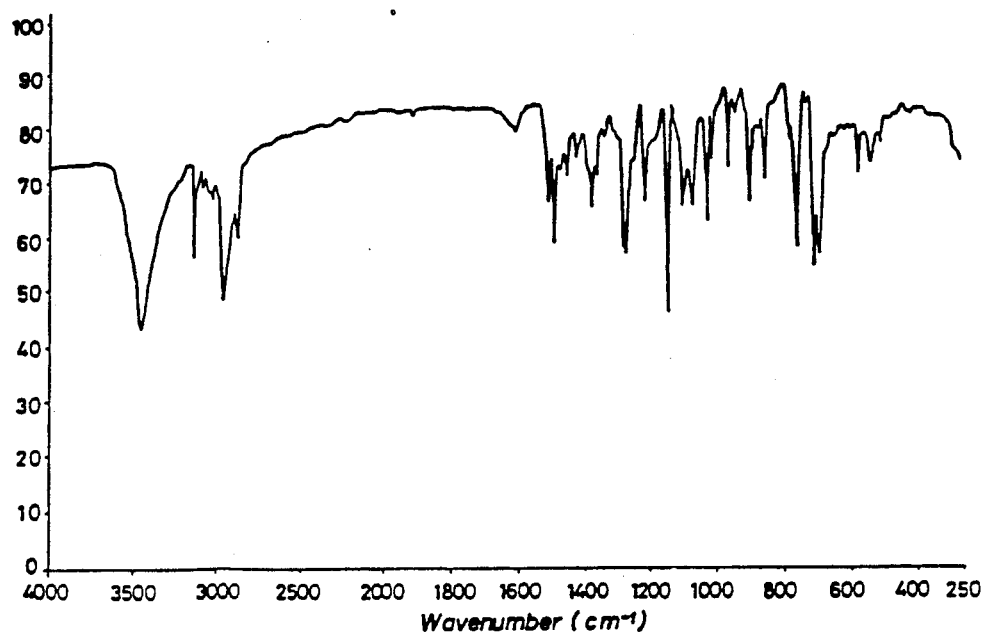
Figure 56:
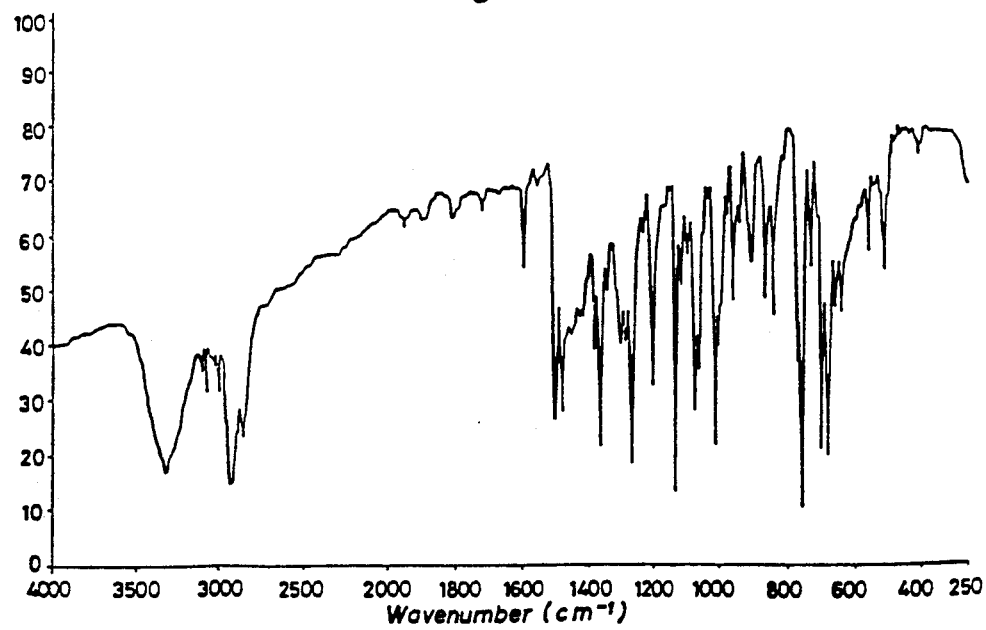
Figure 57:
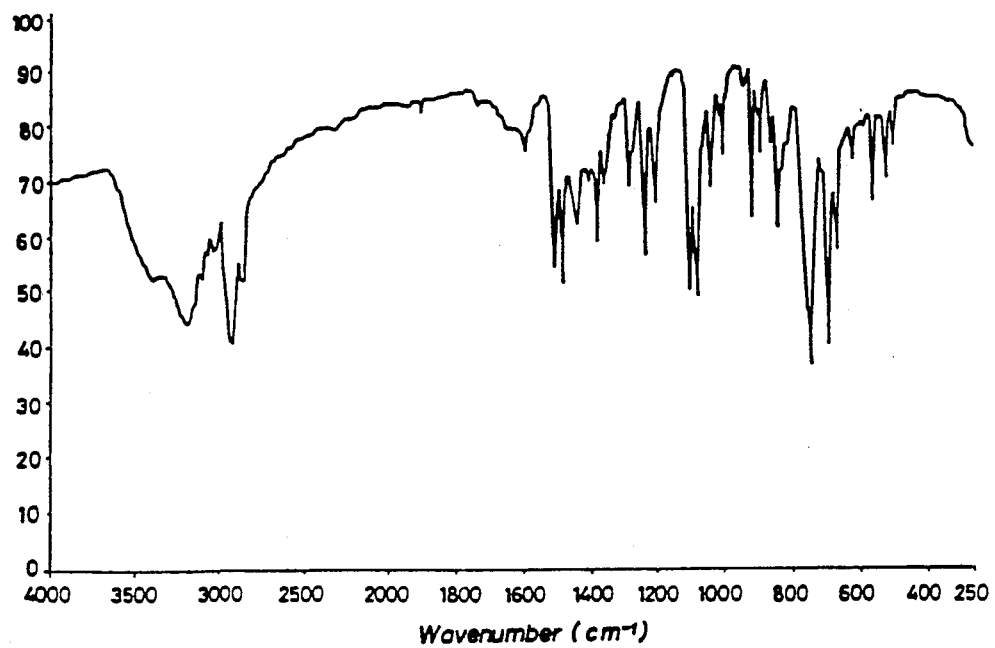
Figure 58:
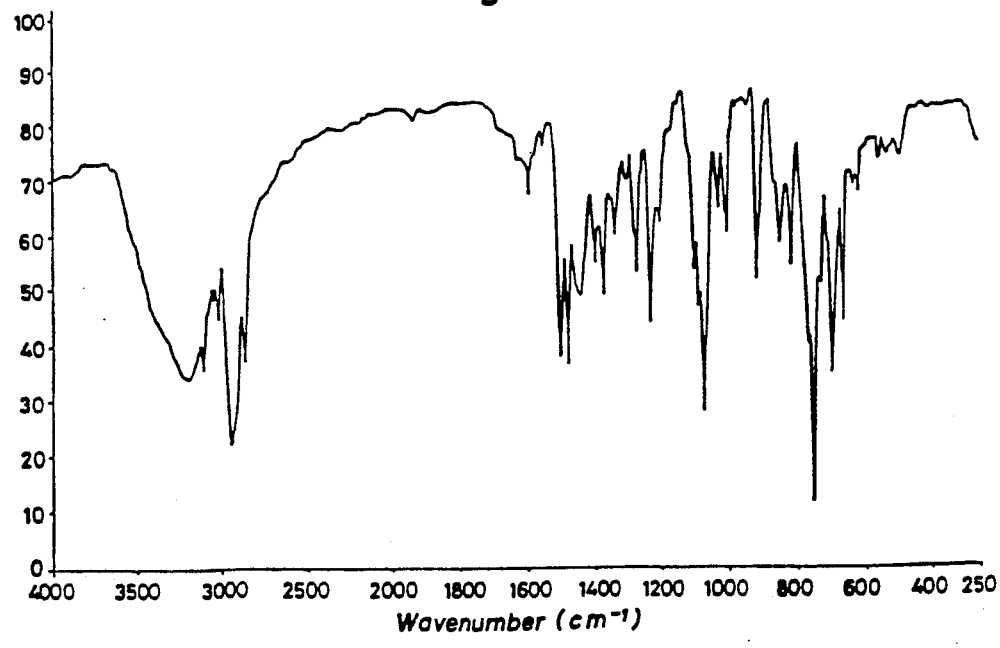
Figure 59:
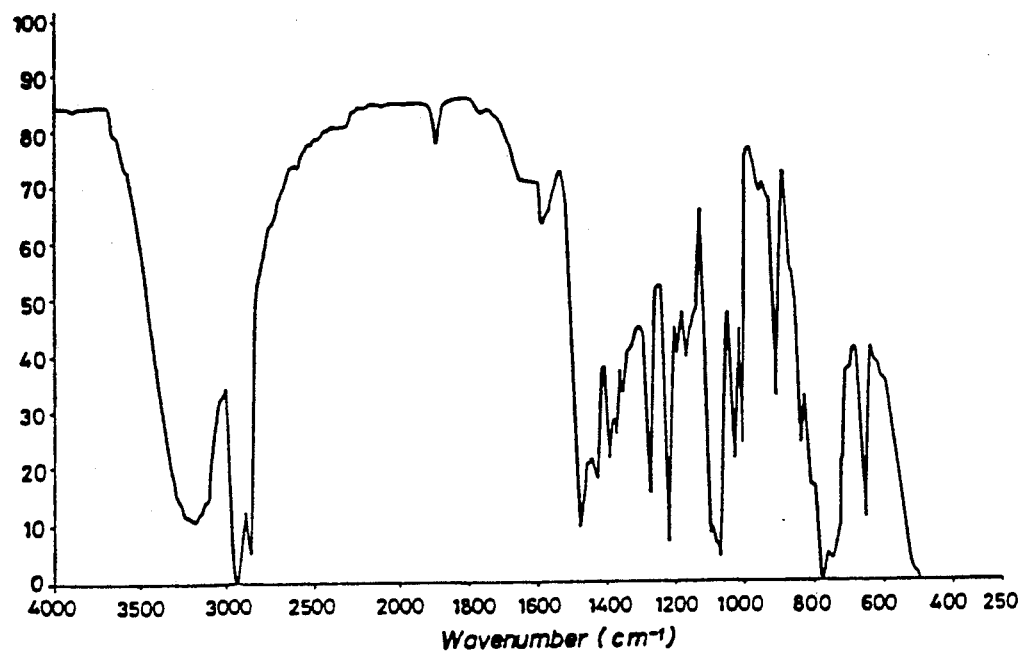
Figure 60:
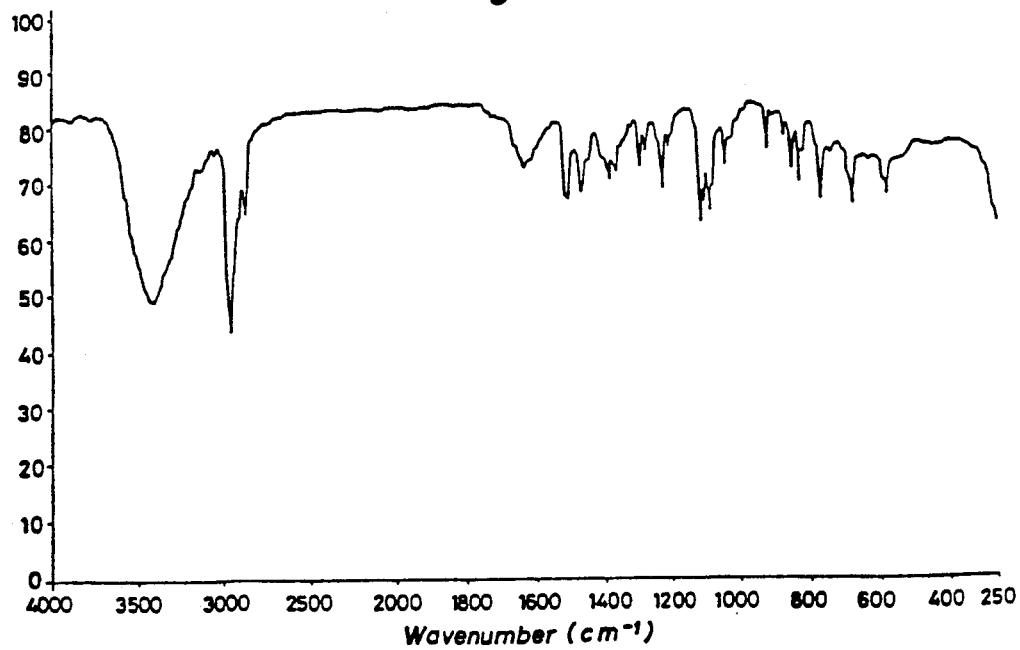
Figure 61:
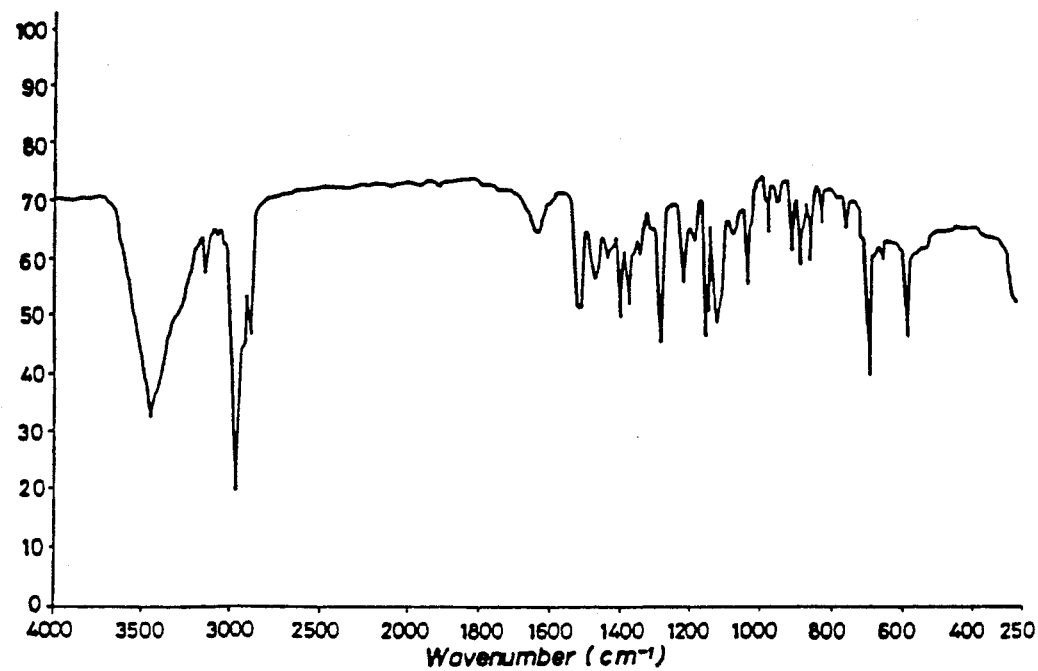
Figure 62:
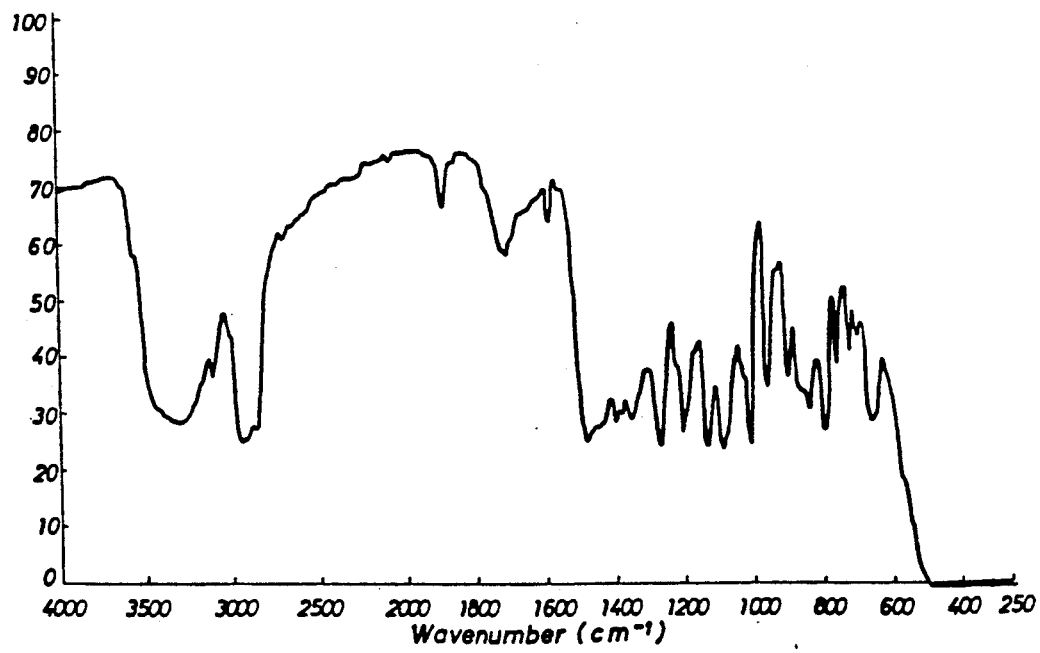
Figure 63:
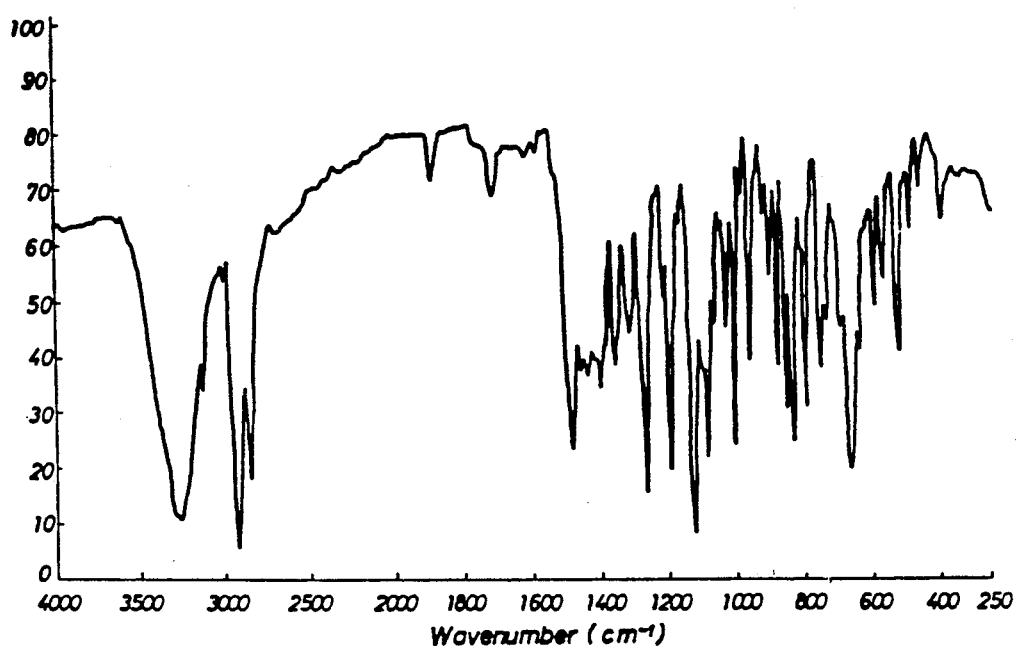
Figure 64:
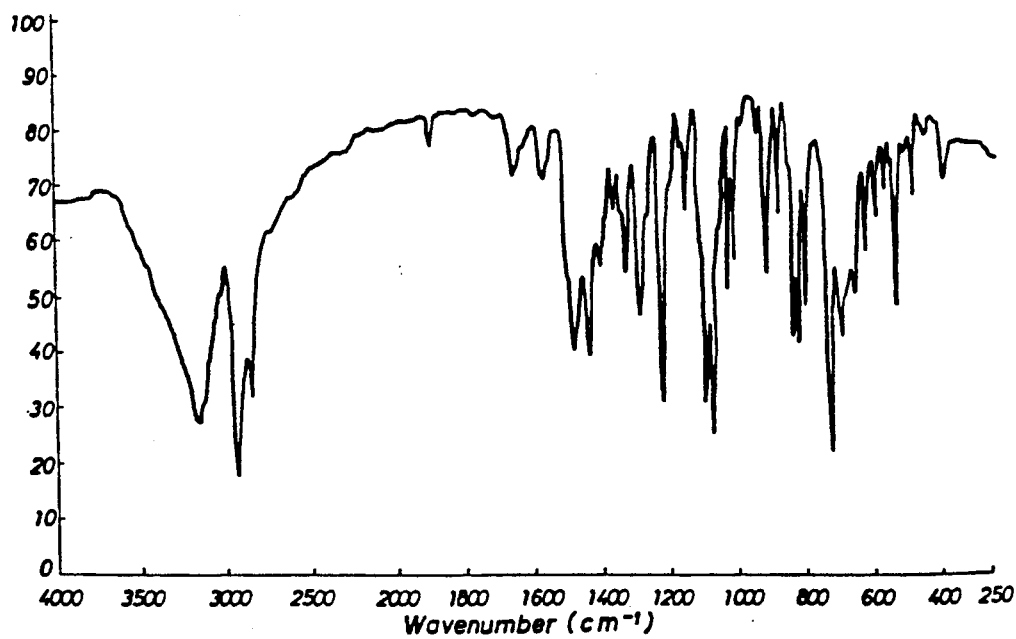
Figure 65:
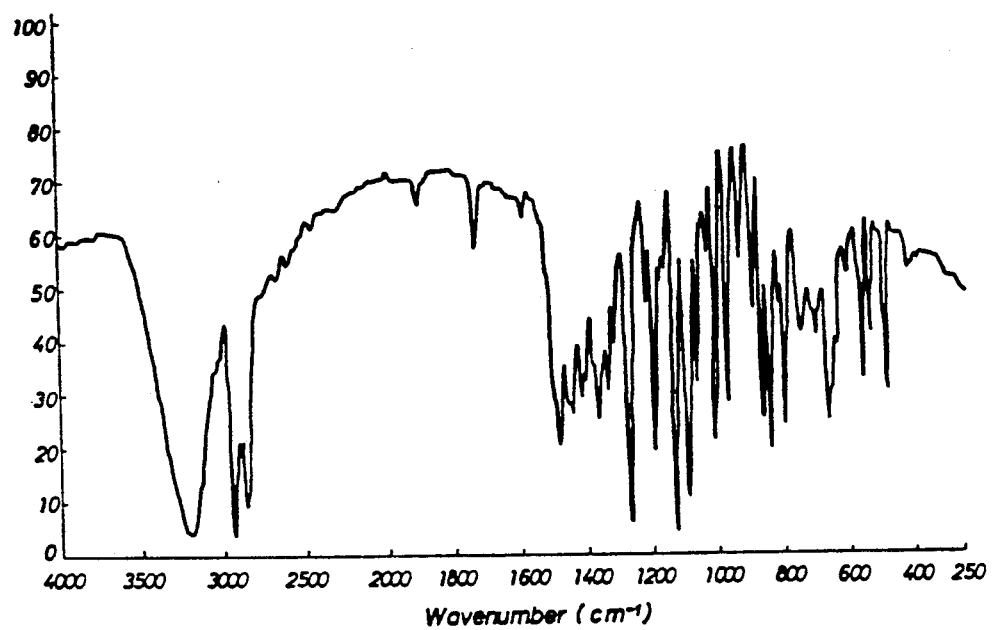
Figure 66:
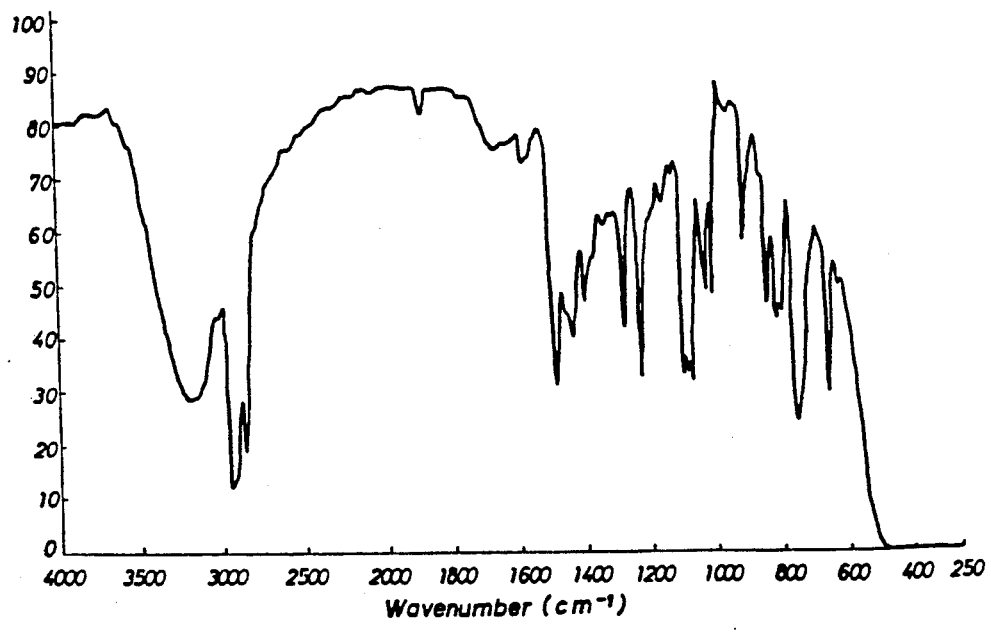
Figure 67:
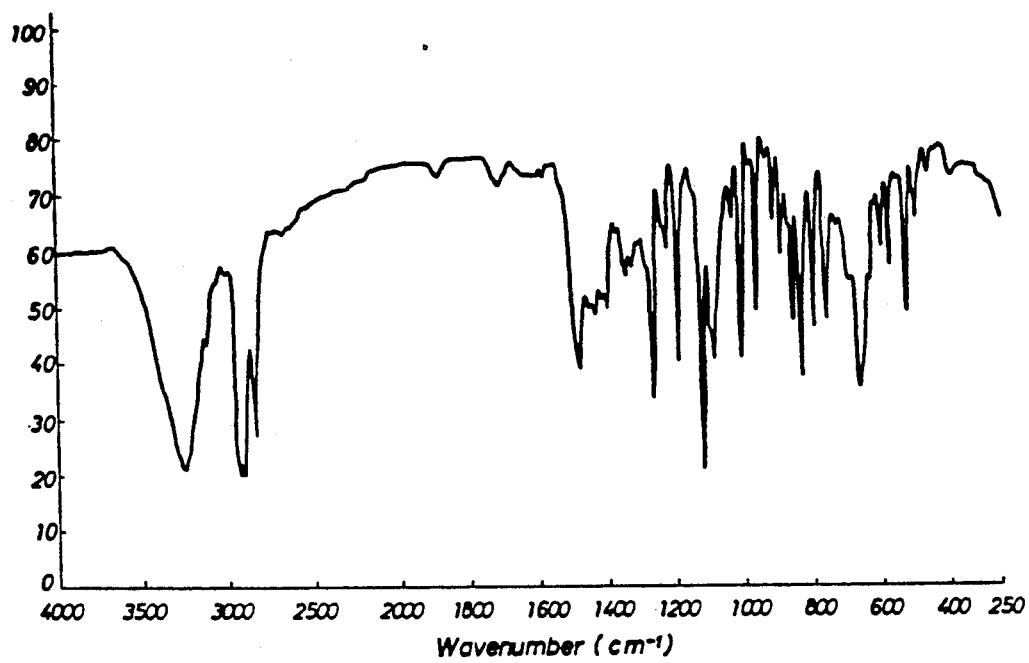
Figure 68:
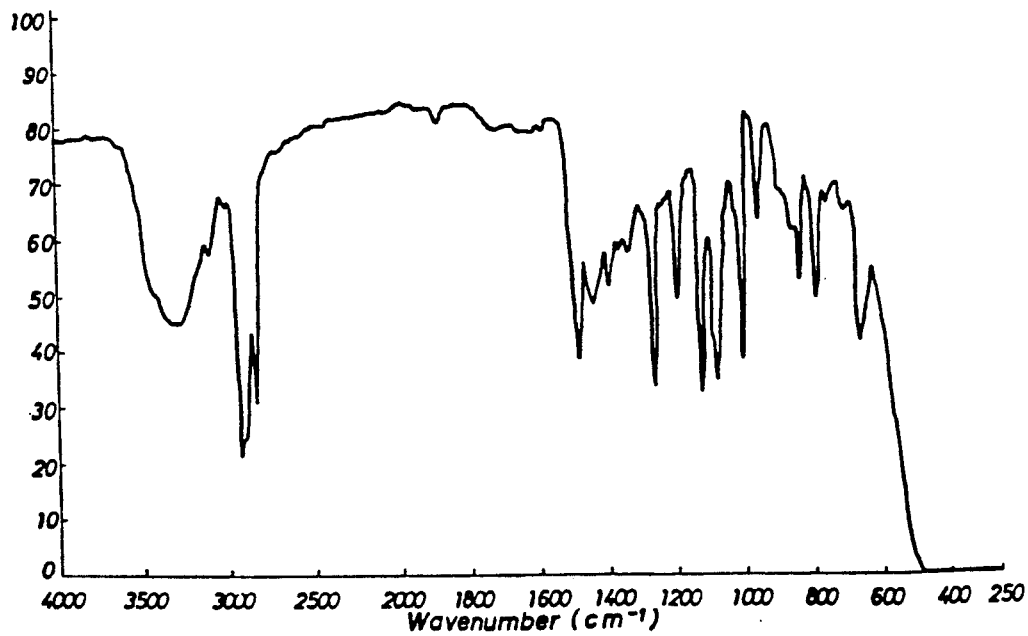
Figure 69:
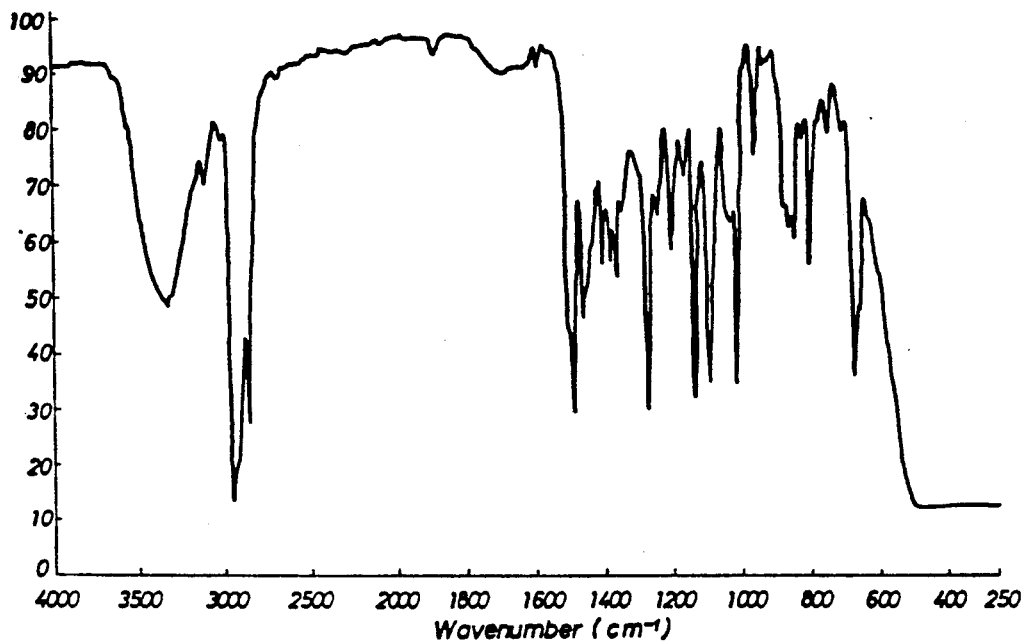
Figure 70:
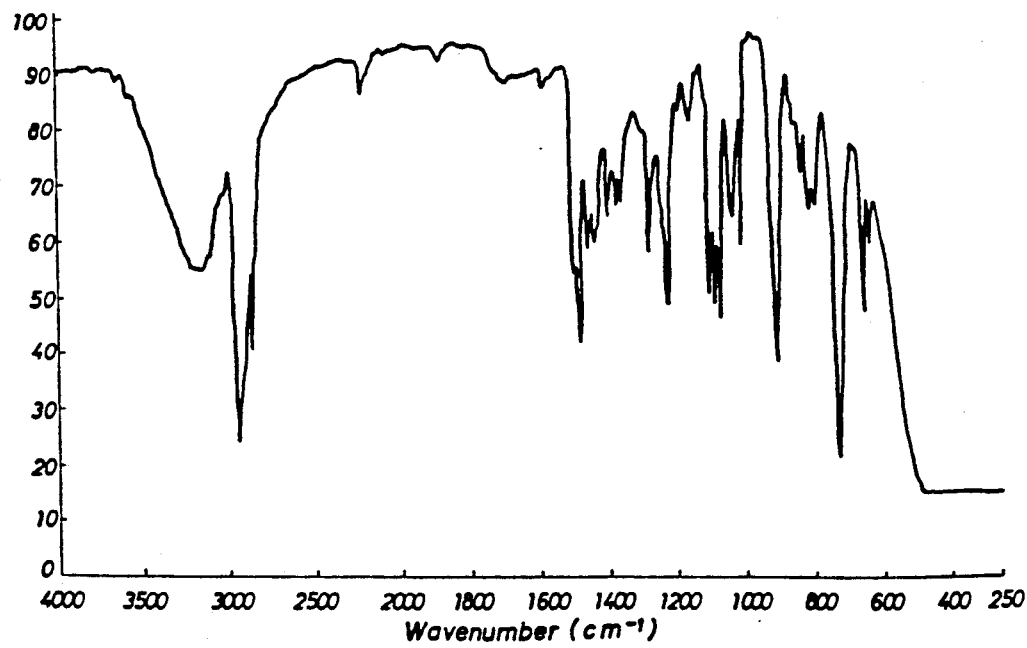
Figure 71:
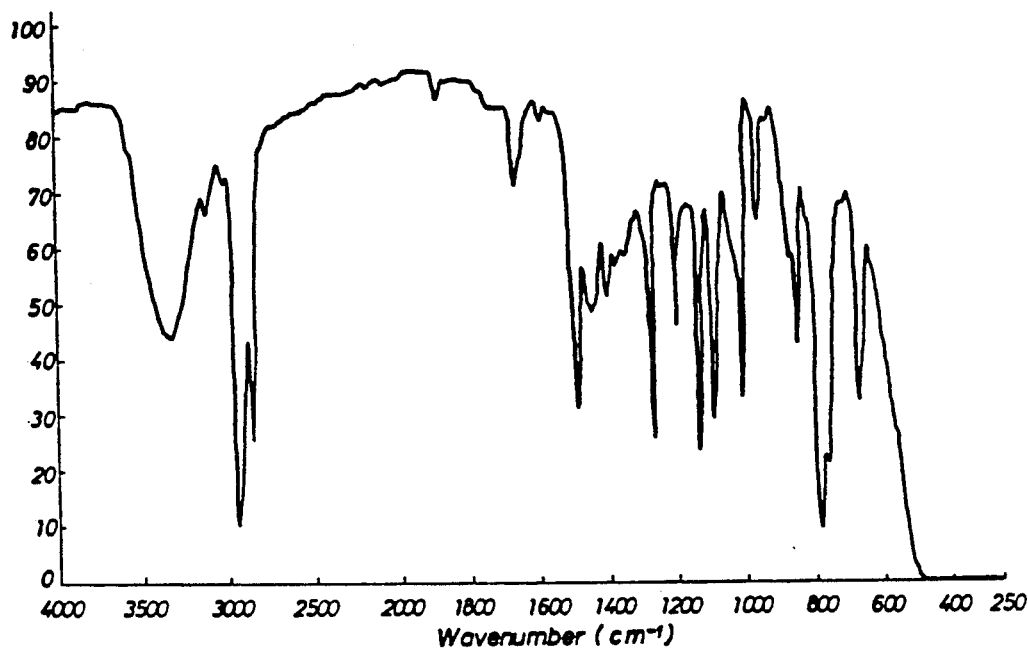
Figure 72:
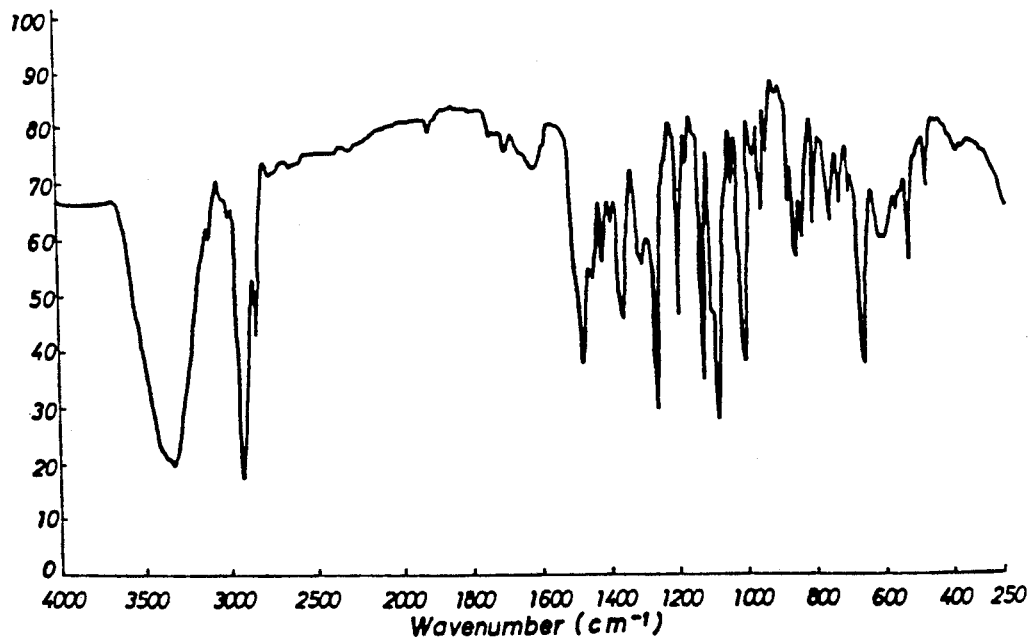
Figure 73:
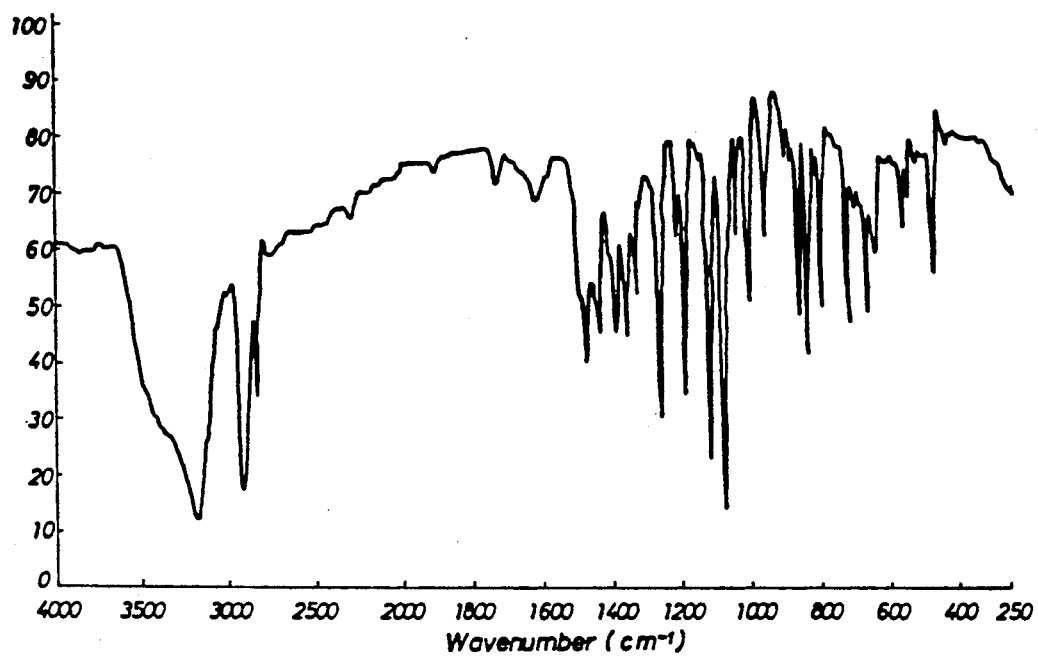
Figure 74:
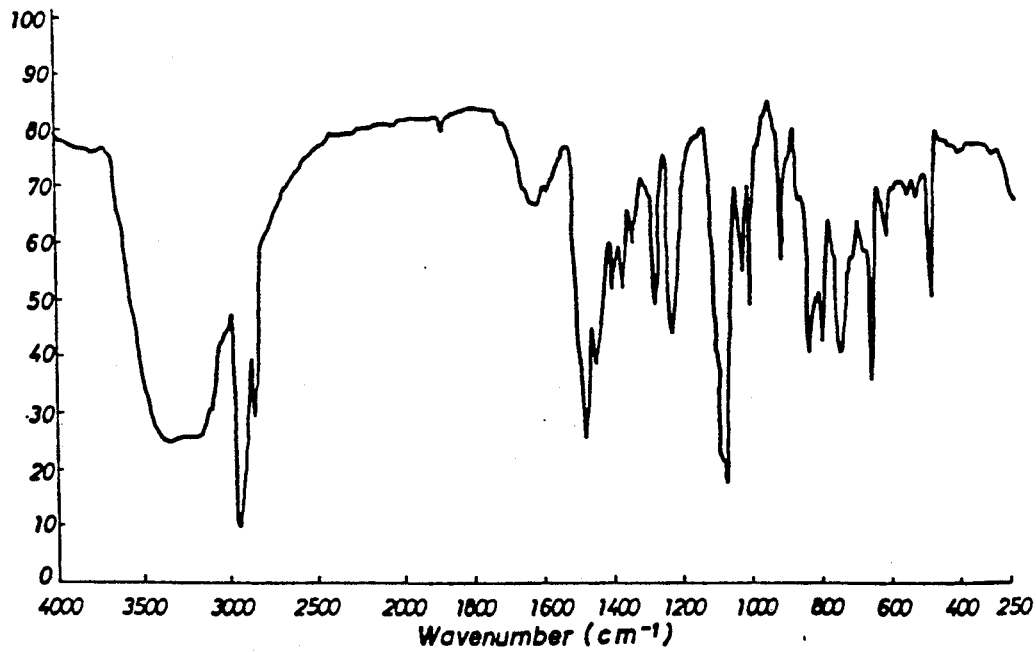
Figure 75:
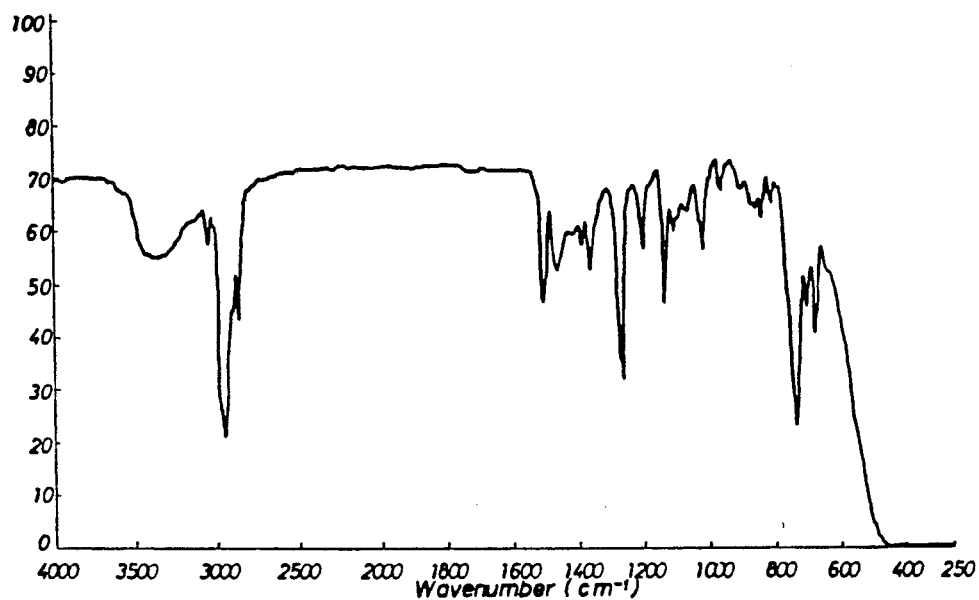
Figure 76:
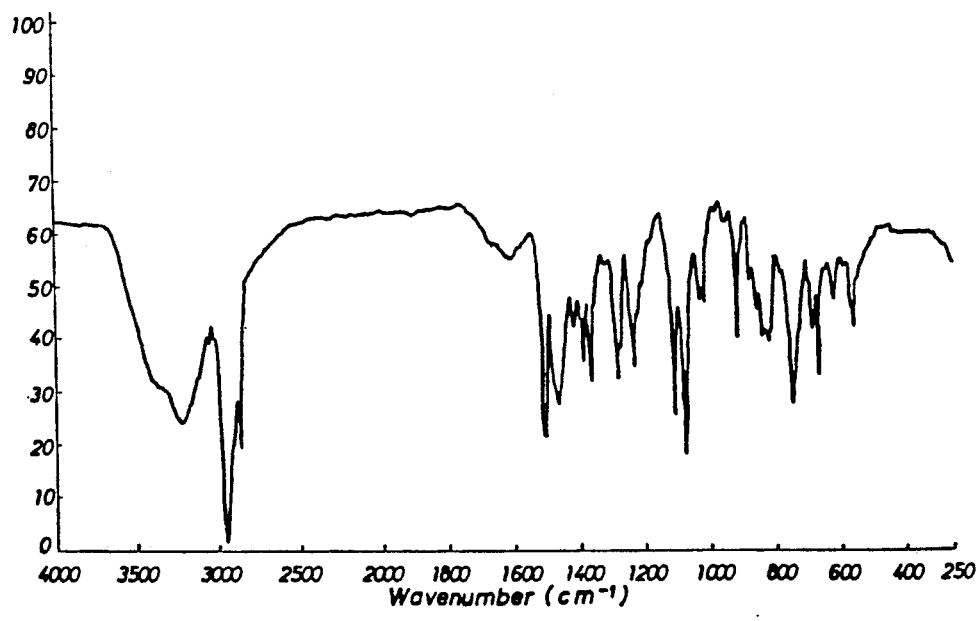
Figure 77:
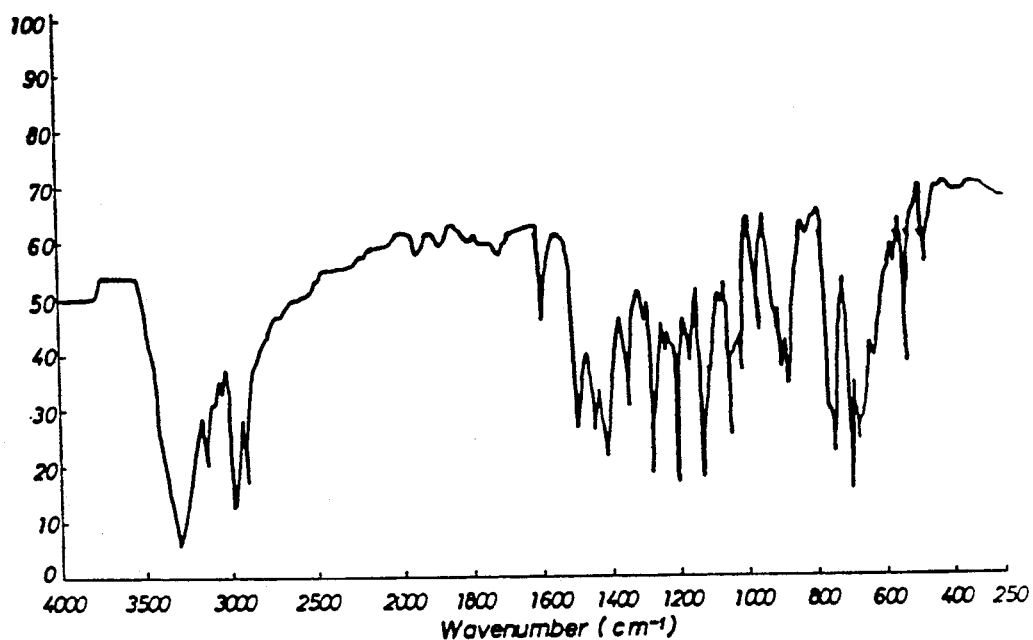
Figure 78:
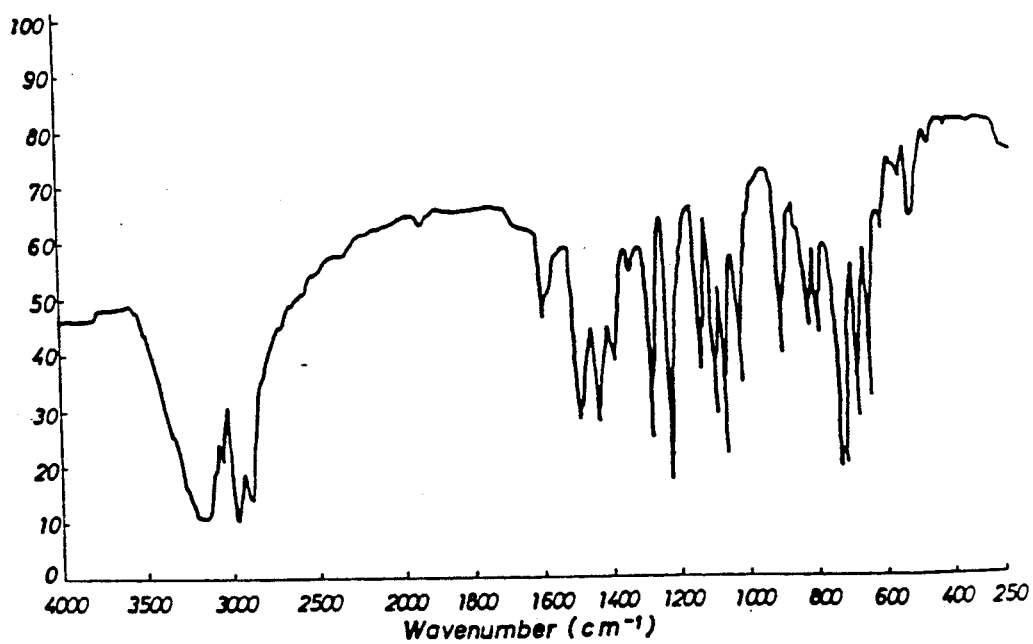
Figure 79:
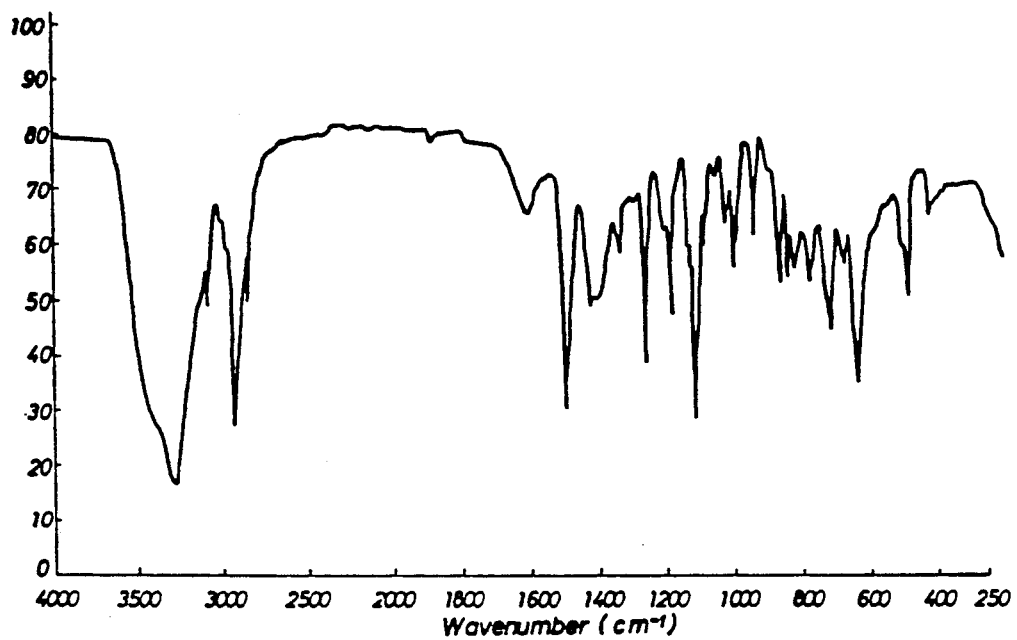
Figure 80:
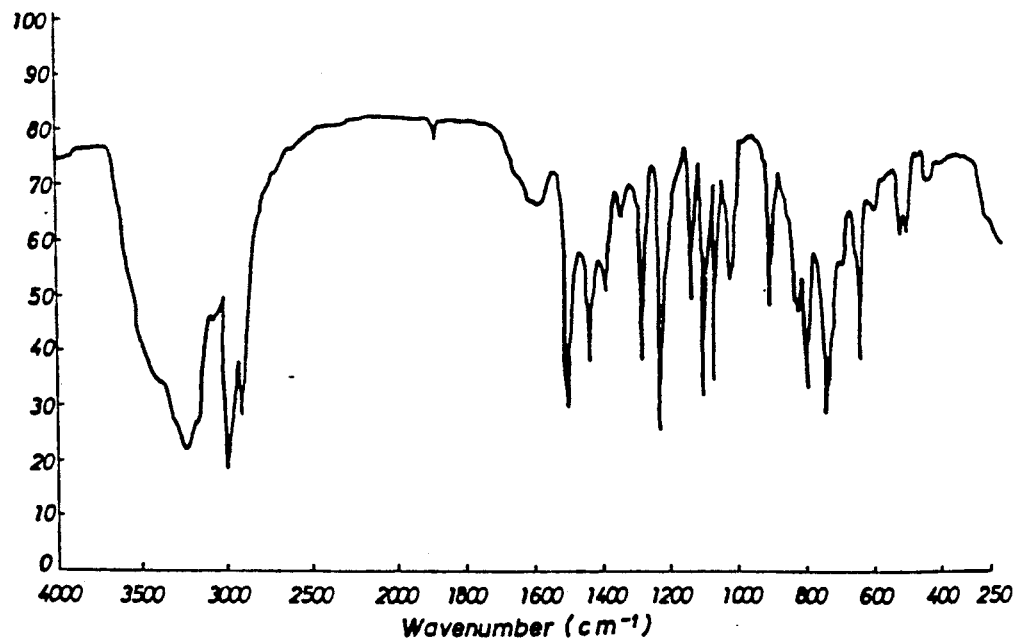
Figure 81:
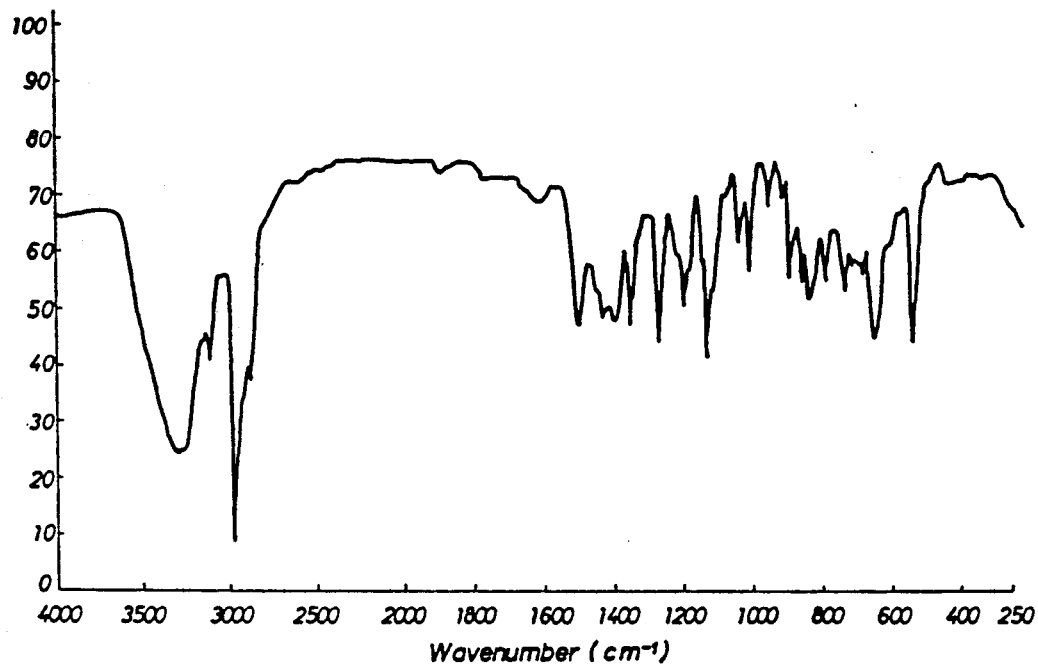
Figure 82:
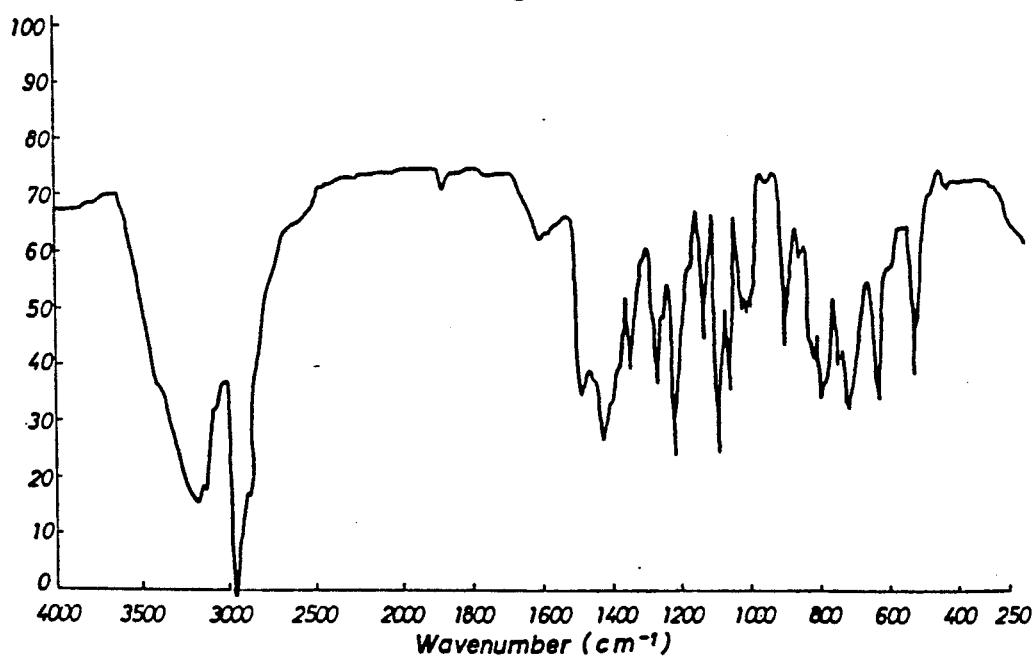
Figure 83:
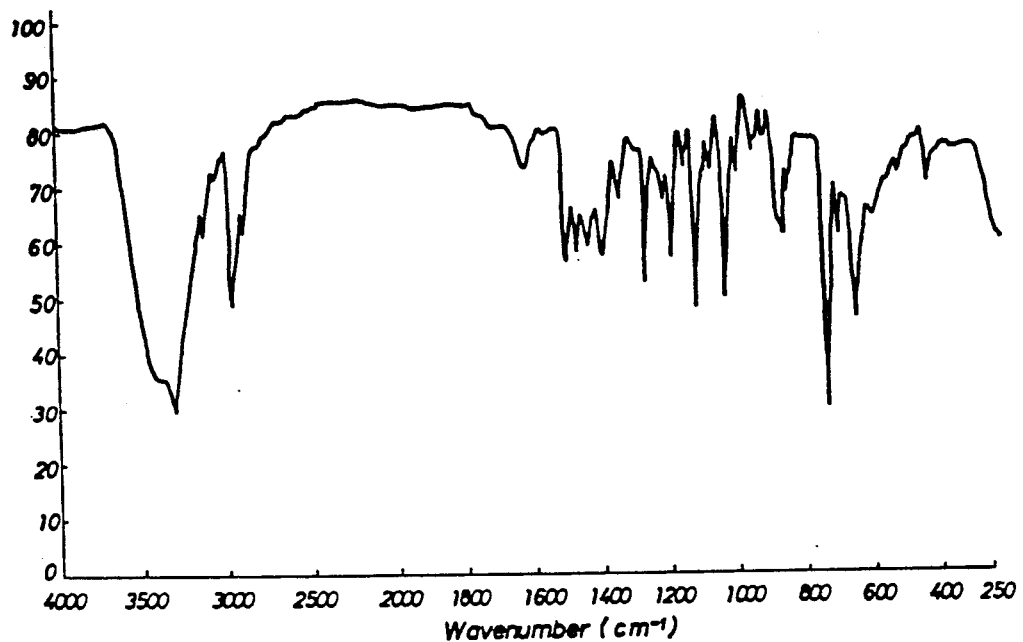
Figure 84:
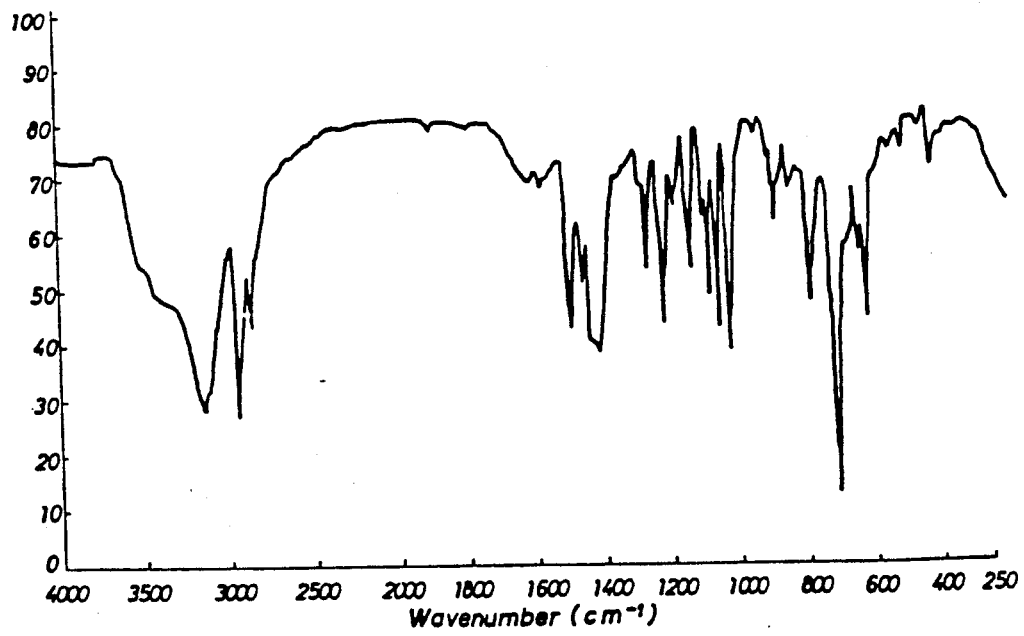
Figure 85:
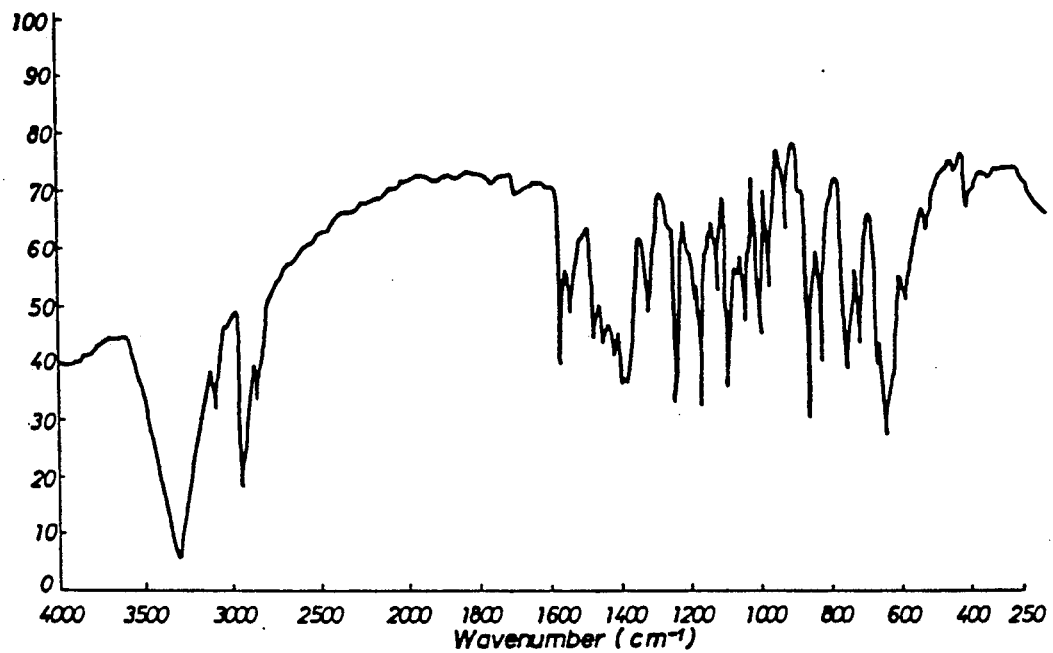
Figure 86:
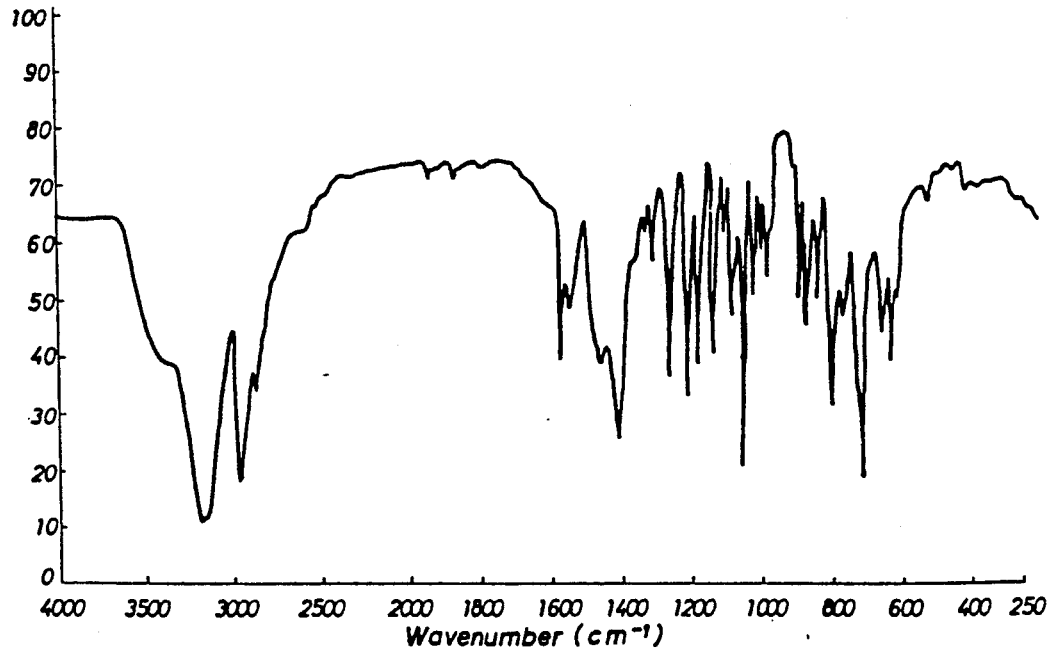
Figure 87:
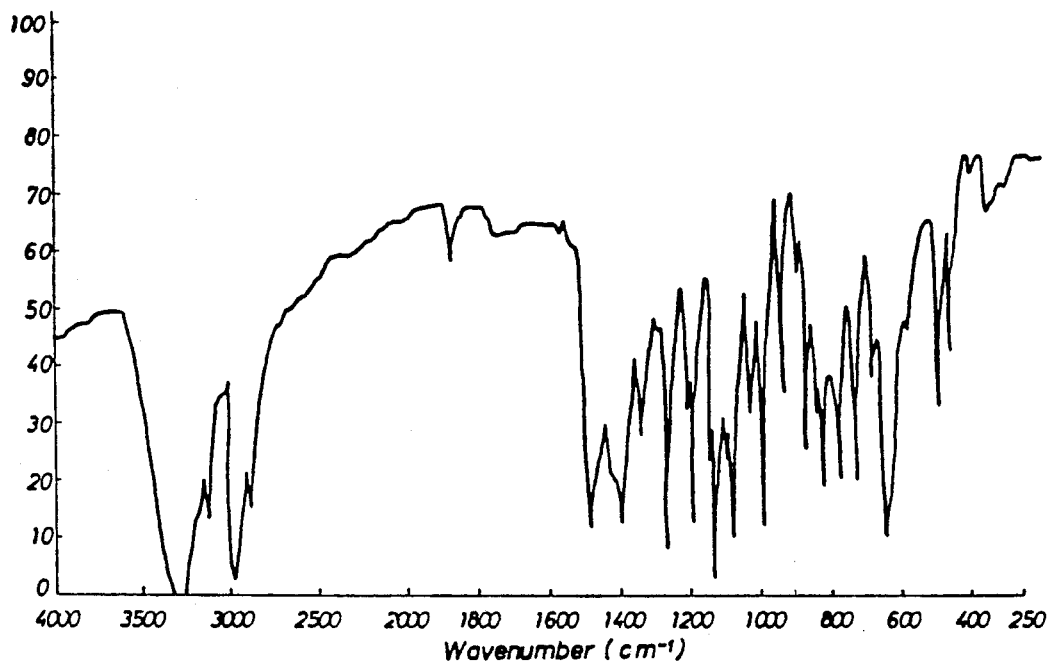
Figure 88:
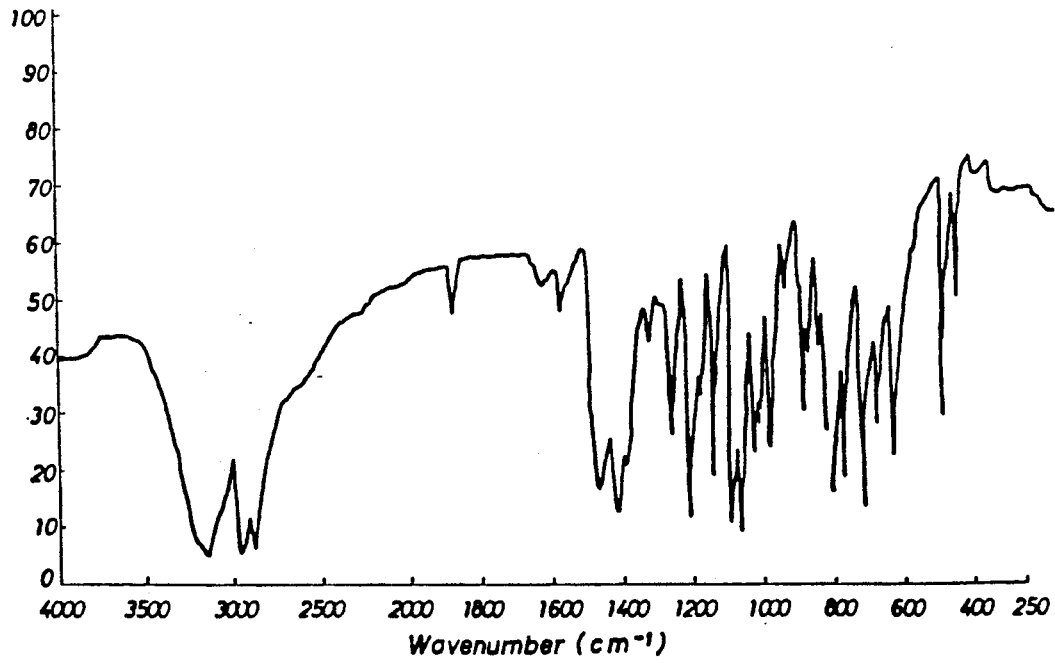
Figure 89:
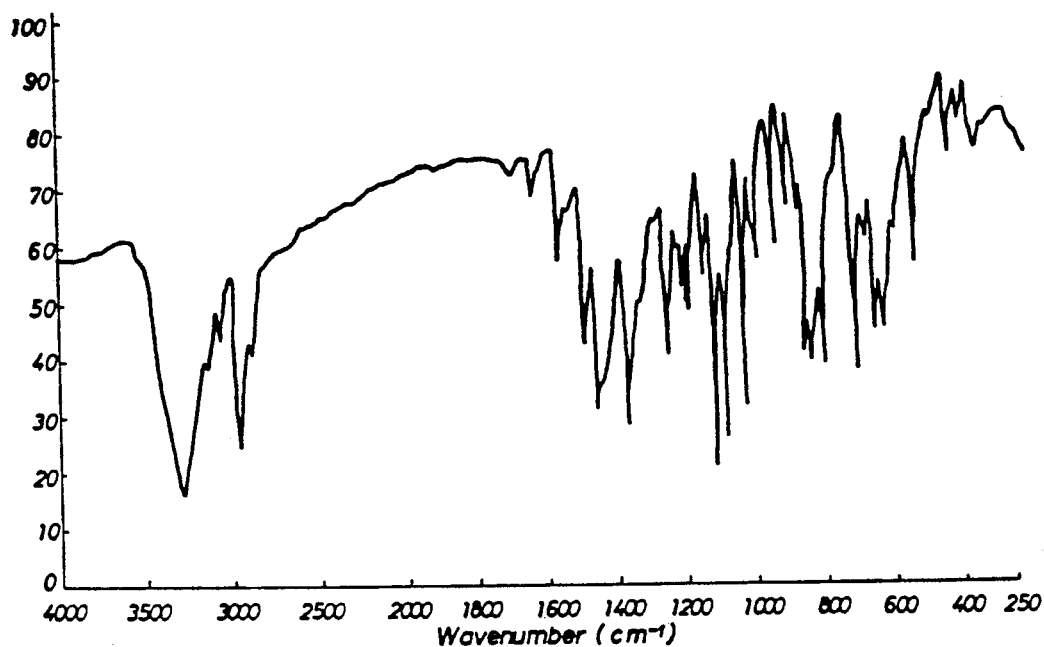
Figure 90:
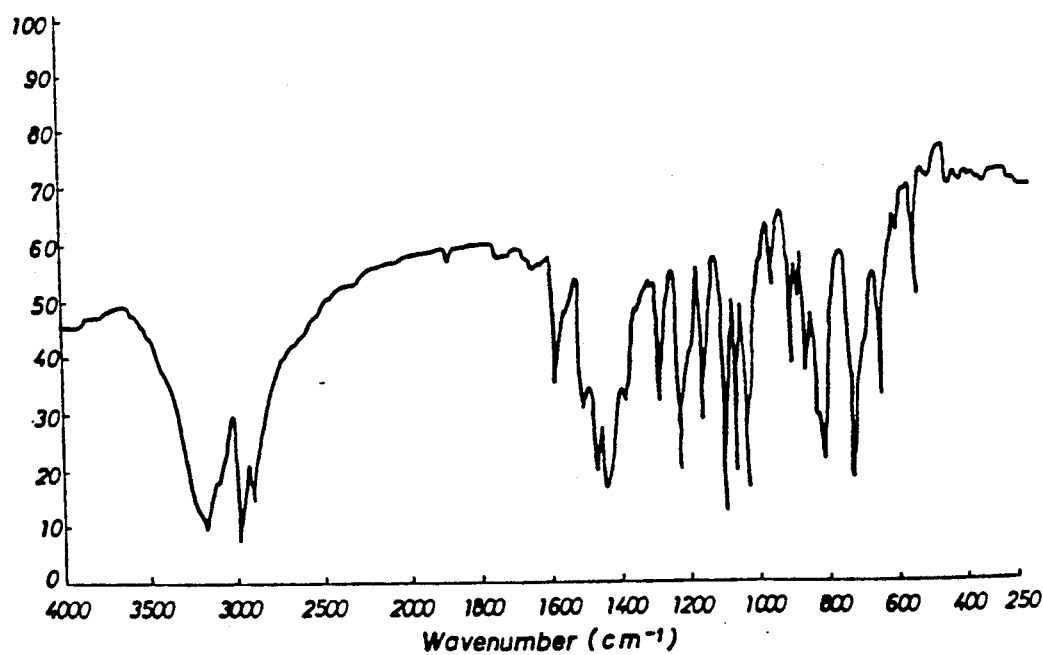
Figure 91:
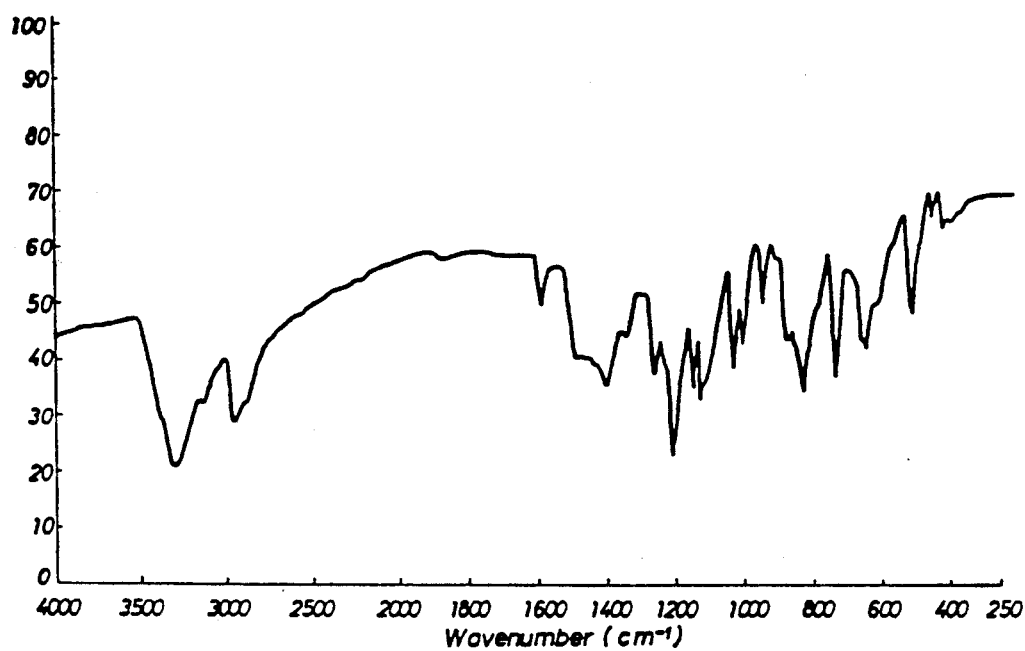
Figure 92:
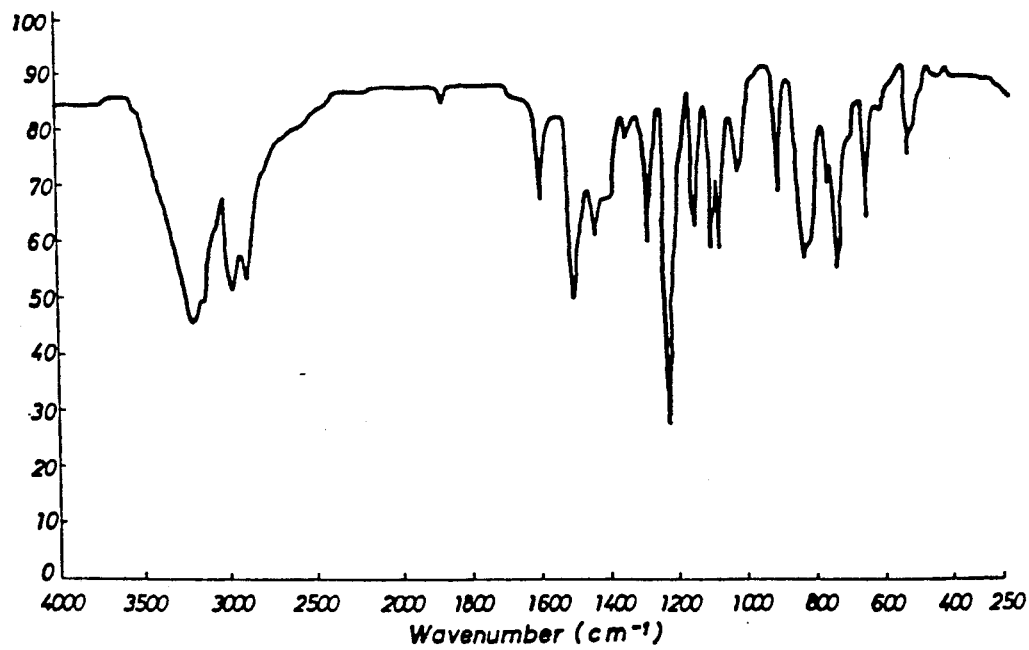
Figure 93:
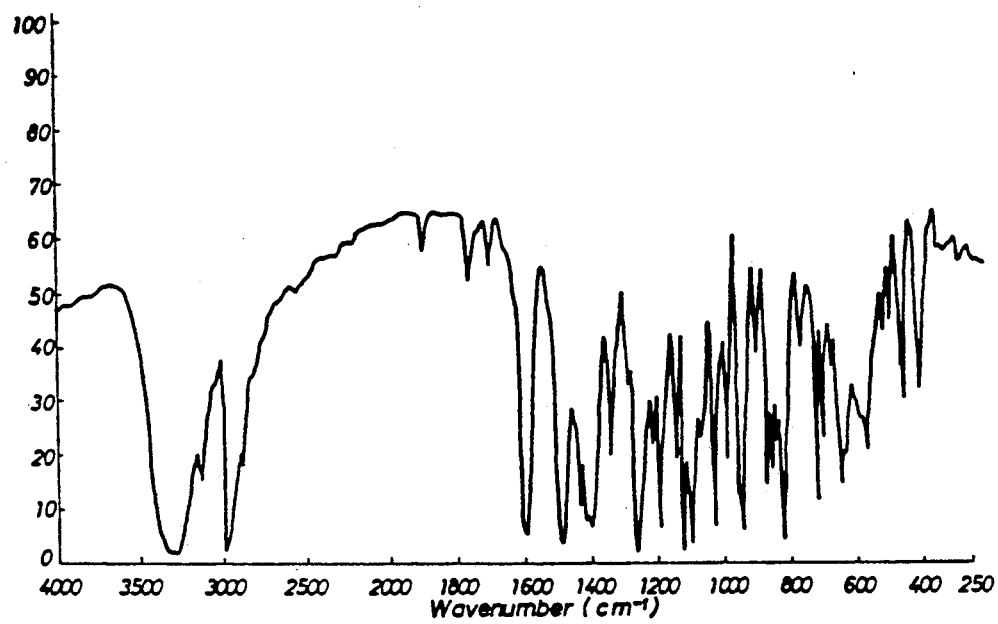
Figure 94:
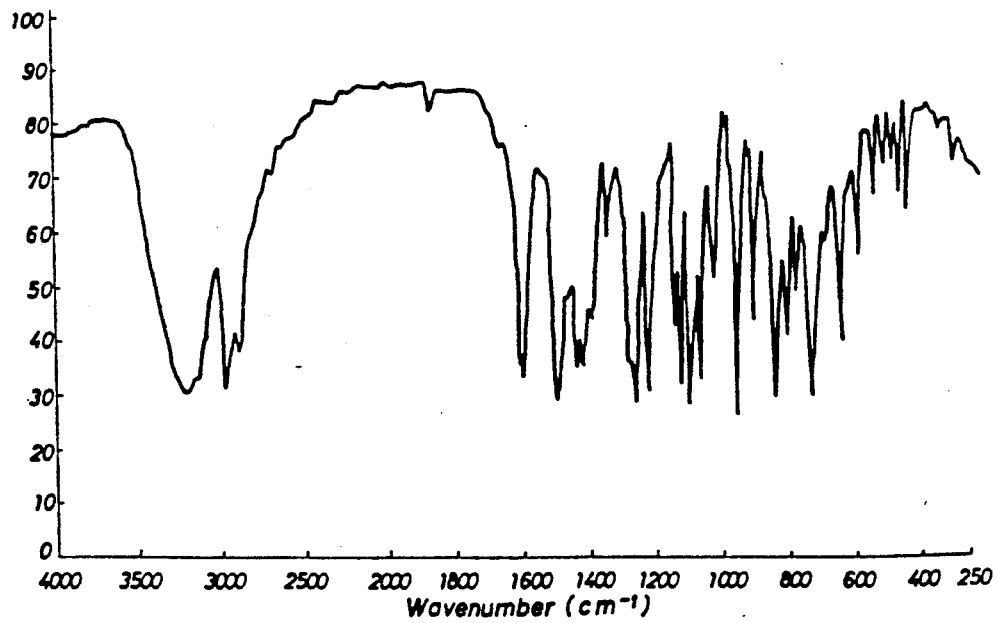
Figure 95:
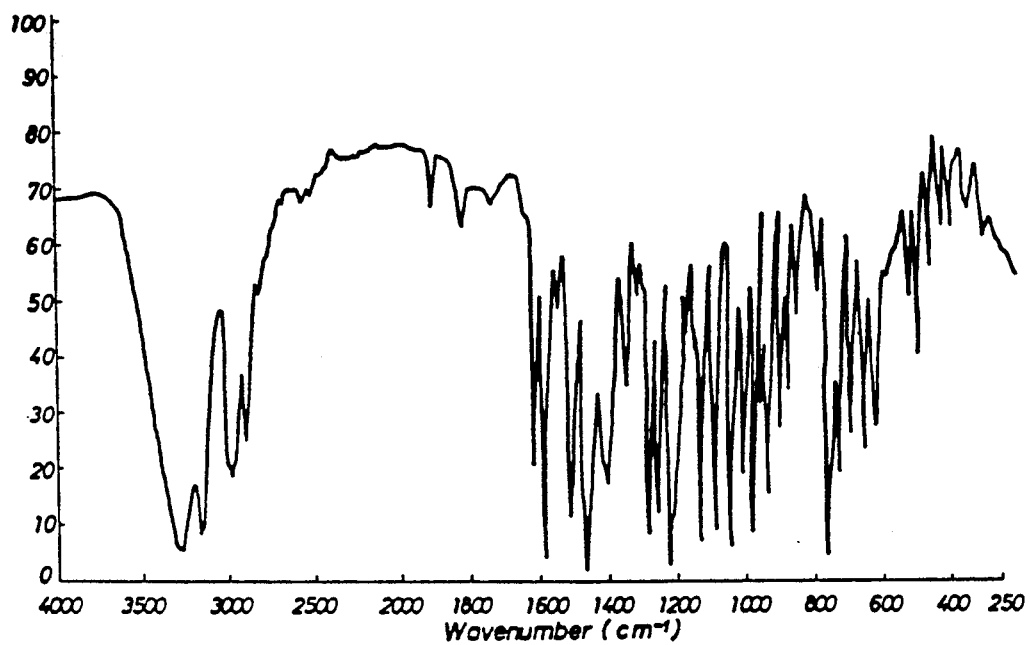
Figure 96:
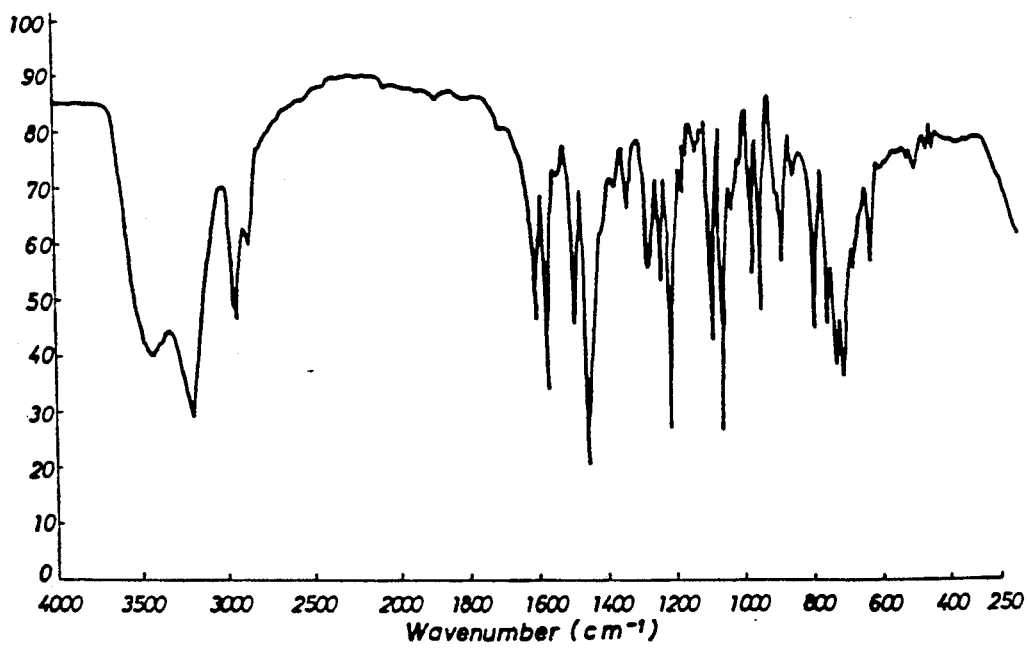
Figure 97:
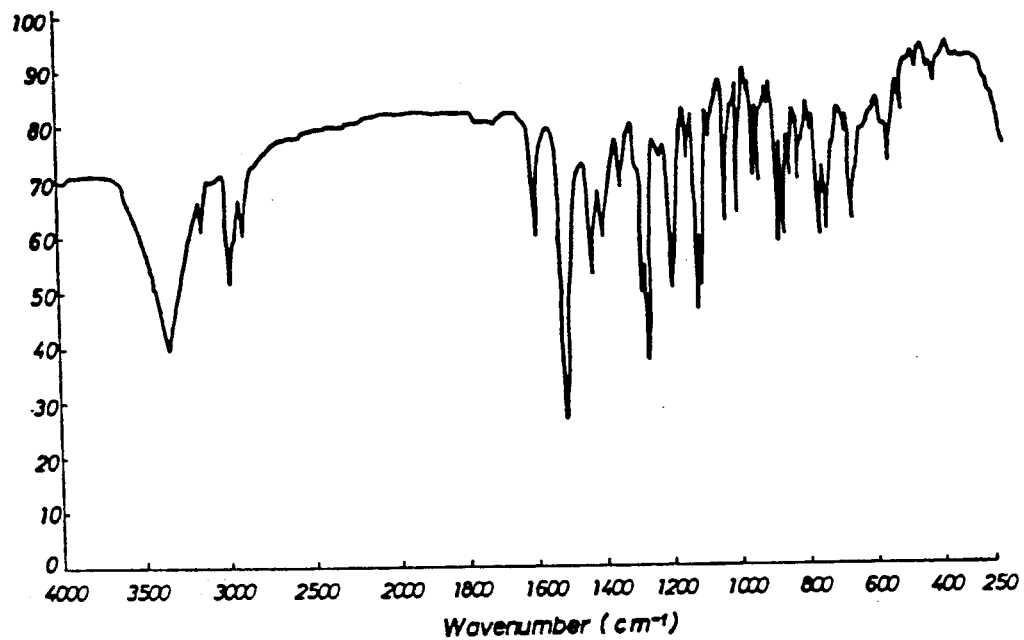
Figure 98:
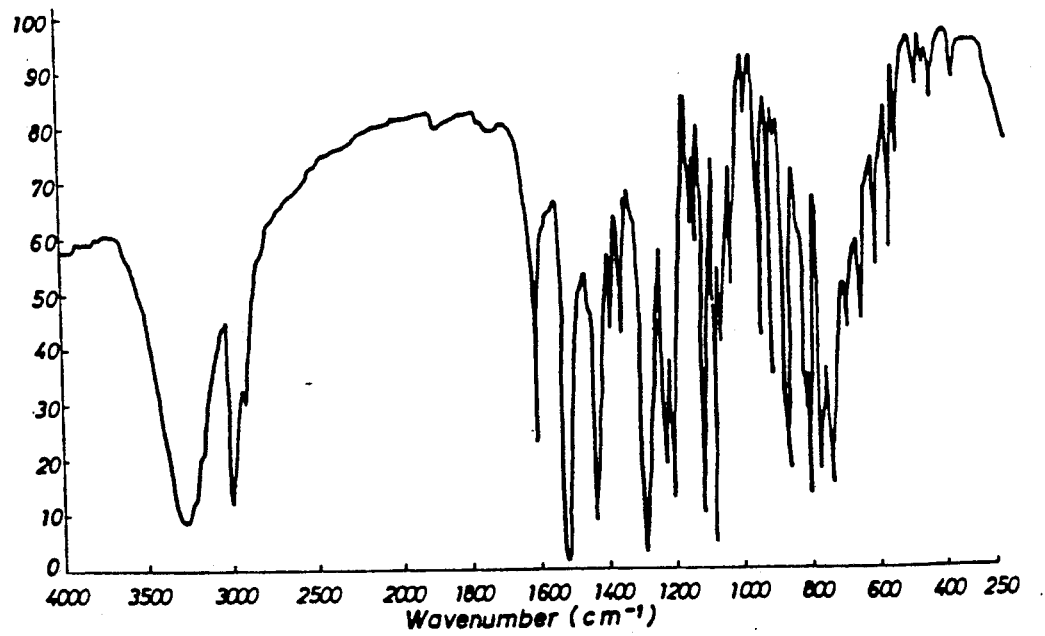
Figure 99:
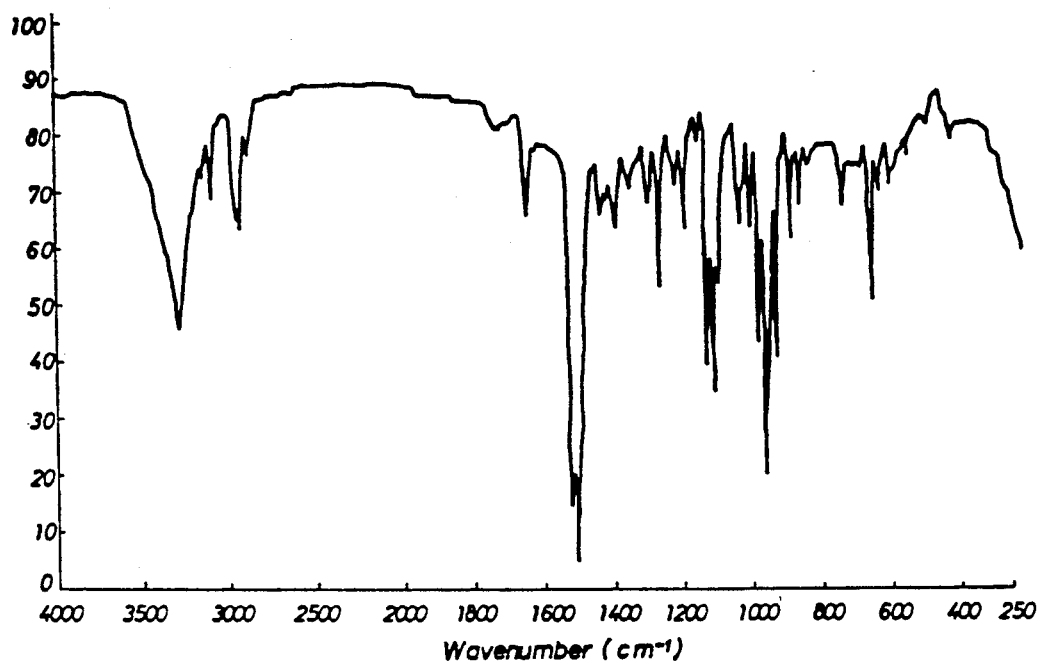
Figure 100:
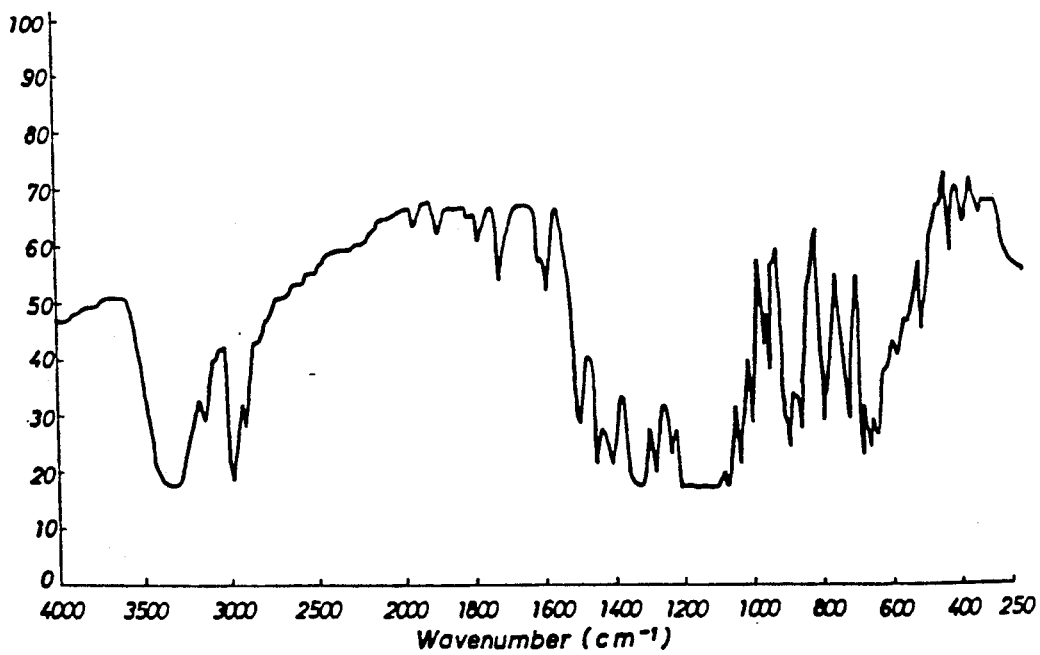
Figure 101:
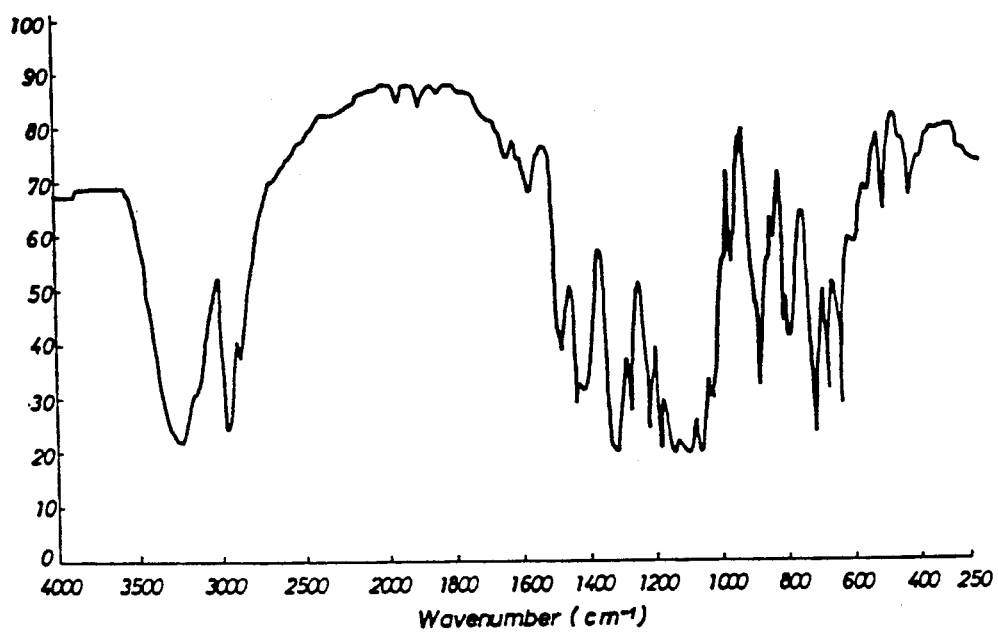
Figure 102:
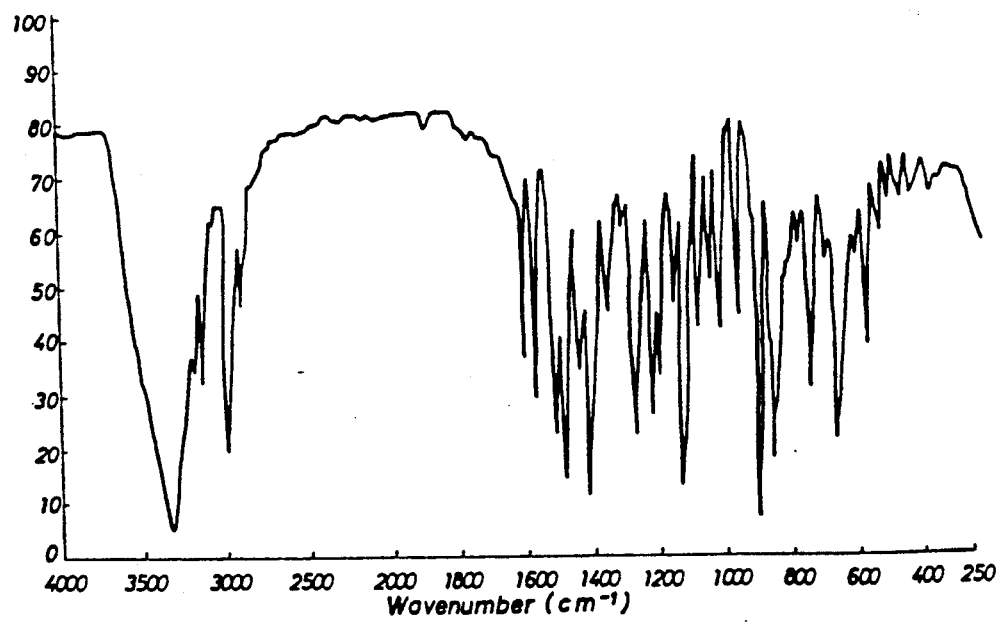
Figure 103:
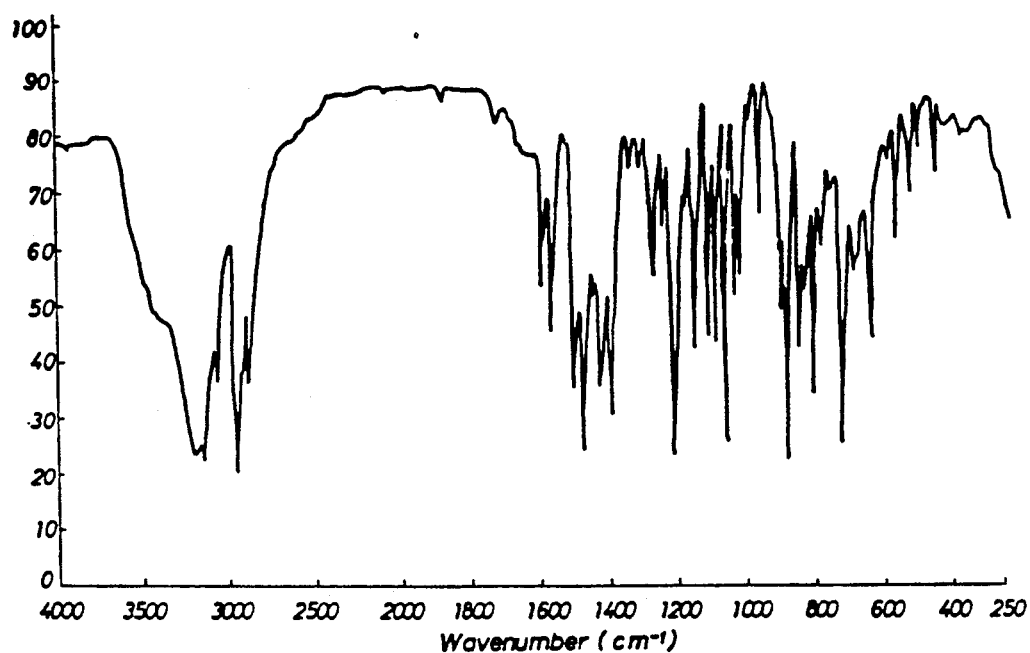
Figure 104:
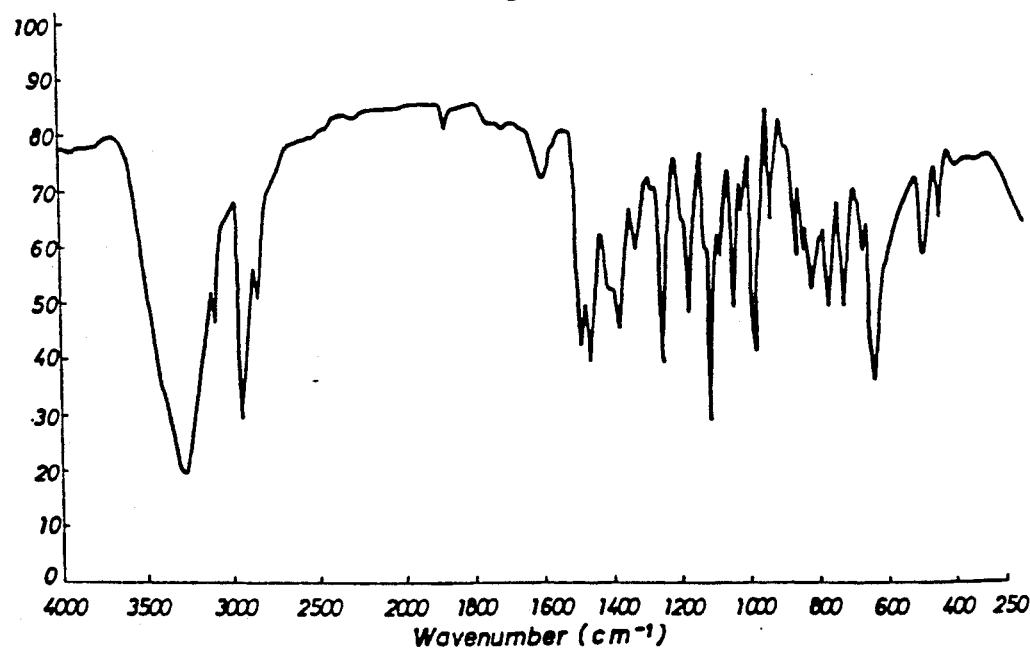
Figure 105:
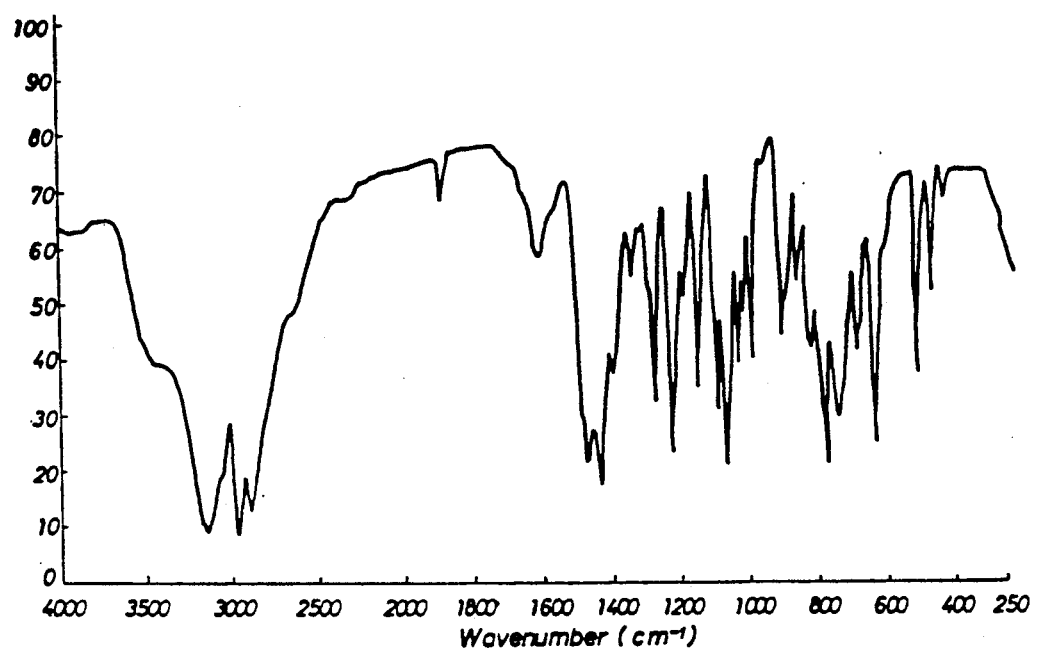
Figure 106:
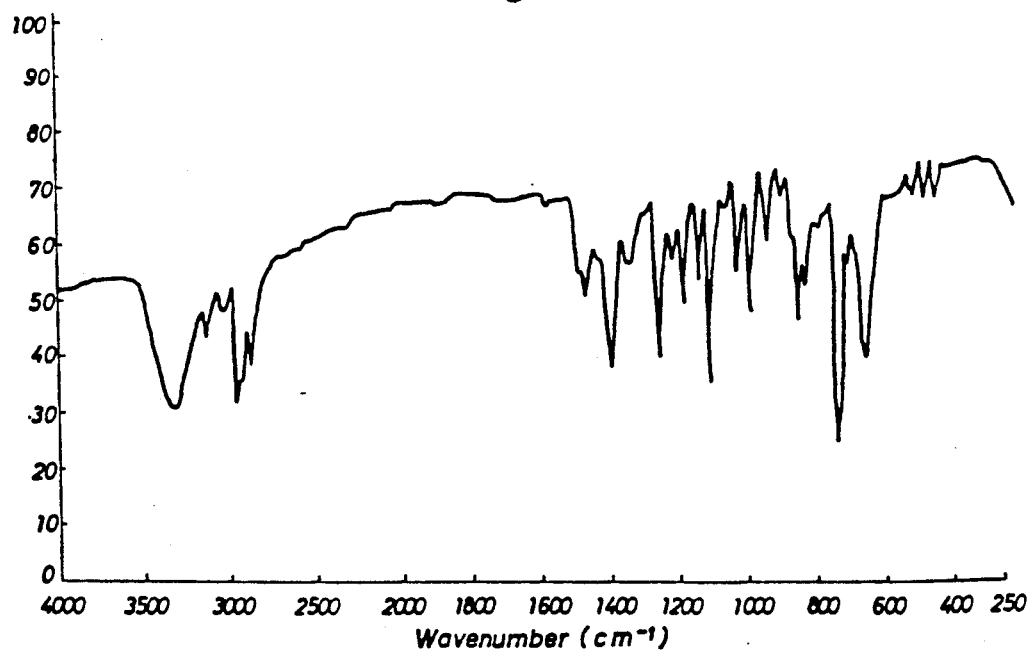
Figure 107:
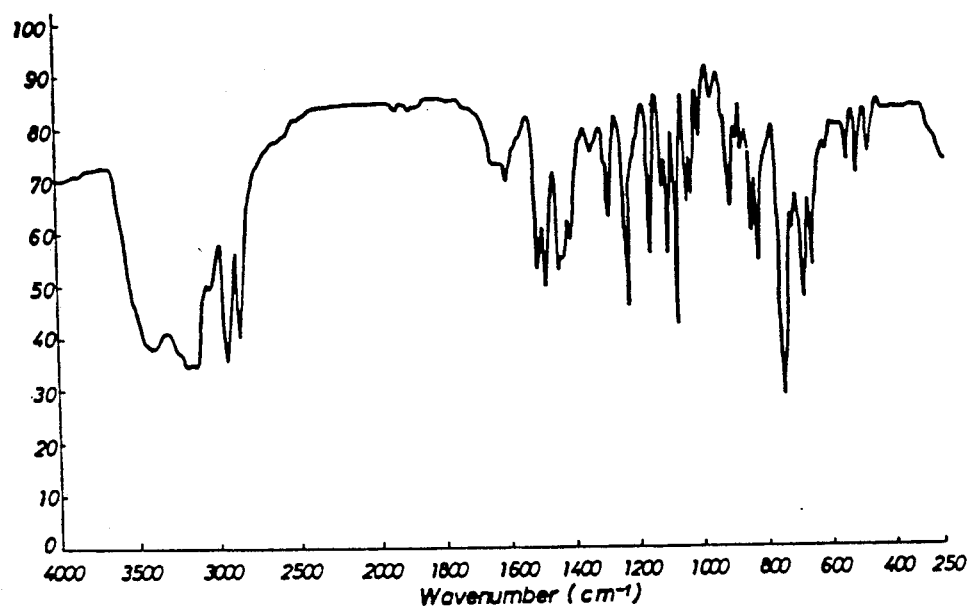
Figure 108:
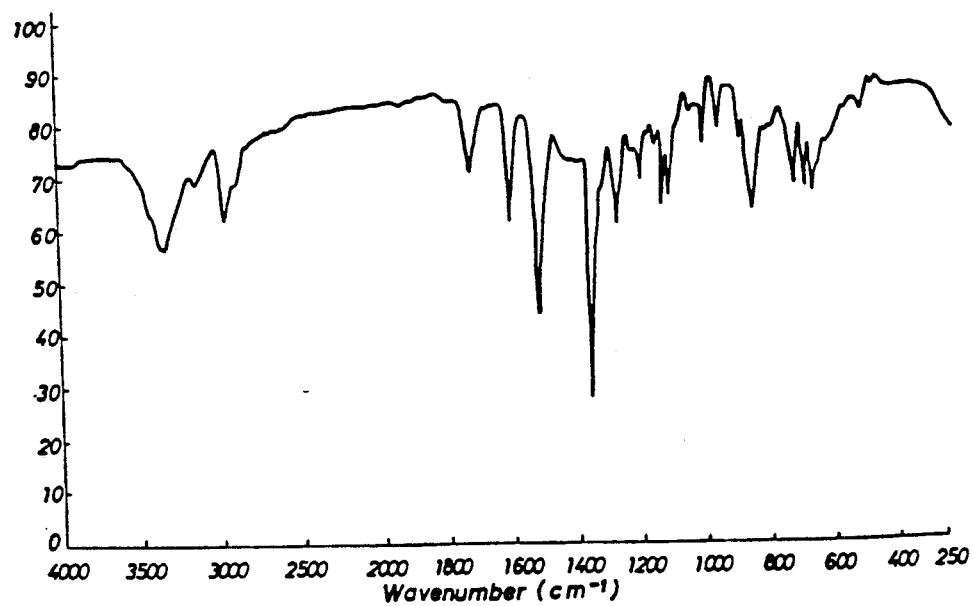
Figure 109:
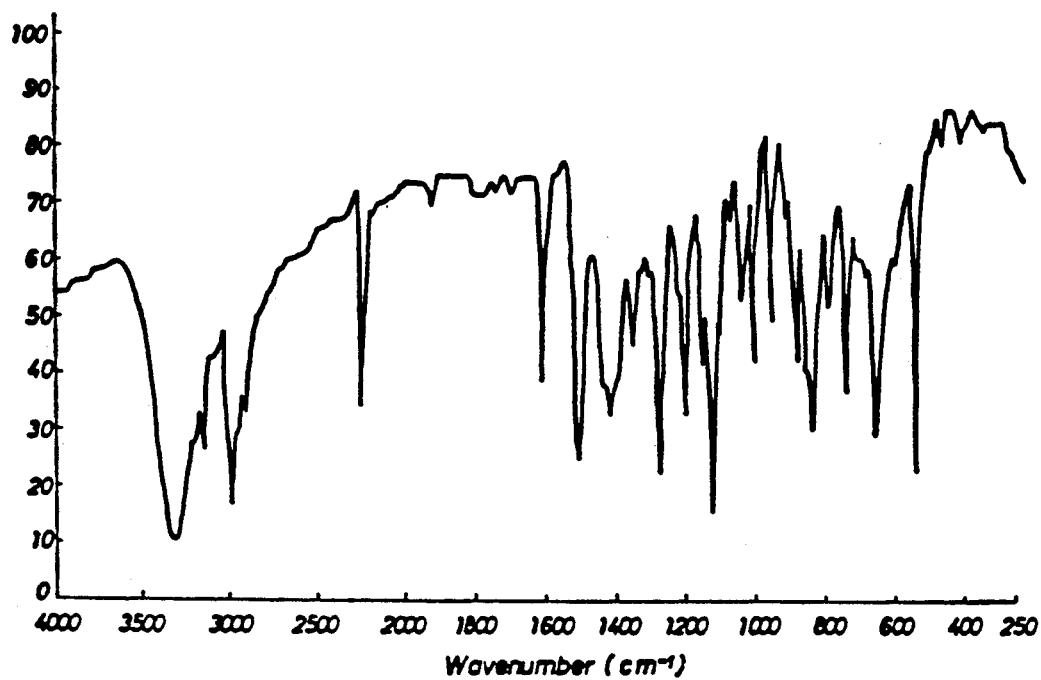
Figure 110:
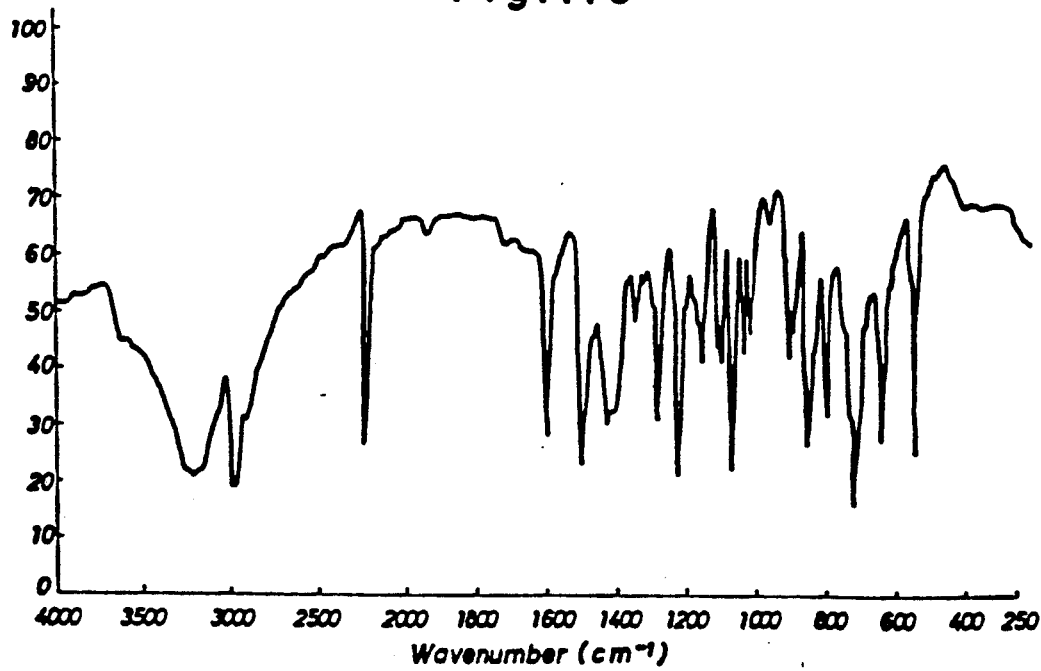

The compounds of the present invention and the compounds used in the present invention are represented by the following formula (II):

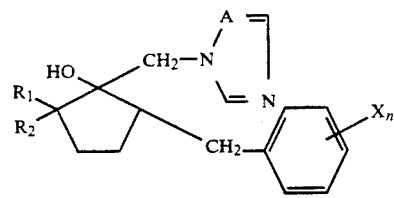

(II)

wherein X represents a halogen atom, an alkyl group having 1 to 5 carbon atoms, a haloalkyl group, a phenyl group, a cyano group, or a nitro group, Xs being either the same or different from each other; n represents an integer of 0 to 5; A represents a nitrogen atom or CH; and $R_1$ and $R_2$ respectively represent a hydrogen atom or an alkyl group having 1 to 5 carbon atoms.

Among these, X is preferably a halogen atom or a phenyl group, n is preferably 1 or 2, and $R_1$ and $R_2$ are preferably alkyl groups having 1 to 3 carbon atoms.

Since the compounds used in the present invention have an azolylmethyl group at the 1-position, a hydrogen atom or an alkyl group having 1 to 5 carbon atoms at the 2-position, and a substituted benzyl group at the 5-position, respectively, of a cyclopentane ring, the compounds have geometric isomers and optical isomers. The compounds of the present invention include all these respective isomers and mixtures of any number of isomers in any ratio. Accordingly, the mycocide according to the present invention may contain a single isomer or a mixture of these isomers as an effective ingredient.

The compounds of the present invention represented by the formula (I) can be synthesized in accordance with a method described in Japanese Patent Application Nos. 60-202431 (1985) and 61-265559 (1986).

The compounds represented by the formula (II) and the physicochemical properties (melting points) thereof are shown in Table 1. "A type" and "B type" in Table 1 represent the following two types.

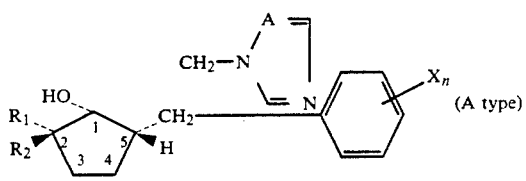

(A type)

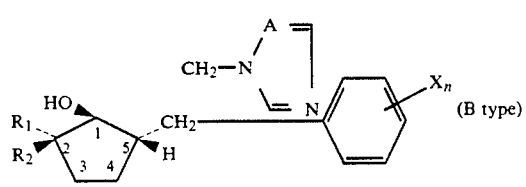

(B type)

--- = backward from the plane
— = on the plane
▶ = forward from the plane

TABLE 1

Azole derivative

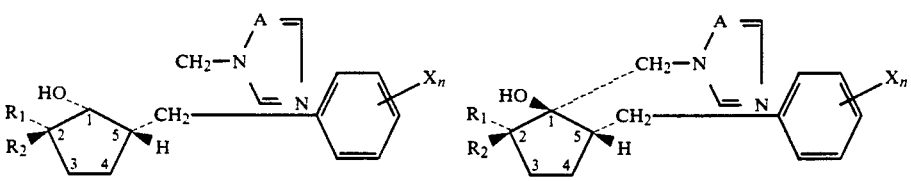

(A type)        (B type)

| Compound No. | $R_1$ | $R_2$ | $X_n$ | A | Type of stereo-isomer | Melting point (°C.) |
|---|---|---|---|---|---|---|
| 1 | $CH_3$ | $CH_3$ | 4-Cl | N | A | 113–114 |
| 2 | $CH_3$ | $CH_3$ | 4-Cl | N | B | 113–114 |
| 3 | $CH_3$ | $CH_3$ | 4-Cl | CH | A | 133–134 |
| 4 | $CH_3$ | $CH_3$ | 4-Cl | CH | B | 133–134 |
| 5 | $CH_3$ | $CH_3$ | 4-Br | N | A | 129–130 |
| 6 | $CH_3$ | $CH_3$ | 4-Br | N | B | 134–135 |
| 7 | $CH_3$ | $CH_3$ | 4-Br | CH | A | 149–150 |
| 8 | $CH_3$ | $CH_3$ | 4-Br | CH | B | 134–135 |
| 9 | $CH_3$ | $CH_3$ | 4-F | N | A | 135–136 |
| 10 | $CH_3$ | $CH_3$ | 4-F | N | B | 134–135 |
| 11 | $CH_3$ | $CH_3$ | 4-F | CH | A | 131–133 |
| 12 | $CH_3$ | $CH_3$ | 4-F | CH | B | 104–106 |
| 13 | $CH_3$ | $CH_3$ | 2,4-$Cl_2$ | N | A | 126–127 |
| 14 | $CH_3$ | $CH_3$ | 2,4-$Cl_2$ | N | B | 108–110 |
| 15 | $CH_3$ | $CH_3$ | 2,4-$Cl_2$ | CH | A | 131–132 |
| 16 | $CH_3$ | H | 4-Cl | N | A | 100–102 |
| 17 | $CH_3$ | H | 4-Cl | CH | A | 118–119 |
| 18 | H | $CH_3$ | 4-Cl | N | A | 75–76 |
| 19 | H | $CH_3$ | 4-Cl | N | B | 79–81 |
| 20 | $CH_3$ | H | 4-Cl | N | B | Oily matter |
| 21 | $CH_3$ | $CH_3$ | H | N | A | Oily matter |
| 22 | $CH_3$ | $CH_3$ | H | CH | A | 128–130 |
| 23 | $CH_3$ | $CH_3$ | 4-$CH_3$ | N | A | 123–124 |
| 24 | $CH_3$ | $CH_3$ | 4-$CH_3$ | N | B | 114–115 |
| 25 | $CH_3$ | $CH_3$ | 4-$CH_3$ | CH | A | 132–133 |
| 26 | $CH_3$ | $CH_3$ | 4-$CH_3$ | CH | B | 130–131 |
| 27 | $CH_3$ | $CH_3$ | 2-F, 4-Cl | N | A | 129–130 |
| 28 | $CH_3$ | $CH_3$ | 2-F, 4-Cl | CH | A | 152–154 |
| 29 | $C_2H_5$ | H | 4-Cl | N | A | 82–84 |
| 30 | H | $C_2H_5$ | 4-Cl | N | A | 93–95 |
| 31 | H | $C_2H_5$ | 4-Cl | N | B | 76–78 |
| 32 | $C_2H_5$ | H | 4-Cl | N | B | 110–112 |
| 33 | $C_2H_5$ | $C_2H_5$ | 4-Cl | N | A | 124–126 |
| 34 | $C_2H_5$ | $C_2H_5$ | 4-Cl | N | B | 143–145 |
| 35 | $C_2H_5$ | $C_2H_5$ | 4-Cl | CH | A | Oily matter |
| 36 | $C_2H_5$ | $C_2H_5$ | 4-Cl | CH | B | 143–145 |
| 37 | $n-C_3H_7$ | H | 4-Cl | N | A | 83–85 |
| 38 | H | $n-C_3H_7$ | 4-Cl | N | A | 75–77 |
| 39 | $n-C_3H_7$ | H | 4-Cl | CH | A | 115–117 |
| 40 | $C_2H_5$ | H | 2,4-$Cl_2$ | N | A | 124–127 |
| 41 | $C_2H_5$ | H | 2,4-$Cl_2$ | CH | A | 111–113 |
| 42 | $C_2H_5$ | H | 4-F | N | A | 73–74 |
| 43 | $C_2H_5$ | H | 4-F | CH | A | 111–113 |
| 44 | $C_2H_5$ | H | 4-Br | N | A | 80–82 |
| 45 | $C_2H_5$ | H | 4-Br | CH | A | 117–119 |
| 46 | $C_2H_5$ | H | 4-$C_6H_5$ | N | A | 107–109 |
| 47 | $C_2H_5$ | H | 4-$C_6H_5$ | CH | A | 169–170 |
| 48 | $C_2H_5$ | H | 4-$t-C_4H_9$ | N | A | Oily matter |
| 49 | $C_2H_5$ | H | 4-$t-C_4H_9$ | CH | A | 132–133 |
| 50 | $i-C_3H_7$ | H | 4-Cl | N | A | 91–92 |
| 51 | $n-C_5H_{11}$ | H | 4-Cl | N | A | Oily matter |
| 52 | $n-C_5H_{11}$ | H | 4-Cl | CH | A | 92–95 |
| 53 | $C_2H_5$ | H | 4-Cl | CH | B | 138–140 |
| 54 | H | $n-C_5H_{11}$ | 4-Cl | N | A | Oily matter |
| 55 | $CH_3$ | $CH_3$ | 4-$C_6H_5$ | N | A | 122–124 |
| 56 | $CH_3$ | $CH_3$ | 4-$C_6H_5$ | N | B | 116–118 |
| 57 | $CH_3$ | $CH_3$ | 4-$C_6H_5$ | CH | A | 162–163 |
| 58 | $CH_3$ | $CH_3$ | 4-$C_6H_5$ | CH | B | 165–167 |
| 59 | $i-C_3H_7$ | H | 4-Cl | CH | A | Oily matter |
| 60 | $CH_3$ | $CH_3$ | 4-$t-C_4H_9$ | N | A | 107–108 |
| 61 | $CH_3$ | $CH_3$ | 4-$t-C_4H_9$ | CH | A | 167–168 |
| 62 | H | $i-C_3H_7$ | 4-Cl | N | B | Oily matter |
| 63 | H | $i-C_3H_7$ | 4-Cl | N | A | 102–103 |
| 64 | H | $i-C_3H_7$ | 4-Cl | CH | A | 146–147 |
| 65 | $i-C_3H_7$ | H | 4-Cl | N | B | 120–121 |
| 66 | $n-C_4H_9$ | H | 4-Cl | CH | A | Oily matter |
| 67 | H | $n-C_4H_9$ | 4-Cl | N | A | 94–95 |
| 68 | H | $n-C_4H_9$ | 4-Cl | N | B | Oily matter |

TABLE 1-continued

Azole derivative (A type)     (B type)

| Compound No. | $R_1$ | $R_2$ | $X_n$ | A | Type of stereo-isomer | Melting point (°C.) |
|---|---|---|---|---|---|---|
| 69 | i-$C_4H_9$ | H | 4-Cl | N | A | Oily matter |
| 70 | i-$C_4H_9$ | H | 4-Cl | CH | A | Oily matter |
| 71 | n-$C_4H_9$ | H | 4-Cl | N | A | Oily matter |
| 72 | | | | | | |
| Isomer a | $CH_3$ | $C_2H_5$ | 4-Cl | N | A | 72-a, 72-b mixture |
| Isomer b | $C_2H_5$ | $CH_3$ | 4-Cl | N | A | 98–101 |
| 73 | | | | | | |
| Isomer a | $CH_3$ | $C_2H_5$ | 4-Cl | N | B | 73-a, 73-b, Mixture |
| Isomer b | $C_2H_5$ | $CH_3$ | 4-Cl | N | B | 117–119 |
| 74 | | | | | | |
| Isomer a | $CH_3$ | $C_2H_5$ | 4-Cl | N | B | 74-a, 74-b, Mixture |
| Isomer b | $C_2H_5$ | $CH_3$ | 4-Cl | N | B | 122–127 |
| 75 | $CH_3$ | $CH_3$ | 4-t-$C_4H_9$ | N | B | Oily matter |
| 76 | $CH_3$ | $CH_3$ | 4-t-$C_4H_9$ | CH | B | 132–133 |
| 77 | H | H | H | N | A | 140–141 |
| 78 | H | H | H | CH | A | 130–131 |
| 79 | H | H | 4-$CH_3$ | N | A | 128–129 |
| 80 | H | H | 4-$CH_3$ | CH | A | 122–123 |
| 81 | H | H | 4-t-$C_4H_9$ | N | A | 129–130 |
| 82 | H | H | 4-t-$C_4H_9$ | CH | A | 123–124 |
| 83 | H | H | 2-Cl | N | A | 154–155 |
| 84 | H | H | 2-Cl | CH | A | 103–104 |
| 85 | H | H | 3-Cl | N | A | 152–153 |
| 86 | H | H | 3-Cl | CH | A | 105–106 |
| 87 | H | H | 4-Cl | N | A | 115–116 |
| 88 | H | H | 4-Cl | CH | A | 115–116 |
| 89 | H | H | 2,4-$Cl_2$ | N | A | 120–121 |
| 90 | H | H | 2,4-$Cl_2$ | CH | A | 150–151 |
| 91 | H | H | 4-F | N | A | 135–136 |
| 92 | H | H | 4-F | CH | A | 139–140 |
| 93 | H | H | 2,4-$F_2$ | N | A | 118–119 |
| 94 | H | H | 2,4-$F_2$ | CH | A | 144–145 |
| 95 | H | H | 2,6-$F_2$ | N | A | 104–105 |
| 96 | H | H | 2,6-$F_2$ | CH | A | 150–151 |
| 97 | H | H | 3,4-$F_2$ | N | A | 119–121 |
| 98 | H | H | 3,4-$F_4$ | CH | A | 103–105 |
| 99 | H | H | 2,3,4,5,6-$F_5$ | N | A | 118–120 |
| 100 | H | H | 3-$CF_3$ | N | A | 152–153 |
| 101 | H | H | 3-$CF_3$ | CH | A | 87–88 |
| 102 | H | H | 2-F, 4-Cl | N | A | 125–127 |
| 103 | H | H | 2-F, 4-Cl | CH | A | 141–143 |
| 104 | H | H | 4-Br | N | A | 106–107 |
| 105 | H | H | 4-Br | CH | A | 119–120 |
| 106 | H | H | 4-$C_6H_5$ | N | A | 146–147 |
| 107 | H | H | 4-$C_6H_5$ | CH | A | 182–183 |
| 108 | H | H | 4-$NO_2$ | N | A | 131–132 |
| 109 | H | H | 4-CN | N | A | 115–116 |
| 110 | H | H | 4-CN | CH | A | 103–104 |

Medicines which contain a compound represented by the general formula (II) or medically or veterinarily acceptable salt thereof, e.g., a salt of an inorganic acid such as a nitric acid, sulfuric acid and hydrochloric acid and a salt of an organic acid such as a fumaric acid and naphthalene-1,5-disulfonic acid and a diluent or a carrier which is medically or veterinarily acceptable are medicines which show a mycocidal activity and are useful for treating mycosis of animals including man. For example, these medicines are useful for treating a local mycosis of man caused by a fungus belonging to the genus such as Candida, Trichophyton, Microsporum and Epidermophyton or a mucosal mycosis caused by C. albicans, e.g., candidiasis of mouth and candidiasis of vagina. These medicines can also be used for treating a systemic mycosis caused by C. albicans, Cryptococcus neoformans, Aspergillus fumigatus, or a fungus belonging to genus such as Coccidioides, Paracoccidiodes, Histoplasma and Blastomyces.

When the compounds represented by the formula (II) is used for man, they may be used singly, but they are generally administered in the form of a mixture with a carrier and/or diluent which is selected in accordance with desired administration route and unit dosage form. For example, these compounds may be orally administered in the form of a tablet containing an excipient such as starch and lactose, in the form of a capsule or ovules in a single state or in a state of being mixed with an excipient, or in the form of an elixir or a suspension containing a flavor or coloring agent. These compounds may also be parenterally administered, for example, by intravenous injection, subcutaneous injection, intramascular injection or the like. In the case of administering such a medicine parenterally, it is most preferable that the medicine is used in the form of a germfree aqueous solution containing a sufficient amount of salt or glucose for making an injection solution isotonic with blood.

The compounds represented by the formula (II) may also be administered in the form of a suppository or a vaginal suppository, or applied to the affected part in the form of a lotion, liquid, cream, ointment or dusting powder. For example, these compounds may be added to a cream comprising an aqueous emulsion of polyethylene glycol or liquid paraffin. These compounds may also be added in the range of 1 to 10% concentration to an ointment comprising white Japan wax or white liquid paraffin and necessary stabilizer and antiseptic.

The ordinary dosage of the compound represented by the formula (II) for man is 0.1 to 40 mg/kg per day, whether it is administered orally or parenterally. It is therefore possible to use a tablet or a capsule of this compound which contains 1 mg to 0.5 g of the compound in order to administer one or more of them every time, as occasion demands. The actual optimum dosage is judged by a doctor in accordance with the age, weight, sensitivity, and degree of infection of the patient. The above-described dosage is for an average case, and the effective range of dosage naturally fluctuates depending on cases, such range being included in the present invention.

These compounds may be administered to animals other than man by the same administration methods and dosage (0.1 to 40 mg/kg.day) as in the case of man.

The mycocidal activity in vitro of the compounds represented by the formula (II) can be evaluated by measuring the minimum inhibitory concentration (hereinunder referred to as "M.I.C.") of the test compounds for inhibiting the growth of a specific fungus in an appropriate culture medium. Actually, standard culture of C. albicans, for example, is inoculated into a series of agar plates containing test compounds in a predetermined concentration. After each agar plate is cultivated at a predetermined temperature for a predetermined time, whether C. albicans has grown or not is examined to determine the M.I.C. of the corresponding compound. Other fungi such as *Cryptococcus neoformans,* Candida spp.,*Torulopsis glabrata,* Aspergillus spp.,*Cladosporium carrionii, Fonsecaea pendrosoi,* Microsporum spp., *E. floccosum, Phialophora verrucosa, C. immitis* and *Sporothrix schenckii* are also usable in this kind of test.

The effectiveness of the compounds represented by the formula (II) to fungi will now be shown with reference to the following non-limitative examples.

EXAMPLE 1

The anti-fungus activities in vitro of the compounds represented by the formula (II) were examined. Testing method:

Each of the compounds shown in Table 2 was dissolved in dimethylsulfoxide so as to have a predetermined concentration. In a petri dish, were well mixed 0.1 m( of the compound and 9.9 ml Sabouraud's agar culture medium of about 60° C. to be solidified. The spores of a test fungus which had been cultivated in a plate culture medium at 28° C. for 20 to 30 days was suspended in 0.1% Tween 80 solution (Polyoxyethylene Sorbitan Monooleate). The suspension was adjusted by using 0.1% Tween 80 solution so as to have a spore concentration of $10^5$ to $10^6$ spores/ml. Into the plate medium containing the test compound, 5 µl of the fungus suspension was inoculated. After the inoculation, the fungus was cultivated at 28° C. Whether the fungus had grown or not was judged 4 days after the inoculation in the case of Aspergillus, and 7 days after the inoculation in the case of the other fungi to obtain the M.I.C.

The degree of growth inhibition was evaluated into 5 stages in accordance with the following standards. The results are shown in Table 2.

Growth inhibition

5 M.I.C<3.13 ppm
4 3.13 ppm≦M.I.C.<12.5 ppm
3 12.5 ppm≦M.I.C.<50 ppm
2 50 ppm≦M.I.C.<=100 ppm
1 100 ppm<M.I.C.

TABLE 2

| Compound No. | Test fungus | | | | | | | |
|---|---|---|---|---|---|---|---|---|
| | A. fla. | A. nig. | C. car. | F. pen. | M. gyp. | P. ver. | T. men. | T. rub. |
| 3 | 5 | 4 | 4 | 5 | 3 | 4 | 4 | 4 |
| 7 | 5 | 5 | 5 | 5 | 5 | 5 | 5 | 5 |
| 11 | 5 | 4 | 5 | 5 | 5 | 4 | 5 | 5 |
| 13 | 4 | 3 | 2 | 3 | 3 | 1 | 3 | 3 |
| 15 | 5 | 4 | 4 | 4 | 5 | 3 | 5 | 5 |
| 16 | 5 | 5 | 5 | 5 | 5 | 5 | 5 | 5 |
| 17 | 5 | 4 | 4 | 5 | 4 | 4 | 5 | 5 |
| 29 | 4 | 3 | 4 | 4 | 4 | 3 | 4 | 4 |
| 35 | 5 | 5 | 5 | 5 | 4 | 5 | 5 | 4 |
| 37 | 5 | 4 | 4 | 4 | 4 | 3 | 4 | 4 |
| 39 | 5 | 5 | 5 | 5 | 5 | 5 | 5 | 5 |
| 41 | 4 | 3 | 3 | 3 | 4 | 3 | 5 | 4 |
| 45 | 5 | 5 | 5 | 5 | 5 | 4 | 5 | 5 |
| 47 | 5 | 5 | 5 | 5 | 5 | 5 | 5 | 5 |
| 52 | 5 | 5 | 5 | 5 | 5 | 5 | 5 | 5 |
| 57 | 5 | 5 | 5 | 5 | 5 | 5 | 5 | 5 |
| 59 | 5 | 5 | 5 | 5 | 5 | 5 | 5 | 5 |
| 71 | 5 | 3 | 5 | 5 | 5 | 3 | 4 | 4 |
| 107 | 5 | 5 | 5 | 5 | 4 | 5 | 5 | 5 |

Explanation of Abbreviations:
A.fla.; *Aspergillus flavus*
A.nig.; *Aspergillus niger*
C.car.; *Cladosporium carrionii*
F.pen.; *Fonsecaea pendrosoi*
M.gyp.; *Microsporium gypseum*
P.ver.; *Phialophora verrucosa*
T.men.; *Trichophyton mentagrophytes*
T.rub.; *Trichophyton rubrum*

EXAMPLE 2

The anti-yeast fungal activities in vitro of the compounds represented by the formula (II) were examined. Testing method:

Each of the compounds shown in Table 3 was dissolved in dimethylsulfoxide so as to have a predetermined concentration. In a petri dish, were well mixed 0.1 ml of the compound and 9.9 ml Sabouraud's agar culture medium of about 60° C. to be solidified. A test fungus which had been cultivated in a liquid culture medium in advance was suspended in a physiological saline solution so as to have a fungus concentration of 105 to 106 cells/ml. Into the plate culture medium containing the test compound shown in Table 3, 5 μl of the fungus solution was inoculated. After the inoculation, the fungus was cultivated at 37° C. for 2 days. Whether the fungus had grown or not was judged to obtain the M.I.C.

The degree of growth inhibition was evaluated into 5 stages in accordance with the following standards. The results are shown in Table 3.

Growth inhibition

5 M.I.C. < 3.13 ppm
4 3.13 ppm ≦ M.I.C. < 12.5 ppm
3 12.5 ppm ≦ M.I.C. < 50 ppm
2 50 ppm ≦ M.I.C. ≦ 100 ppm
1 100 ppm < M.I.C.

TABLE 3

| Compound No. | Test fungus | | | | | | | | |
|---|---|---|---|---|---|---|---|---|---|
| | C. alb. | C. ste. | C. pse. | C. par. | C. tro. | C. kru. | C. gui. | T. gla. | C. neo. |
| 1 | 2 | 2 | 3 | 4 | 3 | 4 | 4 | 3 | 5 |
| 3 | 3 | 3 | 4 | 4 | 4 | 5 | 5 | 5 | 5 |
| 4 | 3 | 3 | 3 | 3 | 3 | 3 | 3 | 3 | 4 |
| 5 | 2 | 2 | 3 | 3 | 3 | 4 | 4 | 4 | 5 |
| 6 | 2 | 3 | 3 | 2 | 1 | 1 | 3 | 3 | 3 |
| 7 | 3 | 3 | 4 | 5 | 4 | 5 | 5 | 4 | 5 |
| 8 | 3 | 3 | 3 | 3 | 2 | 3 | 3 | 3 | 4 |
| 9 | 2 | 2 | 2 | 3 | 2 | 3 | 4 | 3 | 4 |
| 10 | 2 | 2 | 2 | 2 | 2 | 2 | 3 | 2 | 3 |
| 11 | 2 | 2 | 3 | 3 | 2 | 4 | 4 | 4 | 4 |
| 12 | 2 | 2 | 2 | 2 | 2 | 3 | 2 | 2 | 3 |
| 13 | 3 | 3 | 3 | 1 | 1 | 1 | 3 | 2 | 3 |
| 14 | 3 | 3 | 3 | 1 | 1 | 1 | 2 | 2 | 3 |
| 15 | 3 | 3 | 4 | 4 | 3 | 4 | 4 | 3 | 4 |
| 16 | 2 | 2 | 2 | 2 | 1 | 3 | 3 | 2 | 4 |
| 17 | 3 | 4 | 3 | 4 | 3 | 4 | 4 | 4 | 4 |
| 19 | 3 | 3 | 2 | 1 | 1 | 1 | 2 | 1 | 4 |
| 21 | 3 | 5 | 2 | 2 | 2 | 3 | 3 | 3 | 5 |
| 22 | 3 | 5 | 3 | 4 | 3 | 4 | 3 | 4 | 5 |
| 23 | 2 | 2 | 2 | 2 | 2 | 2 | 2 | 3 | 3 |
| 25 | 3 | 4 | 4 | 5 | 4 | 5 | 4 | 5 | 5 |
| 26 | 3 | 3 | 3 | 3 | 2 | 3 | 3 | 3 | 4 |
| 27 | 3 | 3 | 3 | 3 | 3 | 4 | 3 | 3 | 4 |
| 28 | 4 | 5 | 4 | 5 | 4 | 5 | 5 | 4 | 5 |
| 29 | 4 | 5 | 3 | 4 | 3 | 4 | 3 | 4 | 5 |
| 30 | 4 | 5 | 3 | 4 | 3 | 5 | 4 | 4 | 5 |
| 31 | 3 | 5 | 3 | 2 | 2 | 2 | 3 | 2 | 5 |
| 32 | 4 | 5 | 3 | 3 | 3 | 3 | 4 | 3 | 5 |
| 33 | 4 | 3 | 3 | 4 | 3 | 4 | 4 | 4 | 4 |
| 34 | 3 | 2 | 2 | 1 | 1 | 2 | 2 | 2 | 4 |
| 36 | 3 | 1 | 4 | 4 | 3 | 4 | 4 | 5 | 4 |
| 37 | 4 | 5 | 3 | 4 | 3 | 5 | 4 | 5 | 5 |
| 38 | 3 | 3 | 3 | 5 | 3 | 5 | 4 | 4 | 5 |
| 39 | 4 | 4 | 4 | 5 | 5 | 5 | 5 | 5 | 5 |
| 40 | 3 | 3 | 3 | 1 | 1 | 1 | 2 | 2 | 4 |
| 41 | 4 | 4 | 4 | 4 | 3 | — | 4 | 4 | 5 |
| 42 | 3 | 5 | 2 | 3 | 2 | 3 | 2 | 4 | 5 |
| 43 | 3 | 4 | 3 | 5 | 3 | 5 | 4 | 5 | 4 |
| 44 | 3 | 5 | 3 | 3 | 2 | 4 | 3 | 3 | 5 |
| 45 | 4 | 5 | 3 | 5 | 4 | 5 | 4 | 5 | 5 |
| 47 | 5 | 5 | 5 | 5 | 1 | 4 | 4 | 3 | 5 |
| 48 | 2 | 3 | 2 | 1 | 2 | 1 | 1 | 1 | 5 |
| 49 | 4 | 5 | 3 | 2 | 2 | 2 | 3 | 3 | 5 |
| 50 | 3 | 3 | 2 | 4 | 3 | 4 | 3 | 4 | 4 |
| 51 | 1 | 2 | 1 | 4 | 1 | 3 | 1 | 3 | 2 |
| 52 | 3 | 3 | 4 | 5 | 4 | 5 | 4 | 5 | 5 |
| 53 | 4 | 5 | 4 | 4 | 4 | 4 | 4 | 4 | 5 |
| 54 | 1 | 4 | 1 | 4 | 1 | 4 | 2 | 3 | 5 |
| 57 | 4 | 4 | 4 | 4 | 1 | 4 | 4 | 4 | 5 |
| 58 | 4 | 5 | 4 | 4 | 4 | 4 | 4 | 4 | 5 |
| 59 | 4 | 5 | 4 | 5 | 5 | 5 | 4 | 5 | 5 |
| 60 | 3 | 5 | 3 | 1 | 1 | 1 | 1 | 2 | 5 |
| 61 | 4 | 5 | 5 | 3 | 3 | 3 | 3 | 4 | 5 |
| 63 | 3 | 5 | 3 | 5 | 5 | 5 | 3 | 5 | 5 |
| 64 | 4 | 5 | 4 | 5 | 5 | 5 | 3 | 4 | 5 |
| 65 | 3 | 5 | 3 | 4 | 3 | 3 | 3 | 4 | 5 |
| 66 | 4 | 5 | 5 | 5 | 5 | 5 | 4 | 5 | 5 |
| 67 | 3 | 5 | 3 | 5 | 4 | 4 | 4 | 4 | 5 |
| 68 | 3 | 5 | 3 | 3 | 1 | 1 | 3 | 3 | 5 |
| 69 | 3 | 5 | 3 | 4 | 3 | 4 | 3 | 3 | 5 |
| 70 | 4 | 5 | 5 | 5 | 5 | 5 | 4 | 5 | 5 |
| 71 | 5 | 5 | 3 | 3 | 2 | 5 | 2 | 5 | 5 |
| 75 | 2 | 3 | 3 | 1 | 1 | 1 | 1 | 1 | 4 |
| 76 | 3 | 4 | 4 | 2 | 2 | 2 | 3 | 3 | 5 |
| 80 | 2 | 2 | 2 | 2 | 1 | 2 | 2 | 1 | 3 |
| 82 | 2 | 2 | 3 | 2 | 2 | 2 | 2 | 3 | 3 |
| 84 | 2 | 2 | 3 | 2 | 1 | 1 | 2 | 2 | 2 |
| 86 | 3 | 2 | 3 | 2 | 1 | 1 | 2 | 1 | 3 |
| 87 | 2 | 2 | 2 | 2 | 1 | 2 | 3 | 1 | 3 |
| 90 | 3 | 2 | 3 | 2 | 2 | 2 | 3 | 1 | 2 |
| 92 | 2 | 1 | 2 | 2 | 1 | 2 | 3 | 1 | 2 |
| 97 | 2 | 2 | 2 | 2 | 1 | 1 | 2 | 2 | 1 |
| 98 | 2 | 2 | 2 | 3 | 2 | 2 | 3 | 3 | 1 |
| 101 | 2 | 2 | 3 | 2 | 1 | 1 | 2 | 2 | 2 |
| 102 | 2 | 2 | 2 | 2 | 1 | 2 | 3 | 2 | 2 |
| 103 | 3 | 3 | 3 | 3 | 2 | 3 | 3 | 2 | 2 |
| 104 | 2 | 2 | 2 | 2 | 1 | 2 | 3 | 2 | 3 |
| 105 | 3 | 2 | 3 | 3 | 2 | 3 | 3 | 2 | 3 |
| 107 | 3 | 3 | 4 | 2 | 2 | 3 | 3 | 3 | 4 |

Explanation of abbreviations:
C. alb. : Candida albicans
C. ste. : Candida stellatoidea
C. pse. : Candida pseudotropicalis
C. par. : Candida parapsilosis
C. tro. : Candida tropicalis
C. kru. : Candida krusei
C. gui. : Candida guilliermondii
T. gla. : Torulopsis glabrate
C. neo. : Cryptococcus neoformans

What is claimed is:

1. A mycocide composition comprising an effective amount of an azole derivative represented by the formula:

$$\text{(II)}$$

wherein X represents a halogen atom, an alkyl group having 1 to 5 carbon atoms, a halomethyl group, a phenyl group, a cyano group, or a nitro group, X being either the same or different from each other; n represents an integer of 0 to 5; A represents CH; and one of $R_1$ and $R_2$ represents an alkyl group having 1 to 5 carbon atoms and the other represents a hydrogen atom or an alkyl group having 1 to 5 carbon atoms, or a medically or veterinarily acceptable salt thereof, and a medically or veterinarily acceptable carrier or diluent.

2. A method for treating mycosis of man or an animal comprising administering thereto an effective amount of an azole derivative represented by the formula:

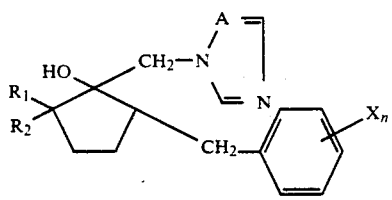

wherein X represents a halogen atom, an alkyl group having 1 to 5 carbon atoms, a halomethyl group, a phenyl group, a cyano group, or a nitro group, X being either the same or different from each other; n represents an integer of 0 to 5; A represents CH; and one of $R_1$ and $R_2$ represents an alkyl group having 1 to 5 carbon atoms and the other represents a hydrogen atom or an alkyl group having 1 to 5 carbon atoms, or a medically veterinarily acceptable salt thereof.

* * * * *